US012624027B2

(12) United States Patent
Loughrey et al.

(10) Patent No.: US 12,624,027 B2
(45) Date of Patent: May 12, 2026

(54) SALTS AND POLYMORPHIC FORMS OF 6-CHLORO-7-(4-(4-CHLOROBENZYL) PIPERAZIN-1-YL)-2-(1,3-DIMETHYL-1H-PYRAZOL-4-YL)-3H-IMIDAZO[4,5-B] PYRIDINE

(71) Applicants: ELLIPSES PHARMA LTD, London (GB); INSTITUTE OF CANCER RESEARCH: ROYAL CANCER HOSPITAL (THE), London (GB)

(72) Inventors: Jonathan Loughrey, Midlothian (GB); Natalie Kelk, Midlothian (GB); Michaela Kreiner, Glasgow (GB); Gavin Halbert, Glasgow (GB)

(73) Assignees: ELLIPSES PHARMA LTD, London (GB); INSTITUTE OF CANCER RESEARCH: ROYAL CANCER HOSPITAL (THE), London (GB)

( * ) Notice: Subject to any disclaimer, the term of this patent is extended or adjusted under 35 U.S.C. 154(b) by 753 days.

(21) Appl. No.: 17/909,283

(22) PCT Filed: Mar. 3, 2021

(86) PCT No.: PCT/GB2021/050531
§ 371 (c)(1),
(2) Date: Sep. 2, 2022

(87) PCT Pub. No.: WO2021/176216
PCT Pub. Date: Sep. 10, 2021

(65) Prior Publication Data

US 2023/0105181 A1 Apr. 6, 2023

(30) Foreign Application Priority Data

Mar. 4, 2020 (GB) ...................................... 2003100

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC .......................... C07D 471/04; C07B 2200/13
See application file for complete search history.

(56) References Cited

FOREIGN PATENT DOCUMENTS

WO WO 2007072017 A2 6/2007
WO WO-2013190319 A1 * 12/2013 ............. A61P 35/02

OTHER PUBLICATIONS

Gupta et al., Molecules 2018, 23, 1719, doi:10.3390/molecules23071719. (Year: 2018).*

(Continued)

*Primary Examiner* — Clinton A Brooks
*Assistant Examiner* — Izabela Schmidt
(74) *Attorney, Agent, or Firm* — Seed Intellectual Property Law Group LLP

(57) ABSTRACT

The present invention relates to salts and polymorphic forms of Compound A (6-chloro-7-(4-(4-chlorobenzyl)piperazin-1-yl)-2-(1,3-dimethyl-1H-pyrazol-4-yl)-3H-imidazo[4,5-b] pyridine), an inhibitor of Aurora kinase and FMS-like tyrosine kinase 3 (FLT3) activity. The present invention also relates to processes for the preparation of the salts and polymorphic forms of the compound, to pharmaceutical compositions comprising them, and to their use in the treatment of proliferative disorders, such as cancer, as well as other diseases or conditions in which Aurora kinase and/or FLT3 activity is implicated.

6 Claims, 55 Drawing Sheets

Form 1 - XRPD

(56) References Cited

OTHER PUBLICATIONS

Gupta et al., Salts of Therapeutic Agents: Chemical, Physicochemical, and Biological Considerations. Molecules 2018, 23, 1719. (Year: 2018).*

Director, Evaluation and Licensing Division, Pharmaceutical Affairs Bureau, MHLW, "Specifications: Test Procedures and Acceptance Criteria for New Drug Substances and New Drug Products: Chemical Substances," Notification No. 568 of the Evaluation and Licensing Division, PMSB, May 1, 2001 [with English Translation]. (90 pages).

Hirayama (ed.), "Pharmaceutical crystallization method," Yuki-Kagoubutsu Kesshou Sakusei Handbook—genri to know-how, Maruzen Publishing Co., Ltd., pp. 57-84, 2008 [with English Translation]. (42 pages).

Kawaguchi et al., "Pharmaceuticals and polymorphs; Drug and crystal polymorphism," Journal of Human Environmental Engineering 4(2):310-317, 2002 [with English Translation]. (18 pages).

Takada, "Screening and Selection of Drug Substance Forms at Drug Discovery Stage," Pharm Stage 6(10):20-25, Jan. 15, 2007 [with English Translation]. (17 pages).

Yamano, "Approach to Crystal Polymorph in Process Research of New Drug," Journal of Synthetic Organic Chemistry 65(9):907(69)-913(75), Sep. 1, 2007 [with English Translation]. (18 pages).

Bavetsias et al., "Optimization of Imidazo[4,5-b ]pyridine-Based Kinase Inhibitors: Identification of a Dual FLT3/Aurora Kinase Inhibitor as an Orally Bioavailable Preclinical Development Candidate for the Treatment of Acute Myeloid Leukemia," *J. Med. Chem.* 55:8721-8734, Oct. 8, 2012.

Caira, "Crystalline Polymorphism of Organic Compounds," *Topics in Current Chemistry* 198:164-208, 1998. (46 pages).

Byrn et al., "Pharmaceutical Solids: A Strategic Approach to Regulatory Considerations," Pharmaceutical Research 12 (7):945-954, Aug. 1995. (11 pages).

"Polymorphism in pharmaceutical solids", Grant (chapter 1), pp. 1-10 and J. K. Guillory (chapter 5), pp. 183-226, Dec. 31, 1999. (55 pages).

"Pharmaceutical Dosage Forms: Tablets" edited by Larry L. Augsburger, Stephen W. Hoag, 3rd edition, vol. 2, chapter 2, pp. 62-66, Dec. 31, 2008. (5 pages).

* cited by examiner

FIG. 1 – Form 1 – XRPD
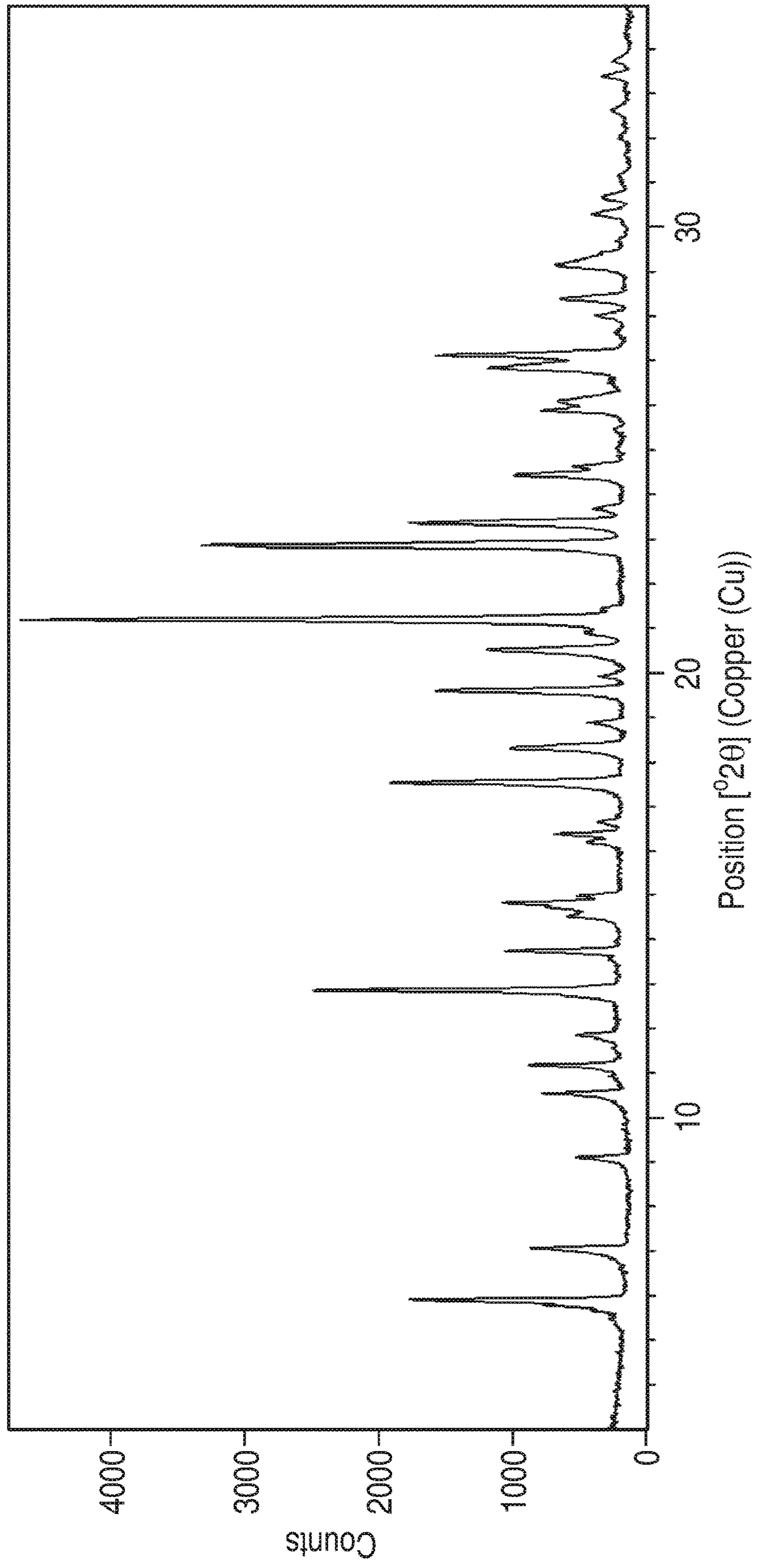

FIG. 2 – Form 2 – XRPD
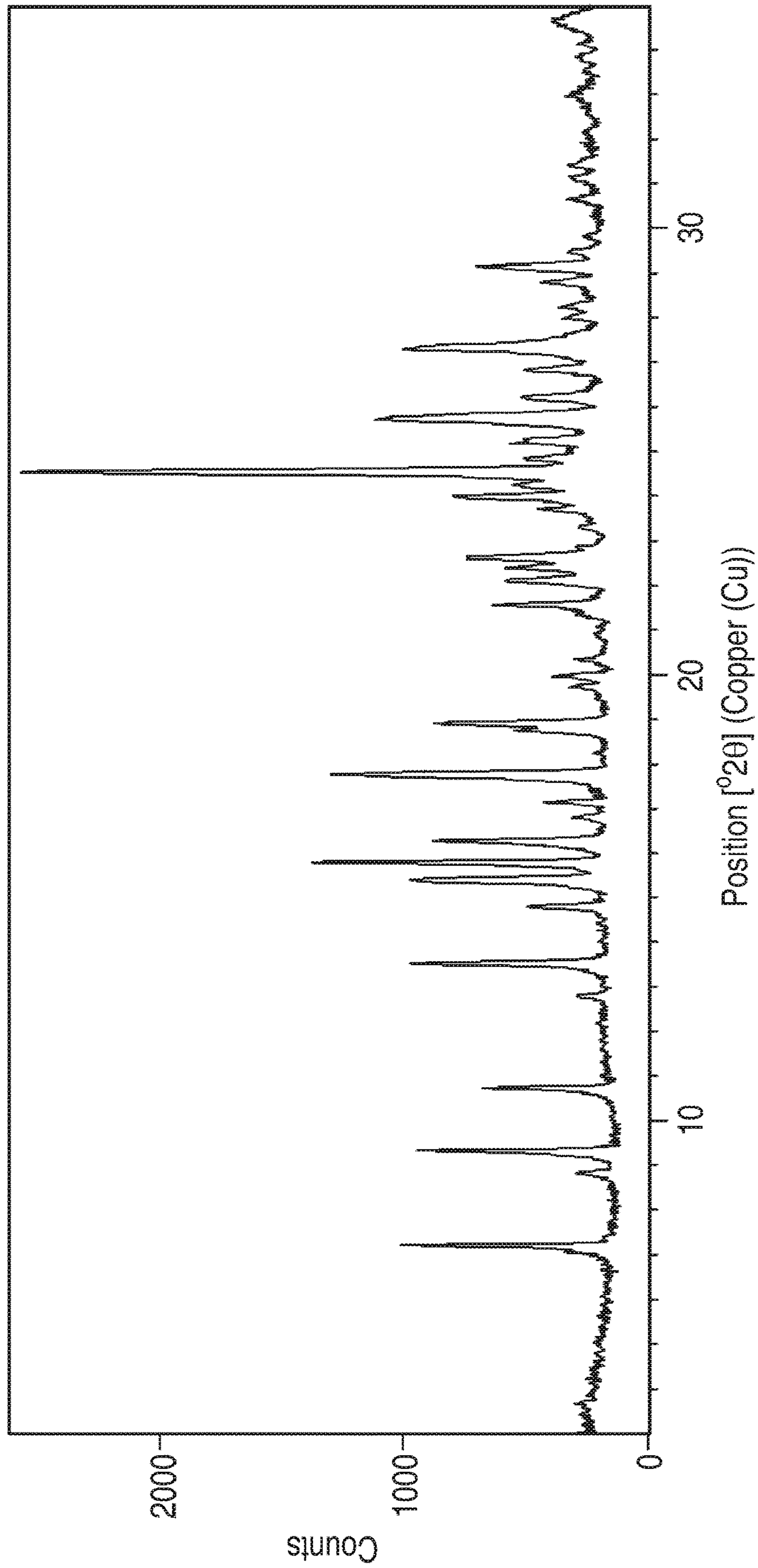

FIG. 3 – Form 3 – XRPD
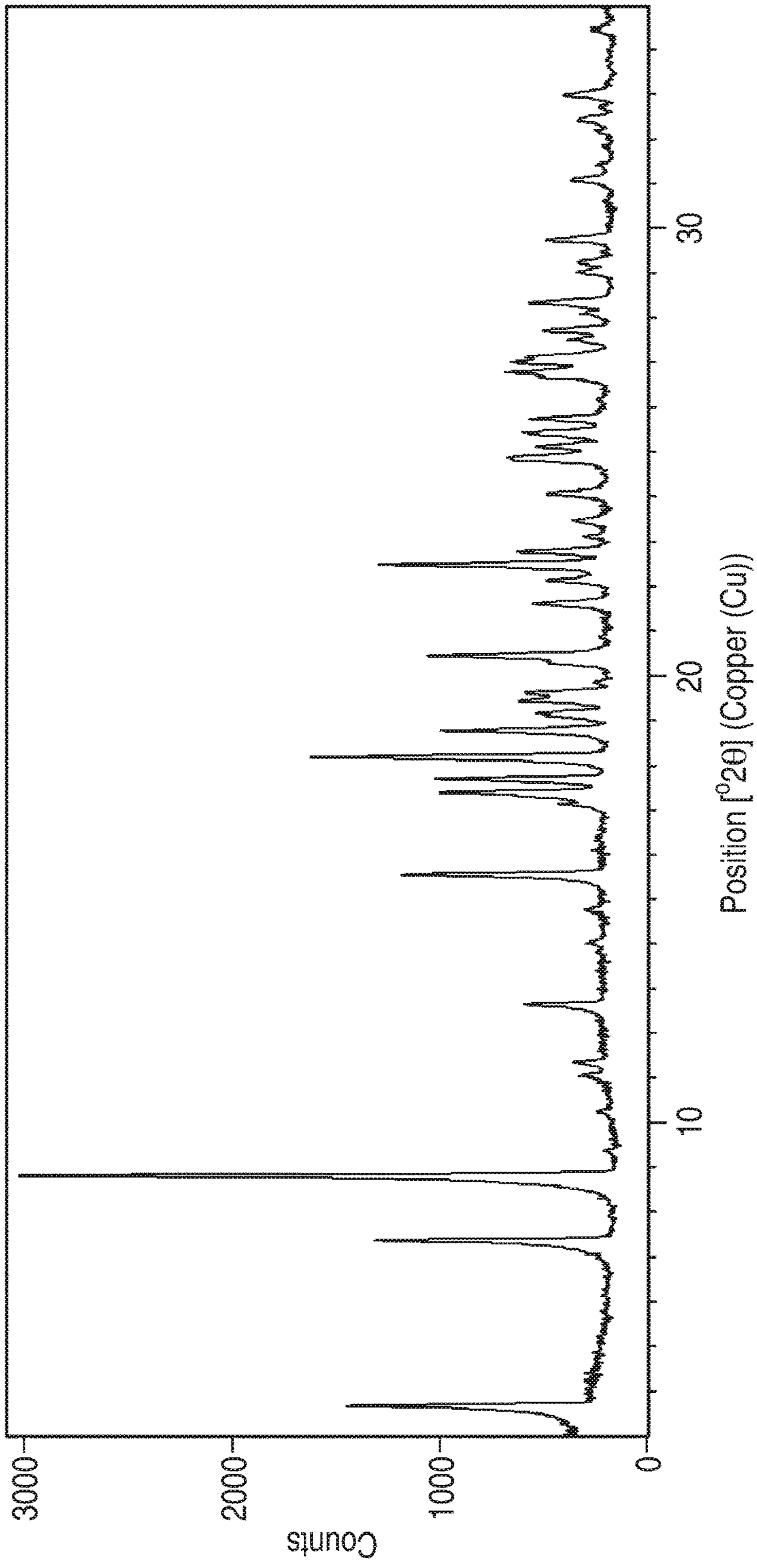

FIG. 4 – Form 4 – XRPD
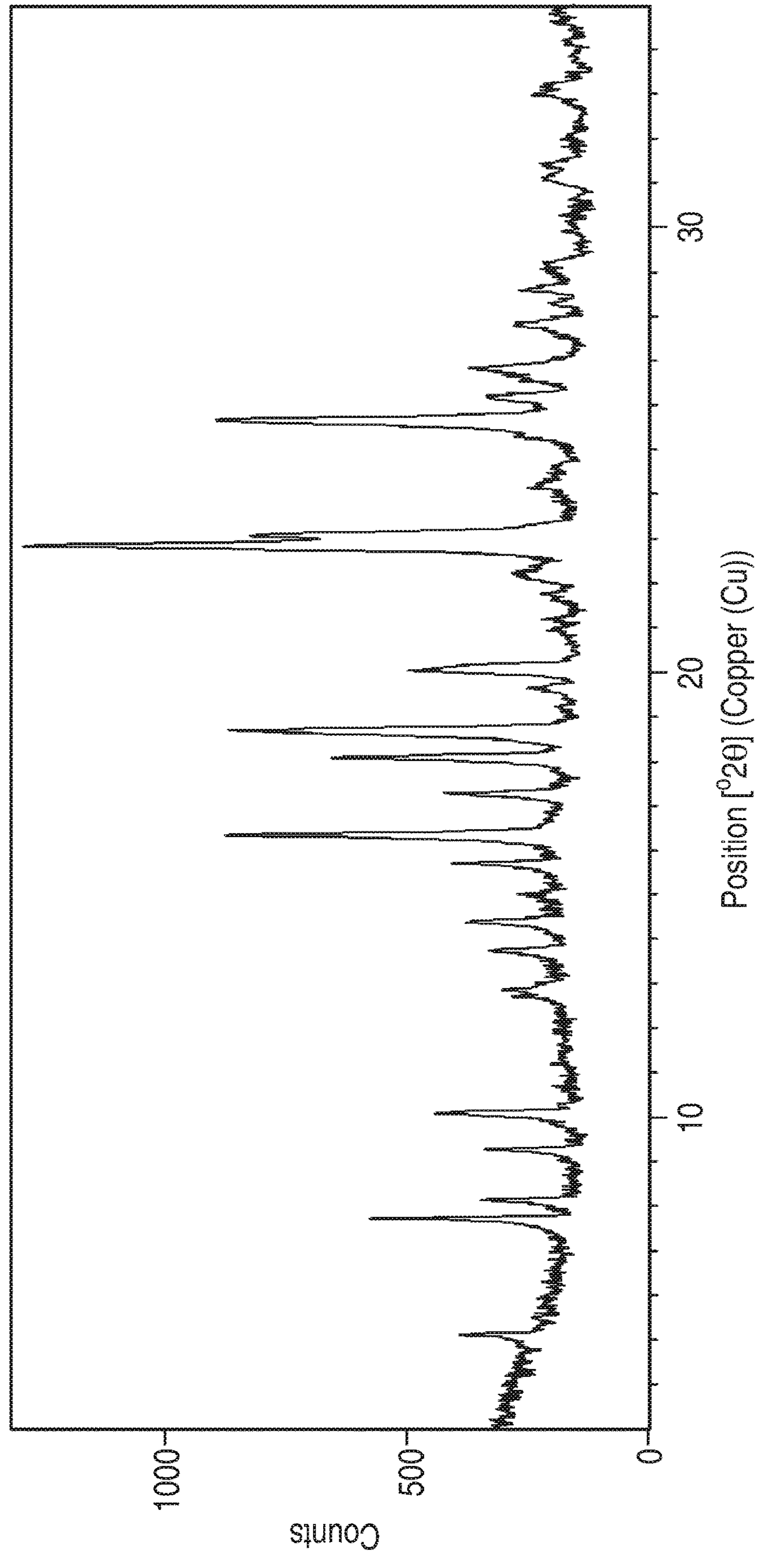

FIG. 5 – Form 5 – XRPD
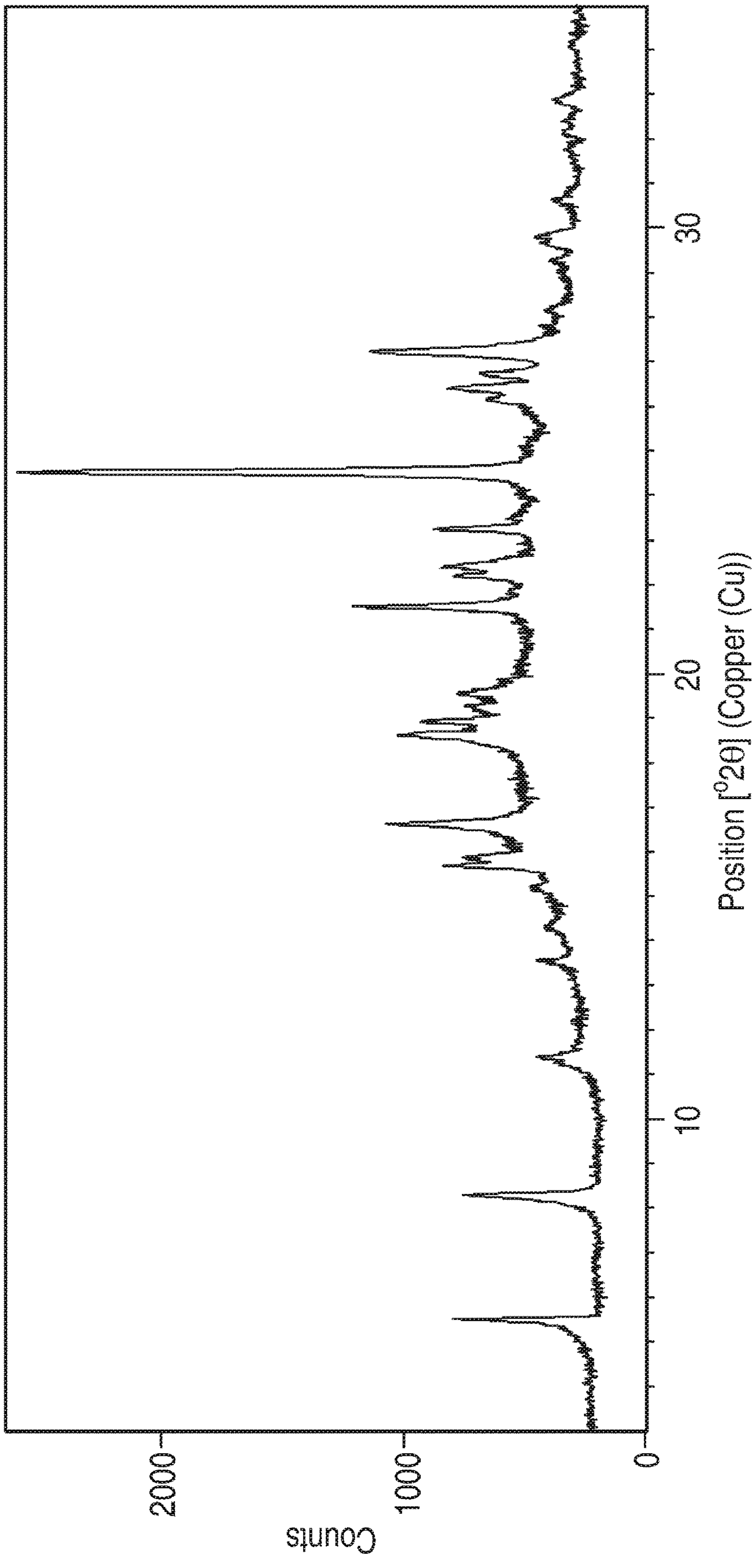

FIG. 6 – Form 6 – XRPD
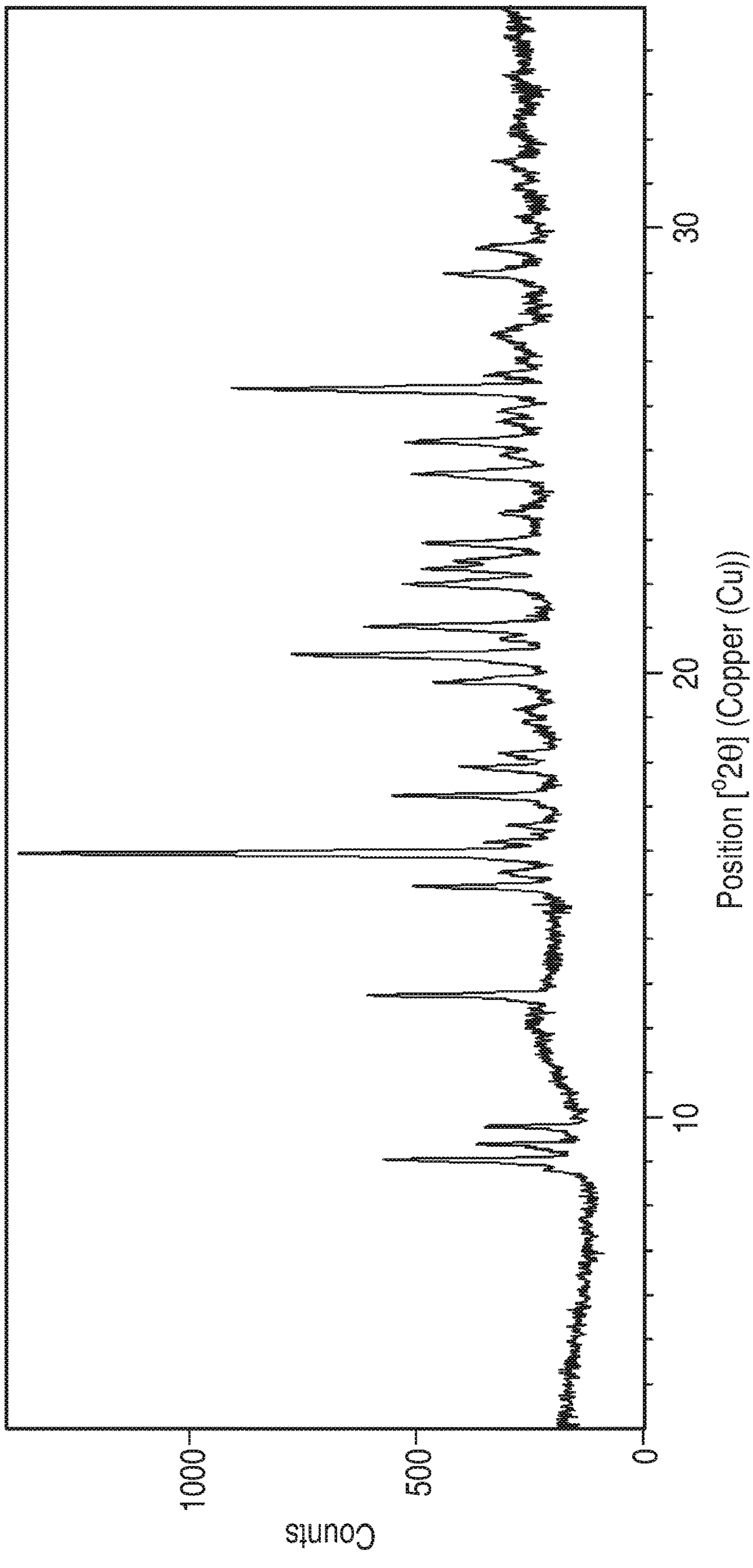

FIG. 7 – Form 7 – XRPD
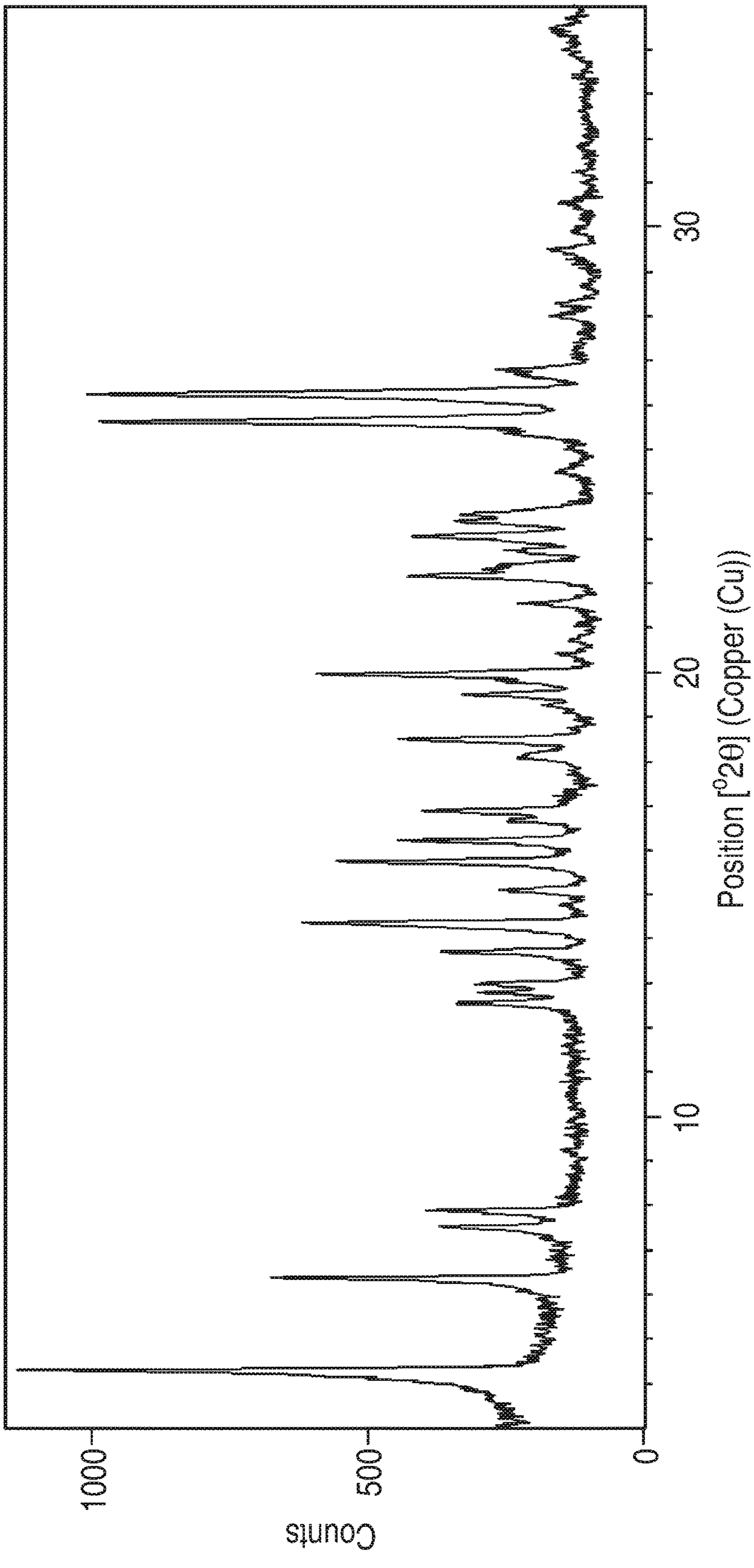

FIG. 8 – Form 8 – XRPD
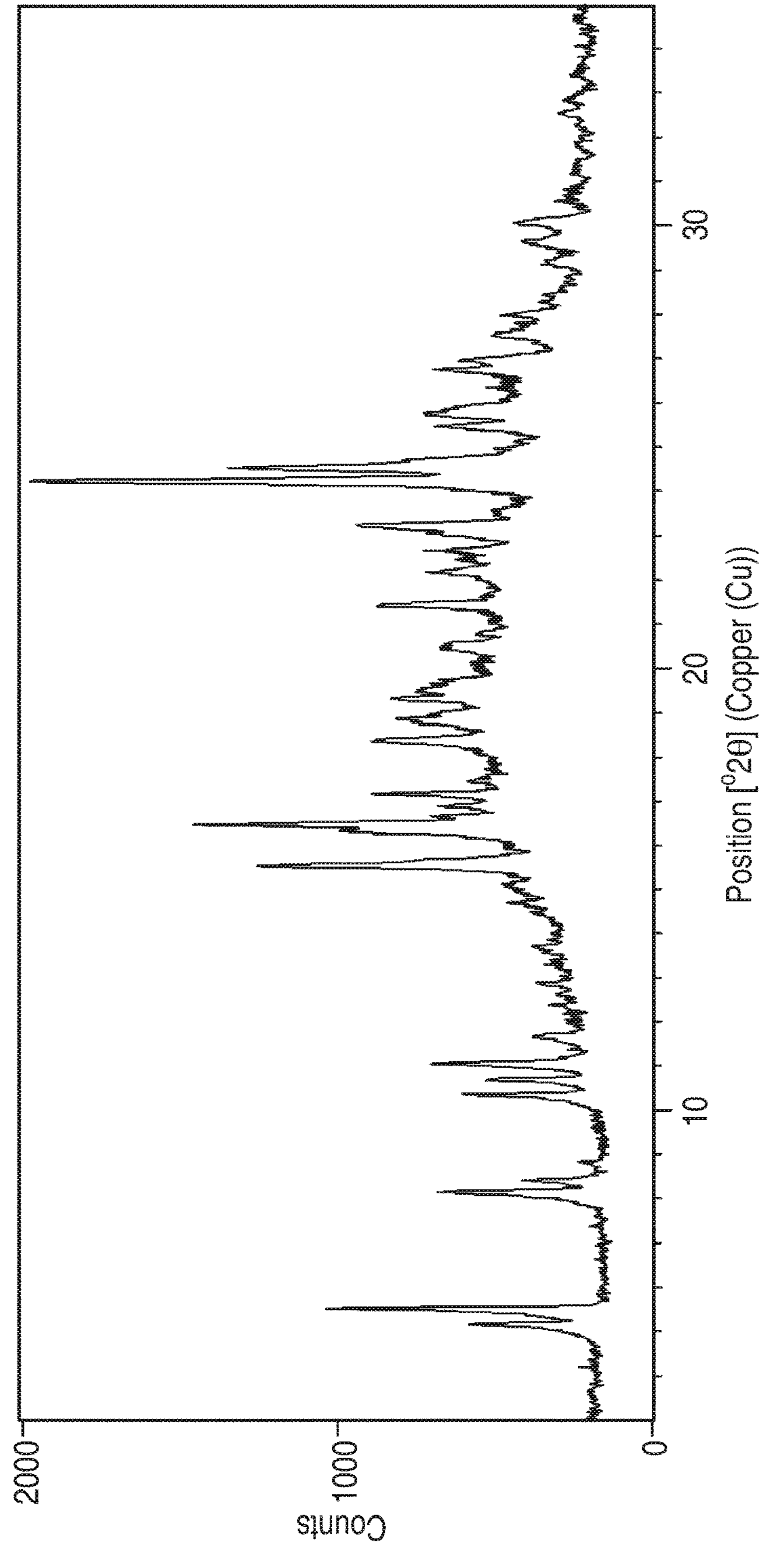

FIG. 9 - Form 1 - XRPD 1, 3, 6, months
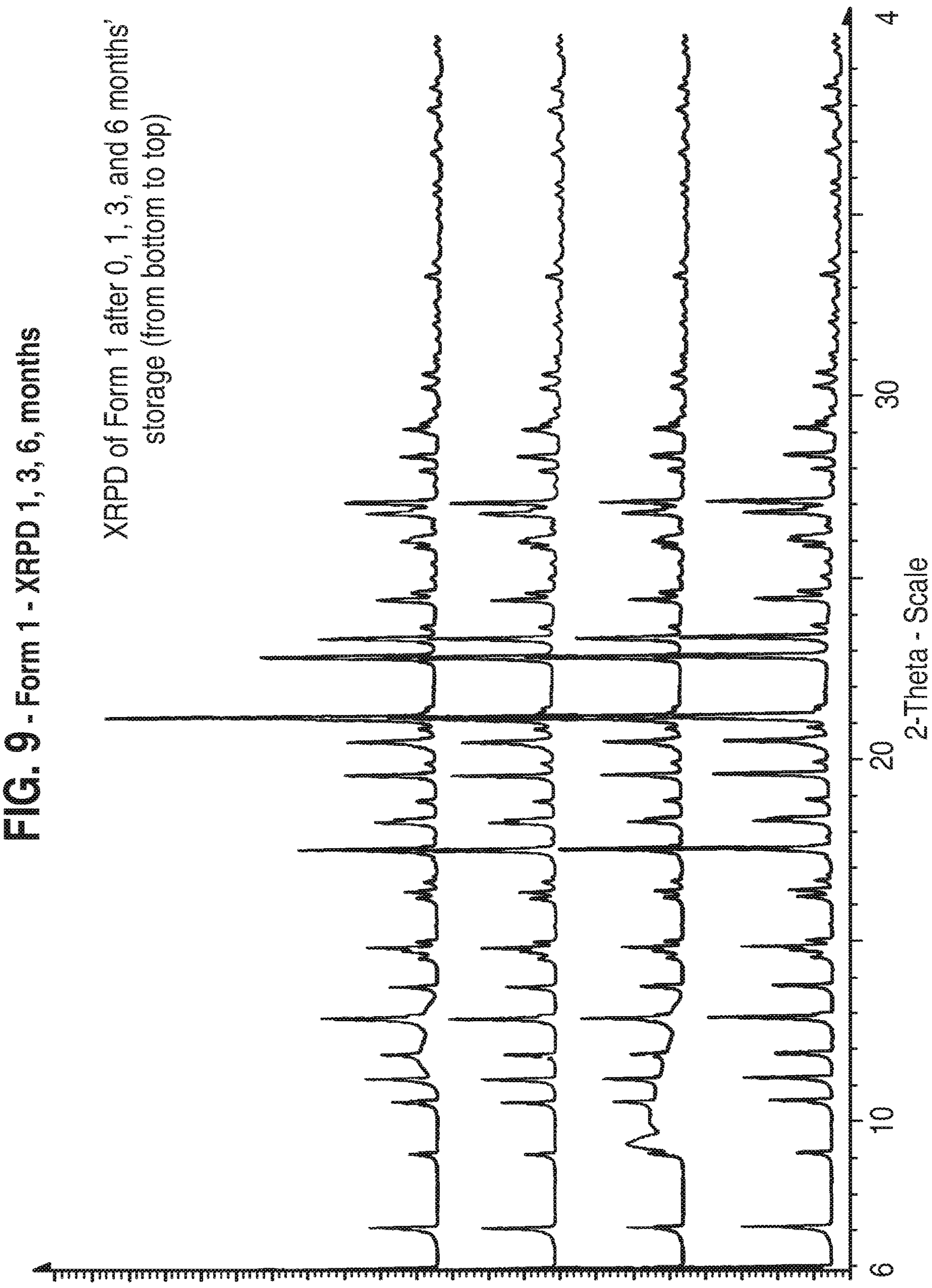

FIG. 10 – lyophile – XRPD
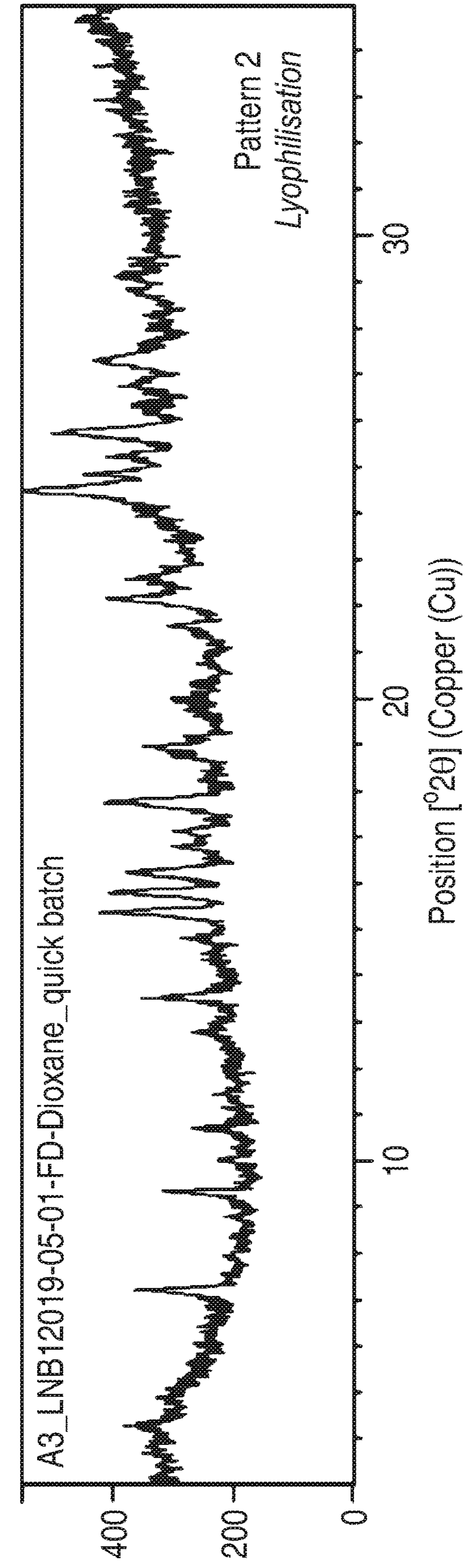

FIG. 11 – Form 1 – DTA - TGA
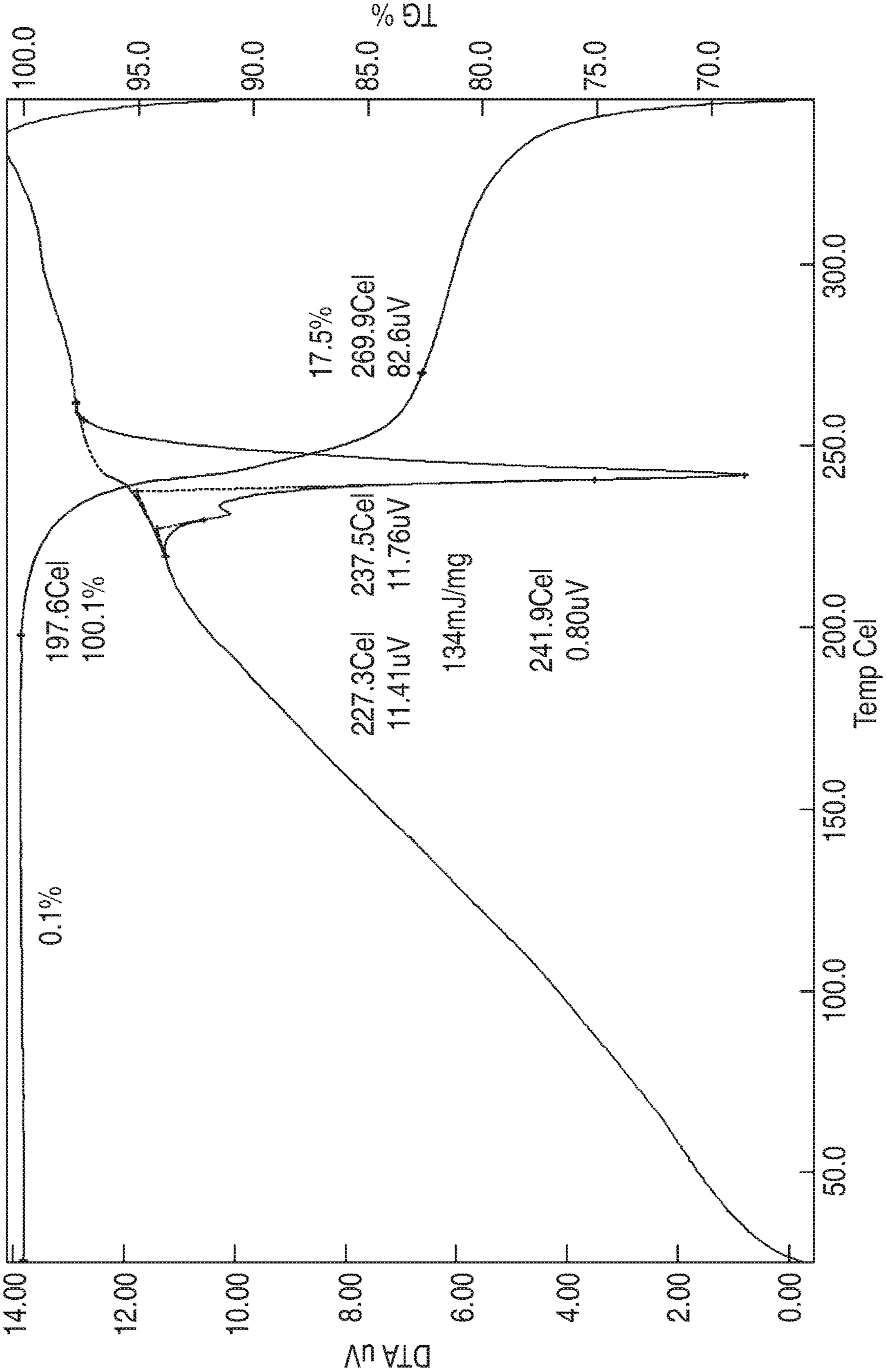

FIG. 12 – Form 2 – DTA - TGA
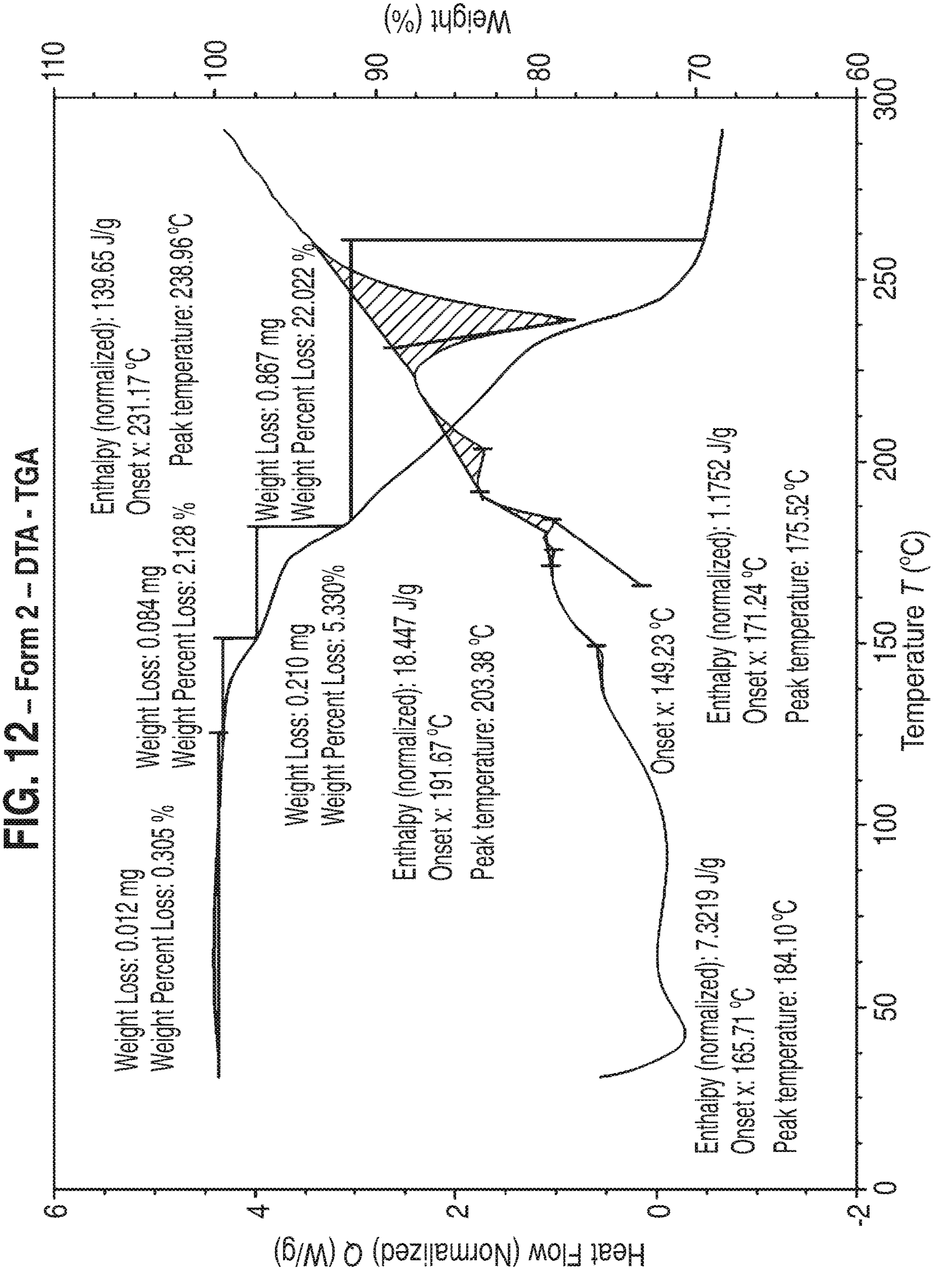

FIG. 13 – Form 3 – DTA - TGA
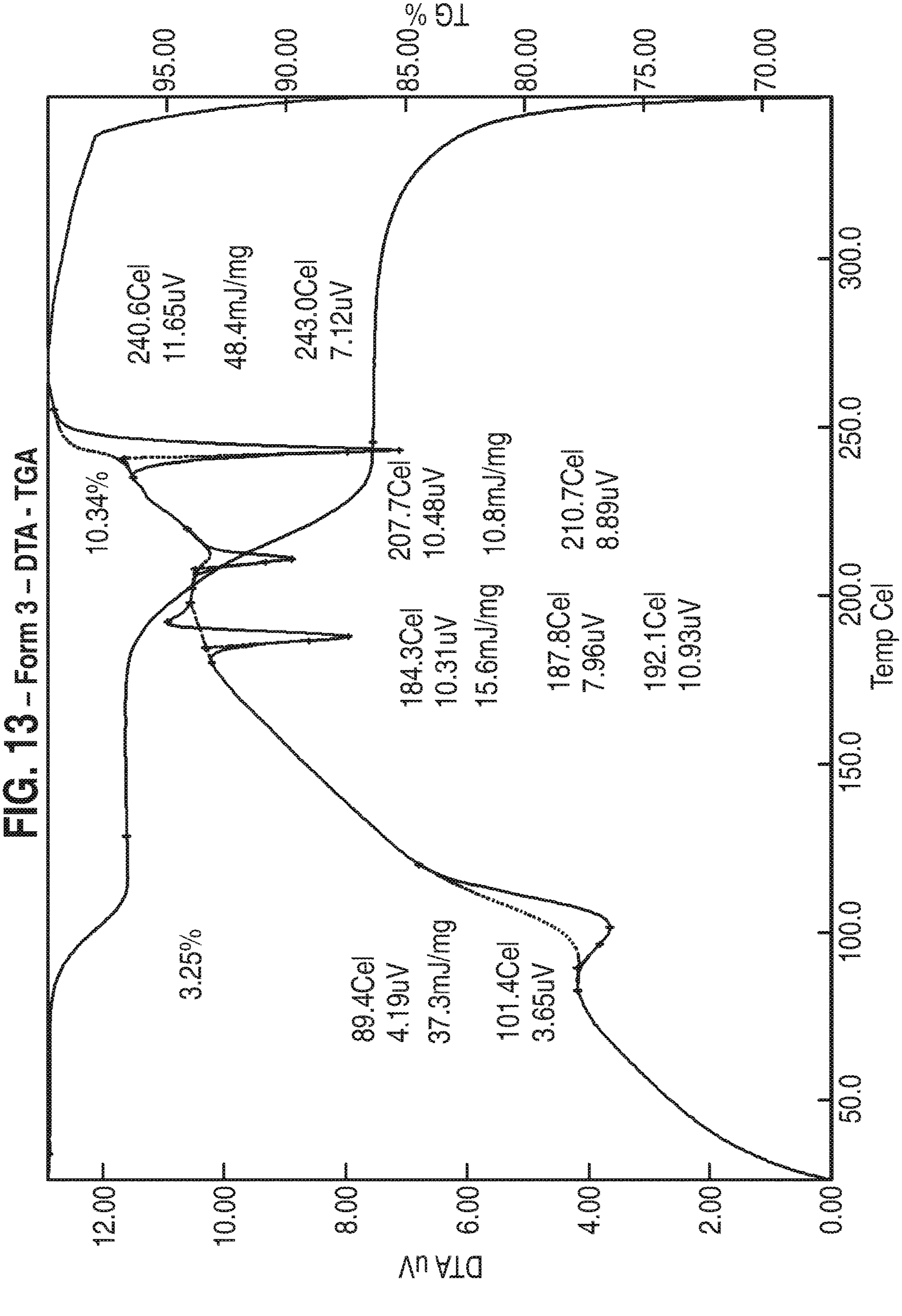

FIG. 14 – Form 4 – DTA - TGA
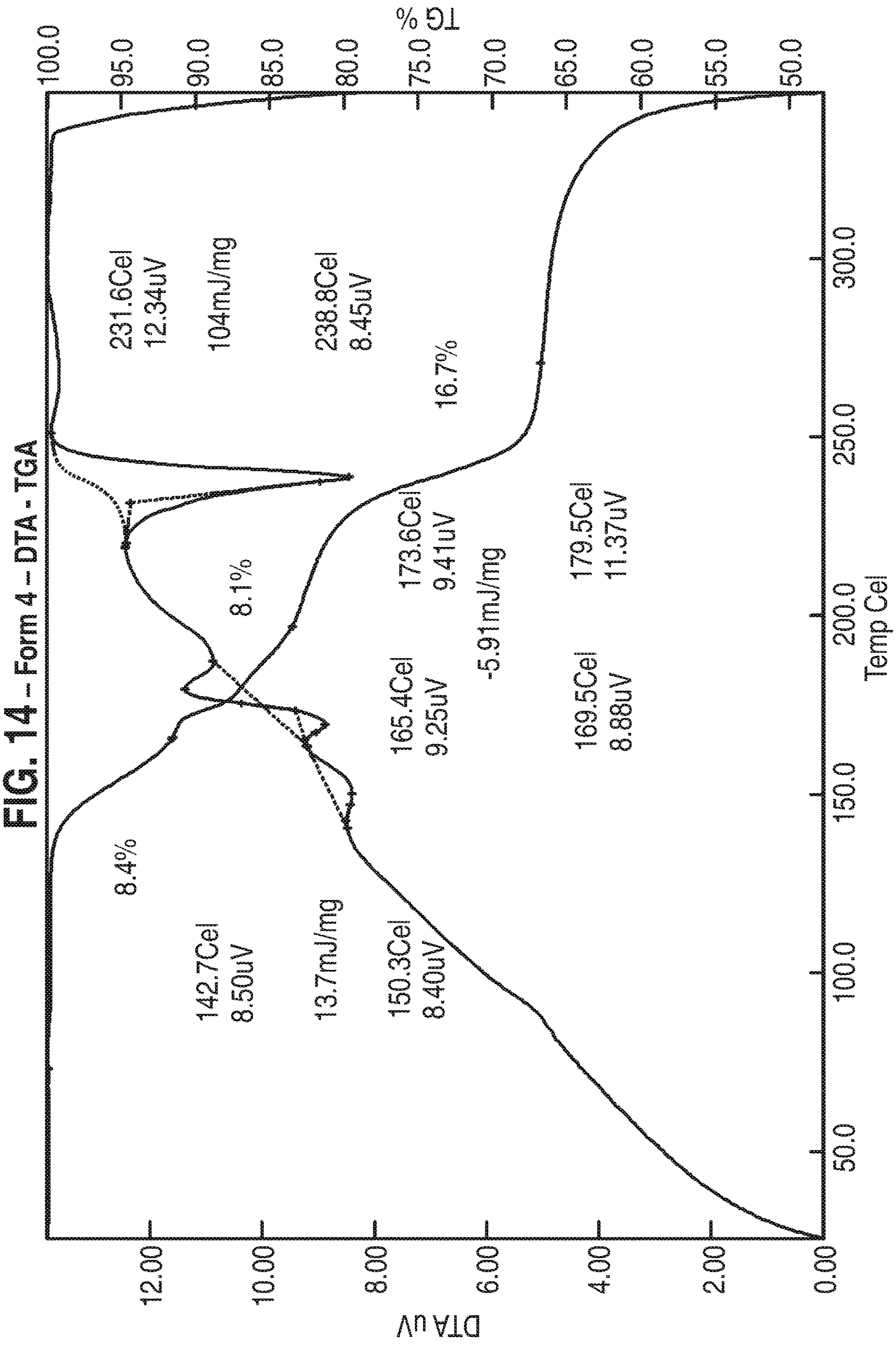

FIG. 15 – Form 5 – DTA - TGA
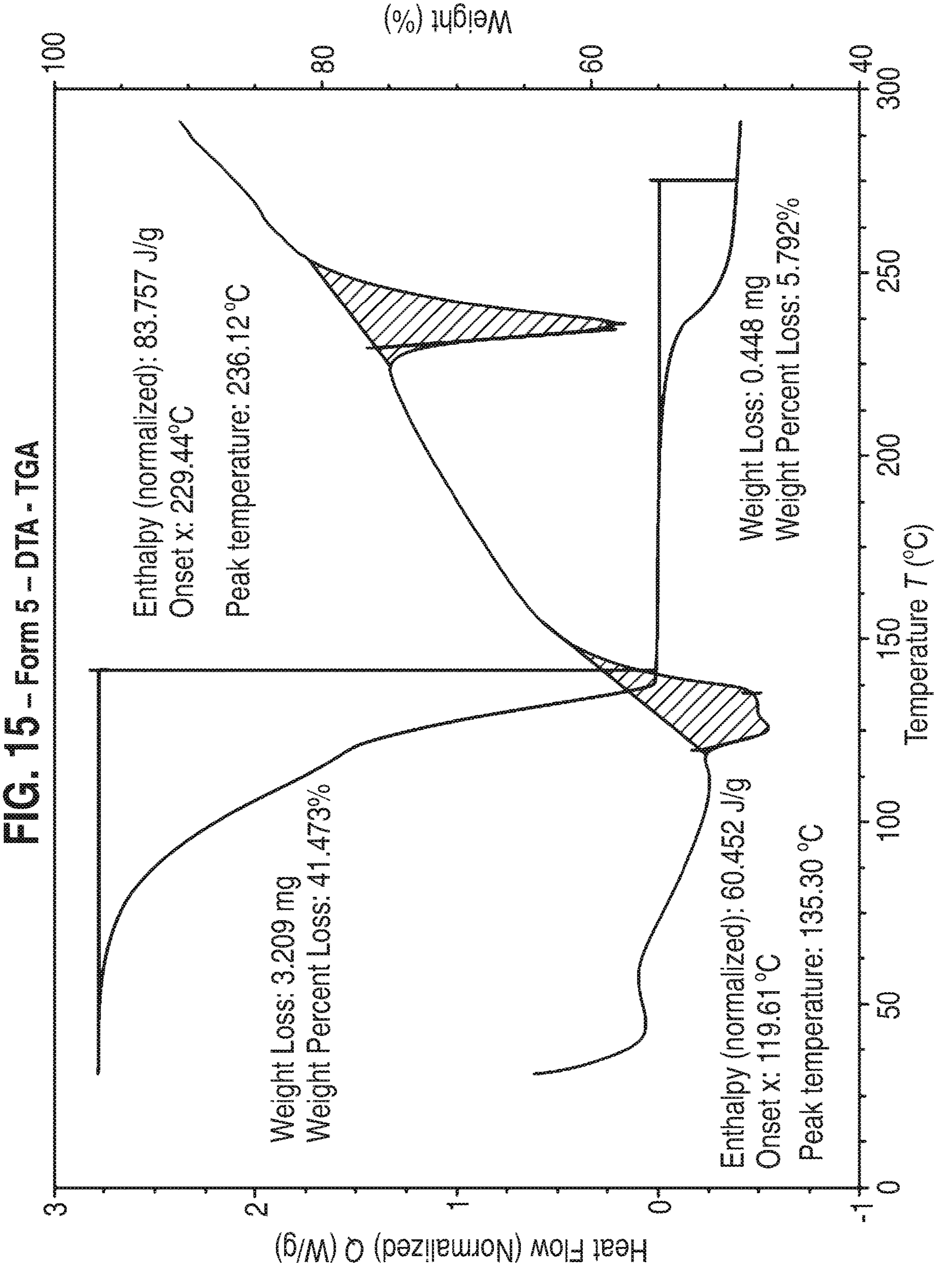

FIG. 16 – Form 7 – DTA - TGA
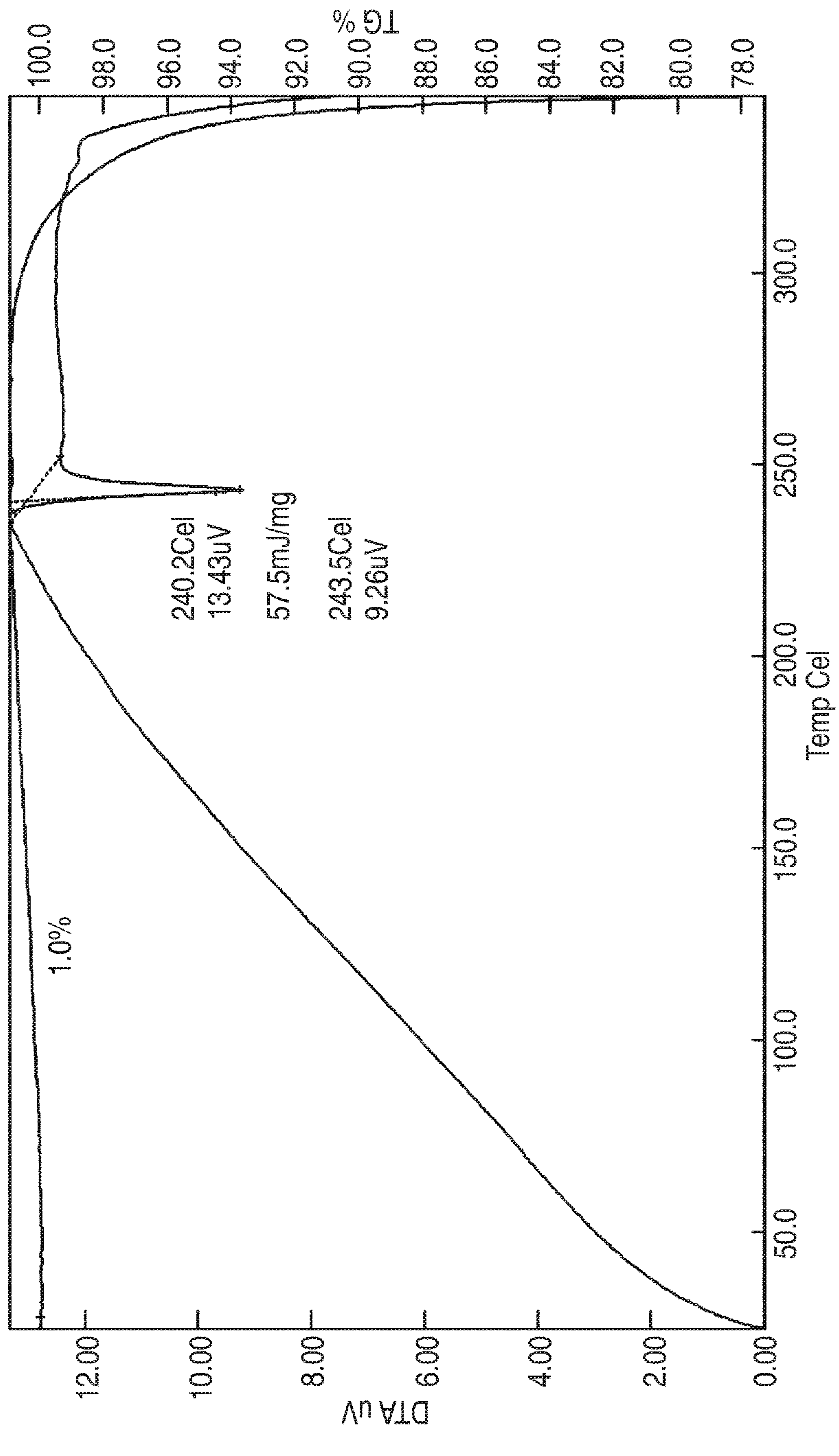

FIG. 17 – Form 8 – DTA - TGA
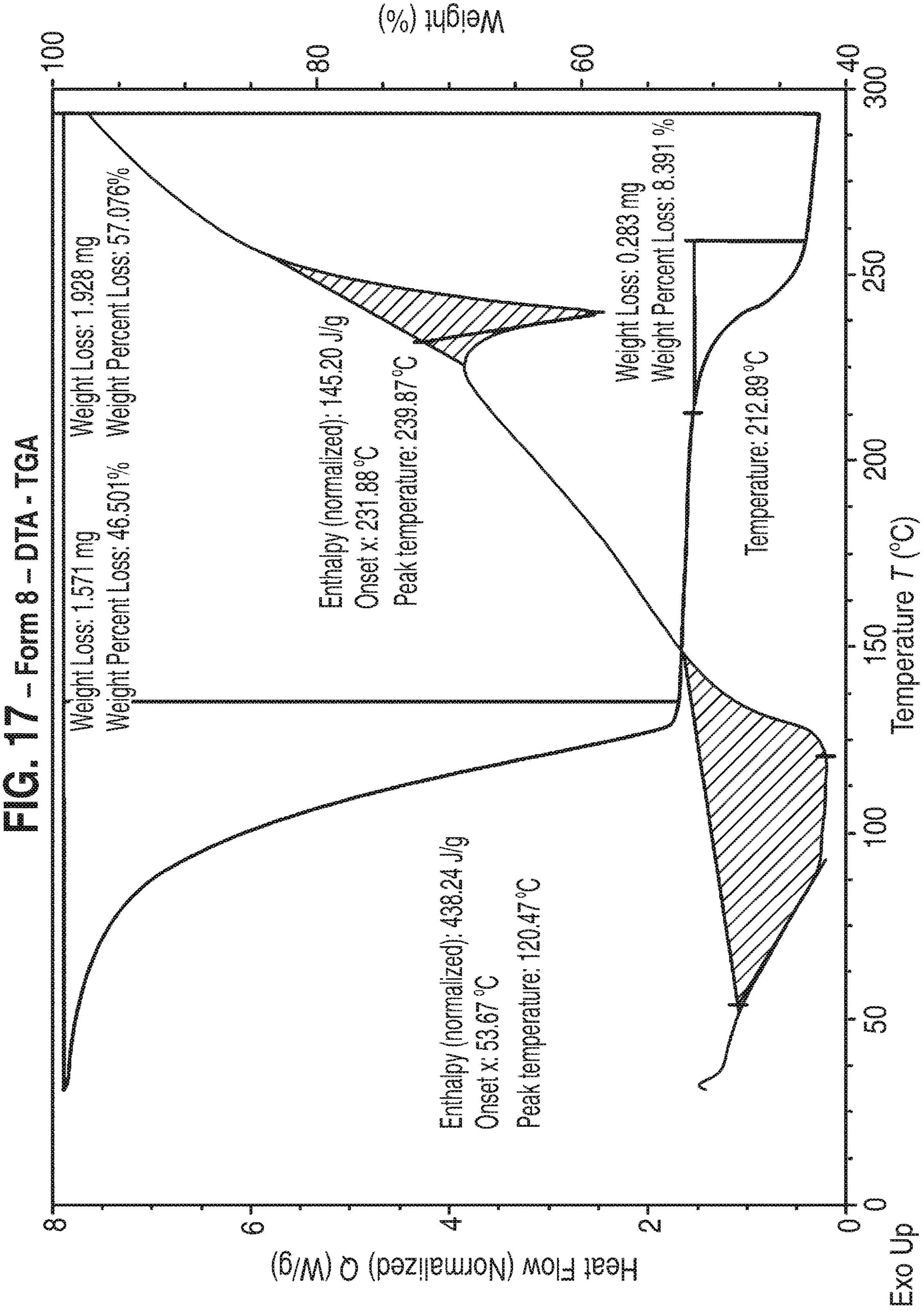

FIG. 18 – Form 1 – DSC
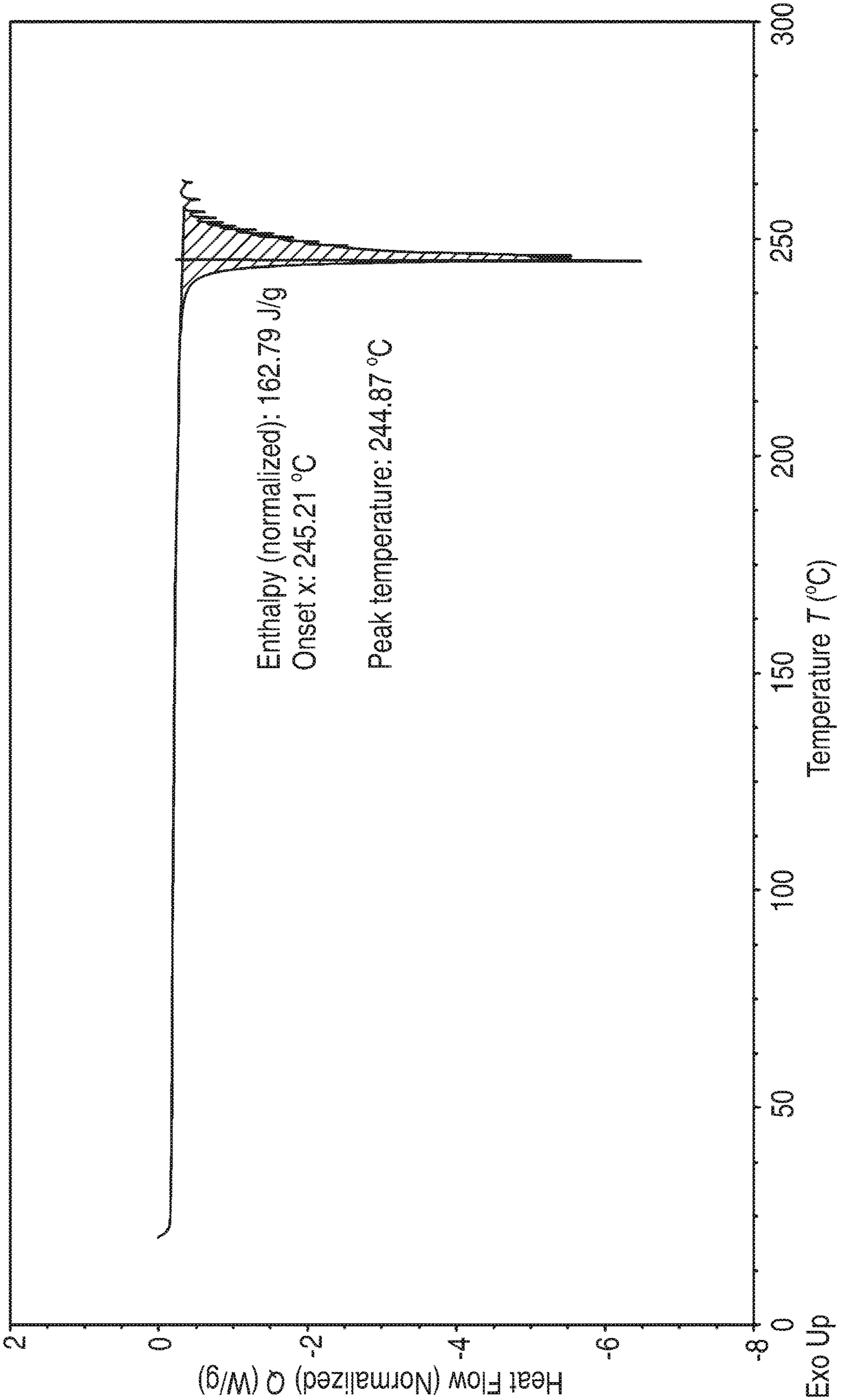

FIG. 19 – Form 3 – DSC
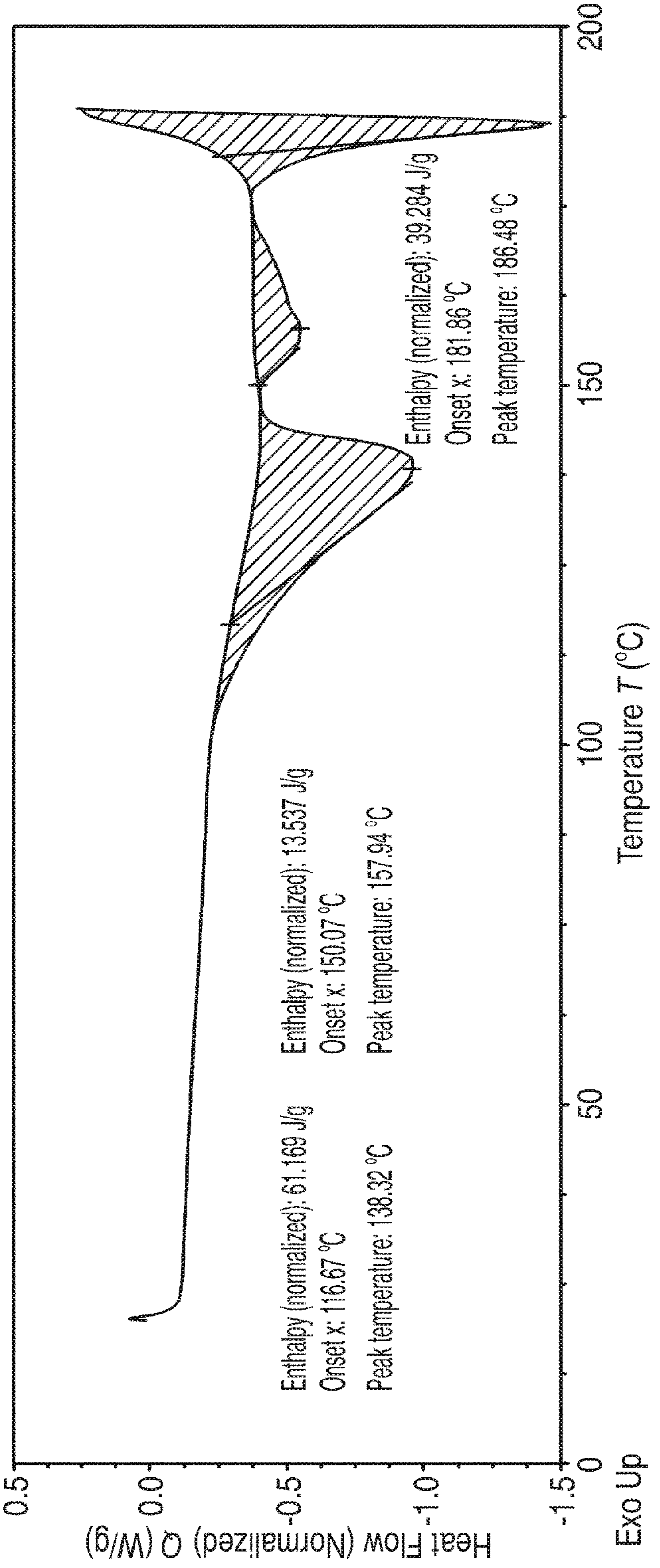

FIG. 20 – Form 7 – DSC
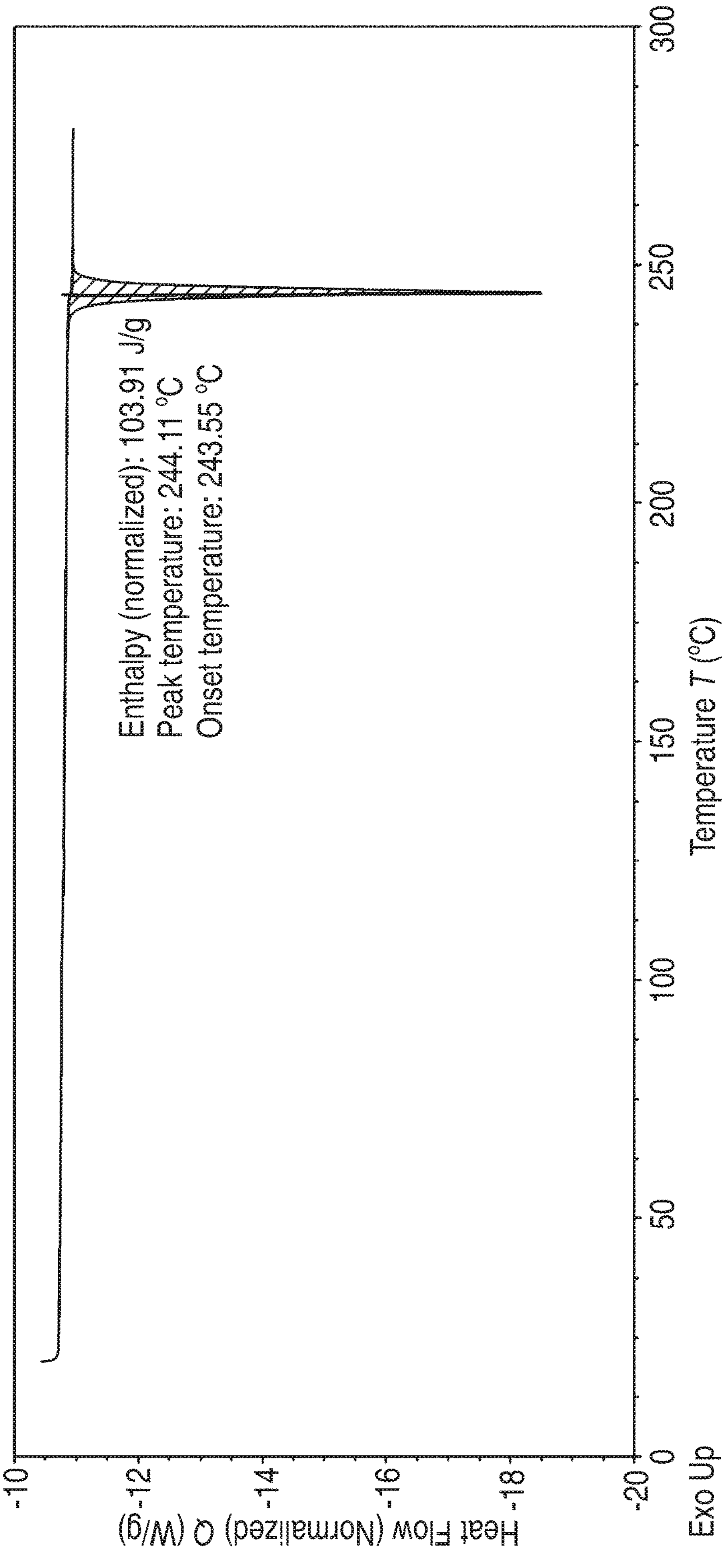

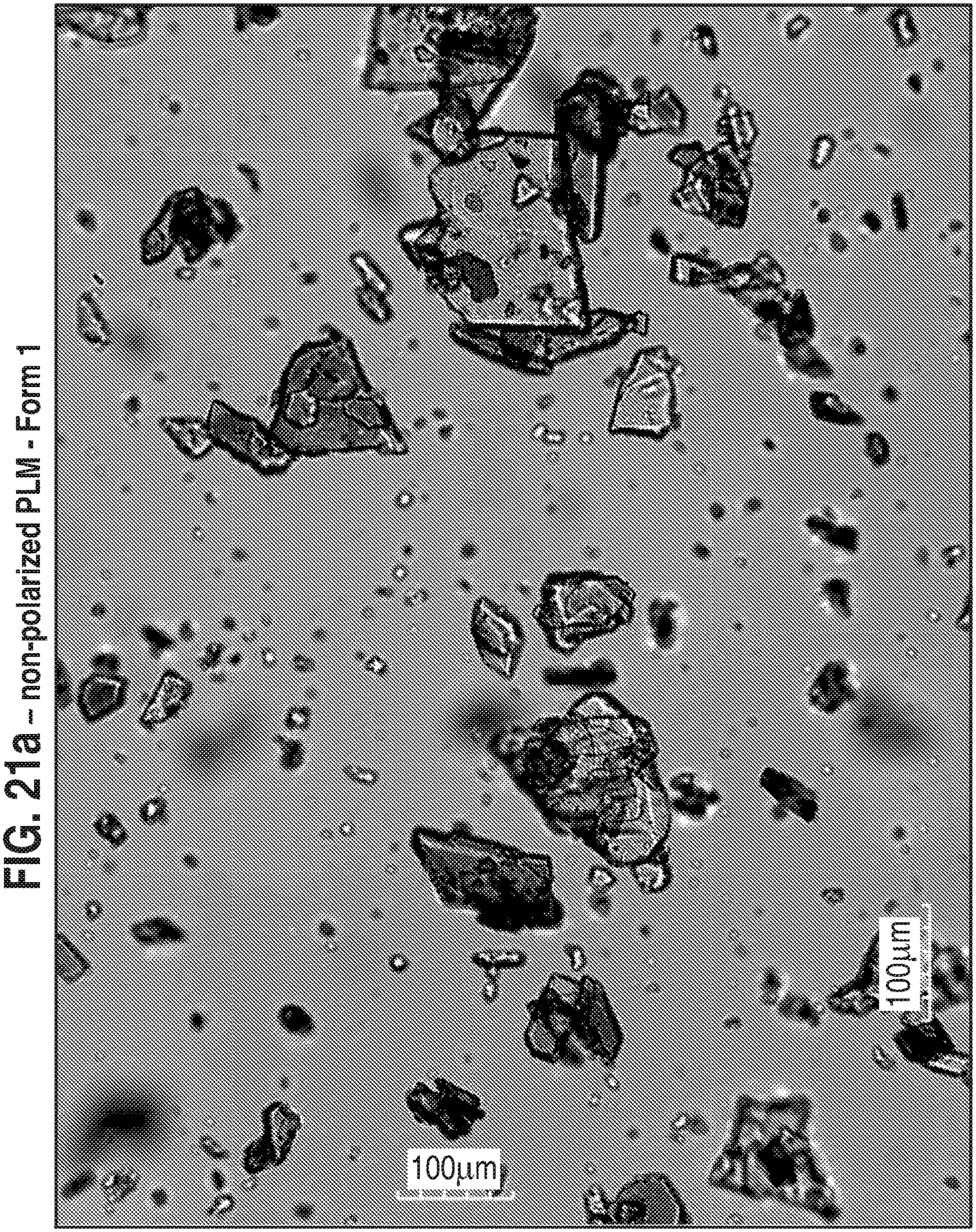
FIG. 21a – non-polarized PLM - Form 1

FIG. 21b – polarized PLM - Form 1
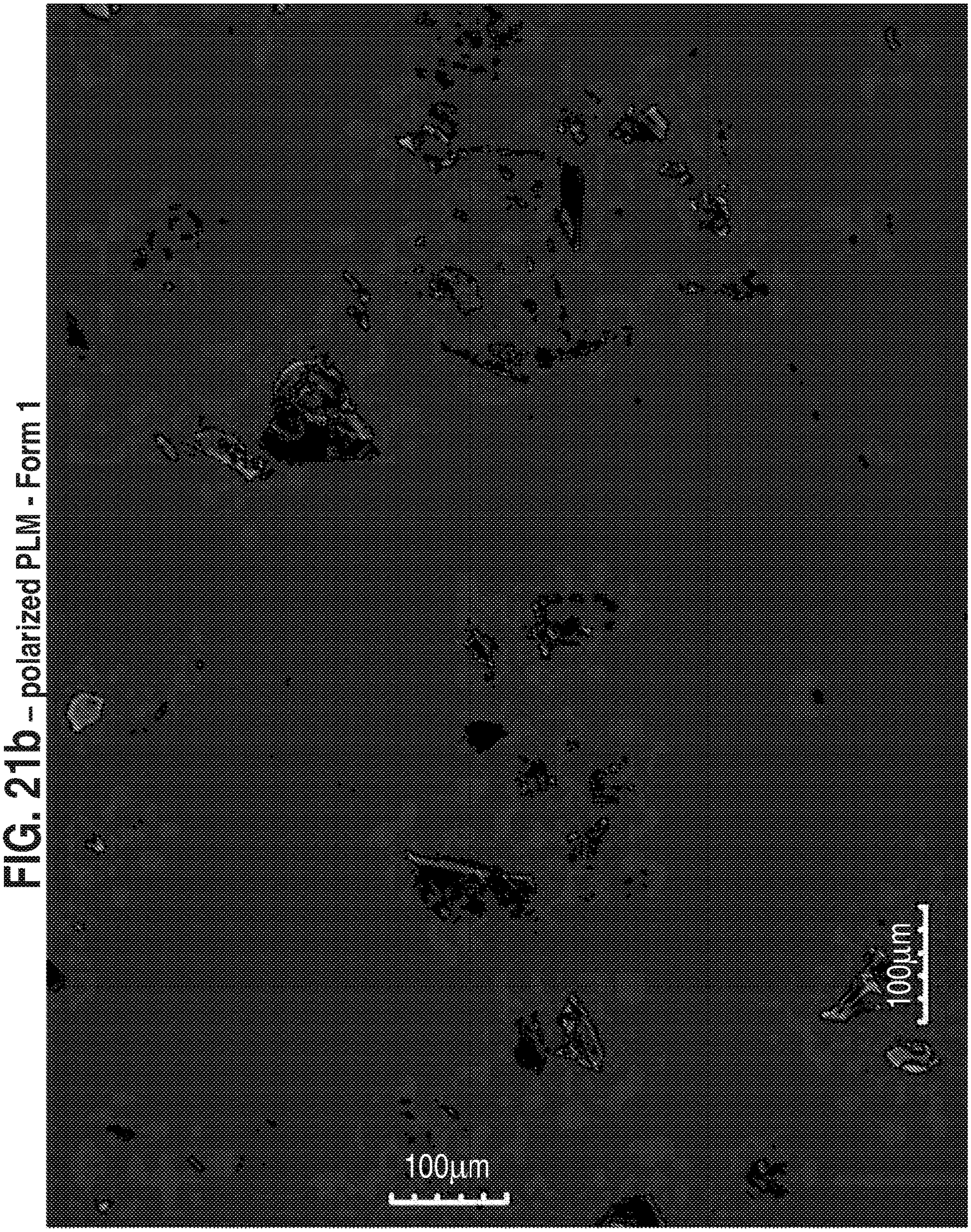

FIG. 22a – non-polarized PLM - Form 2
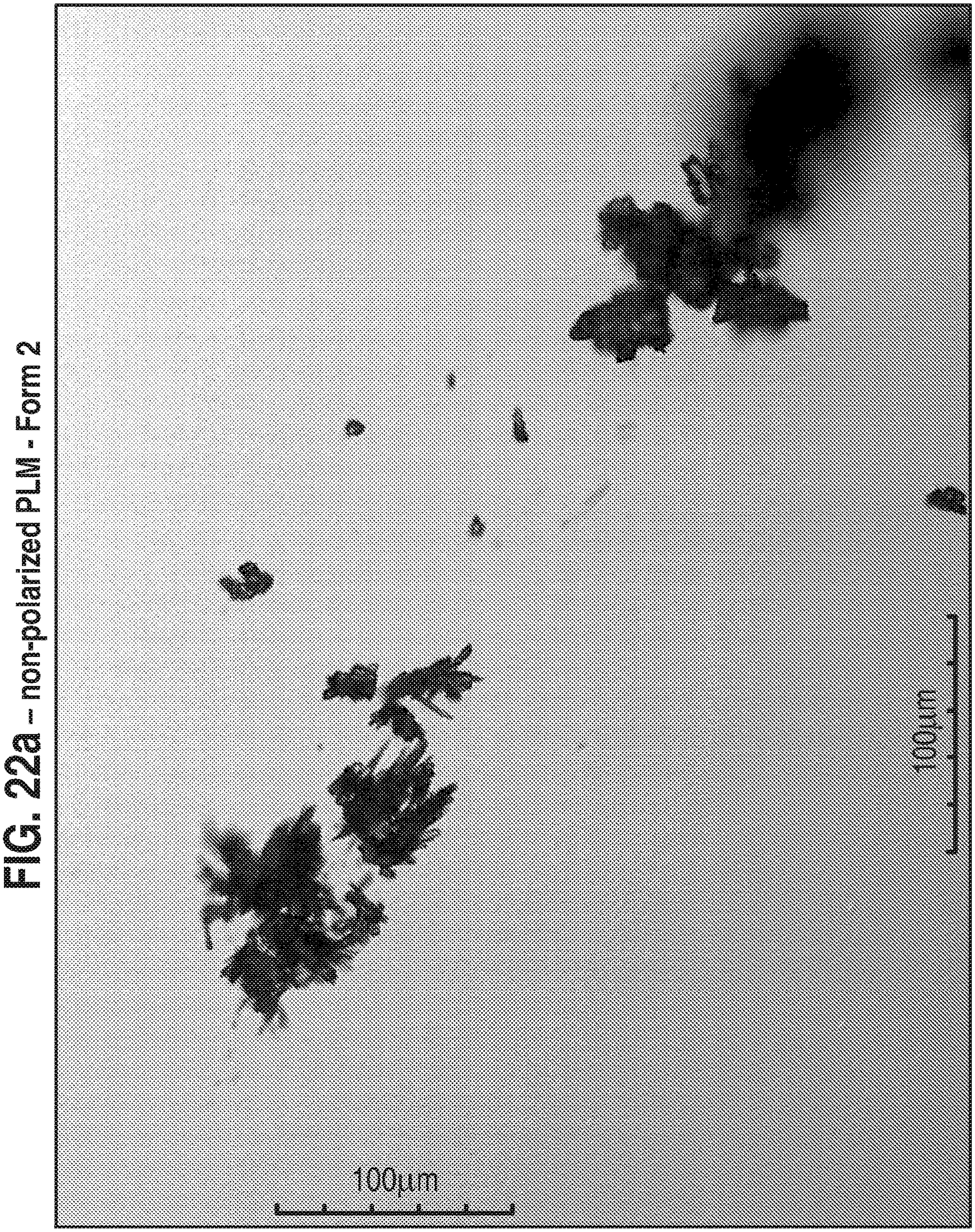

FIG. 22b – polarized PLM - Form 2
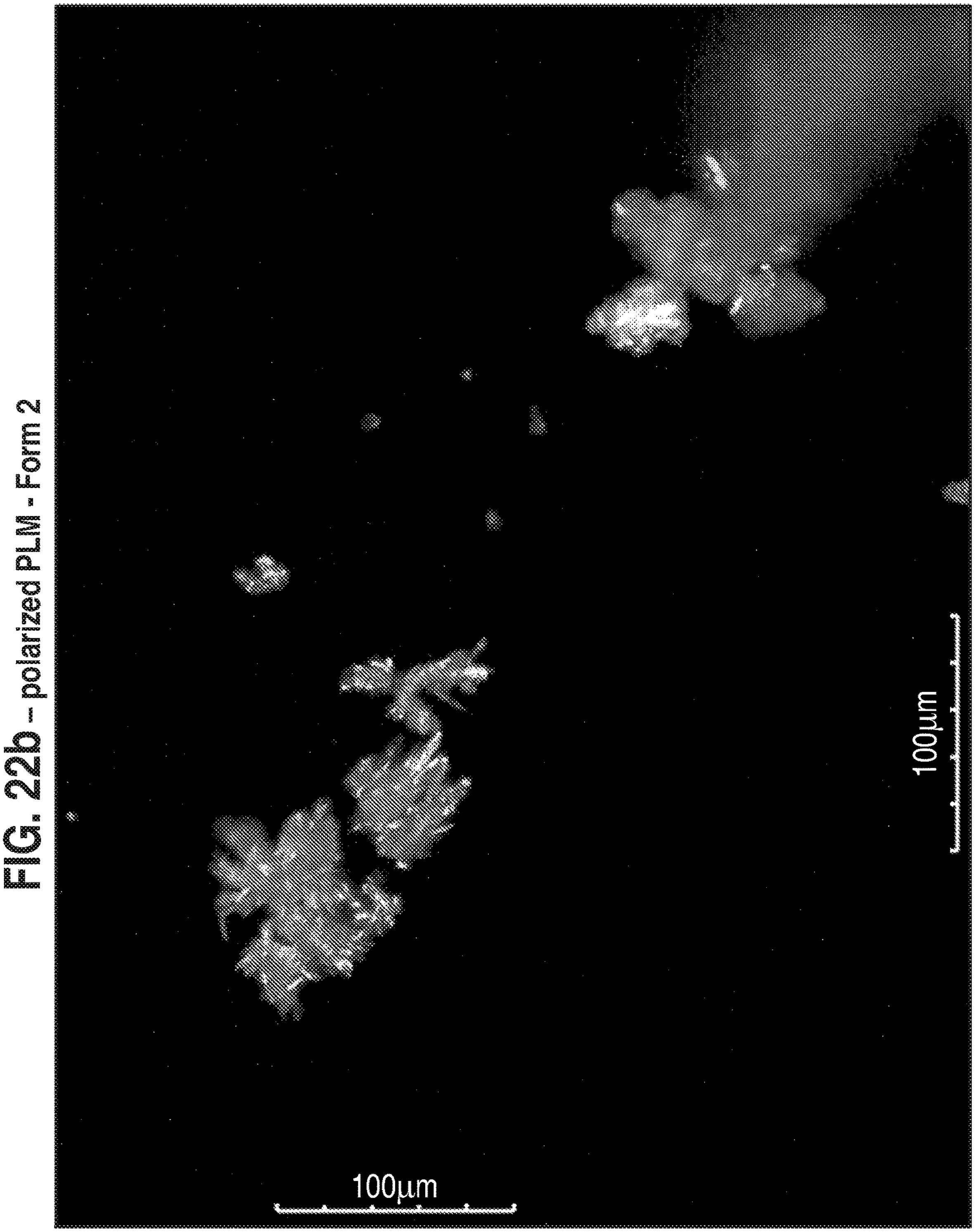

FIG. 23a – non-polarized PLM - Form 3
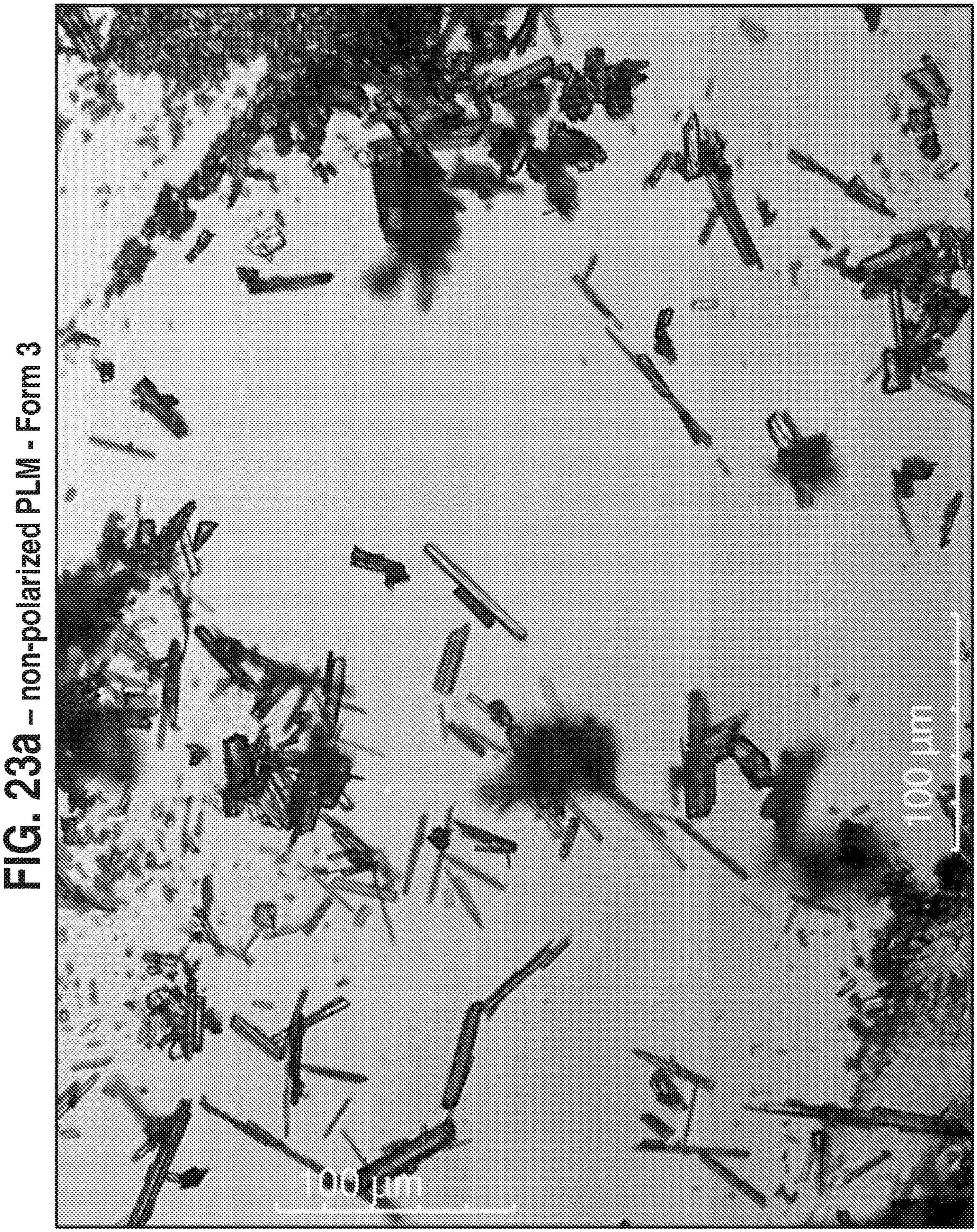

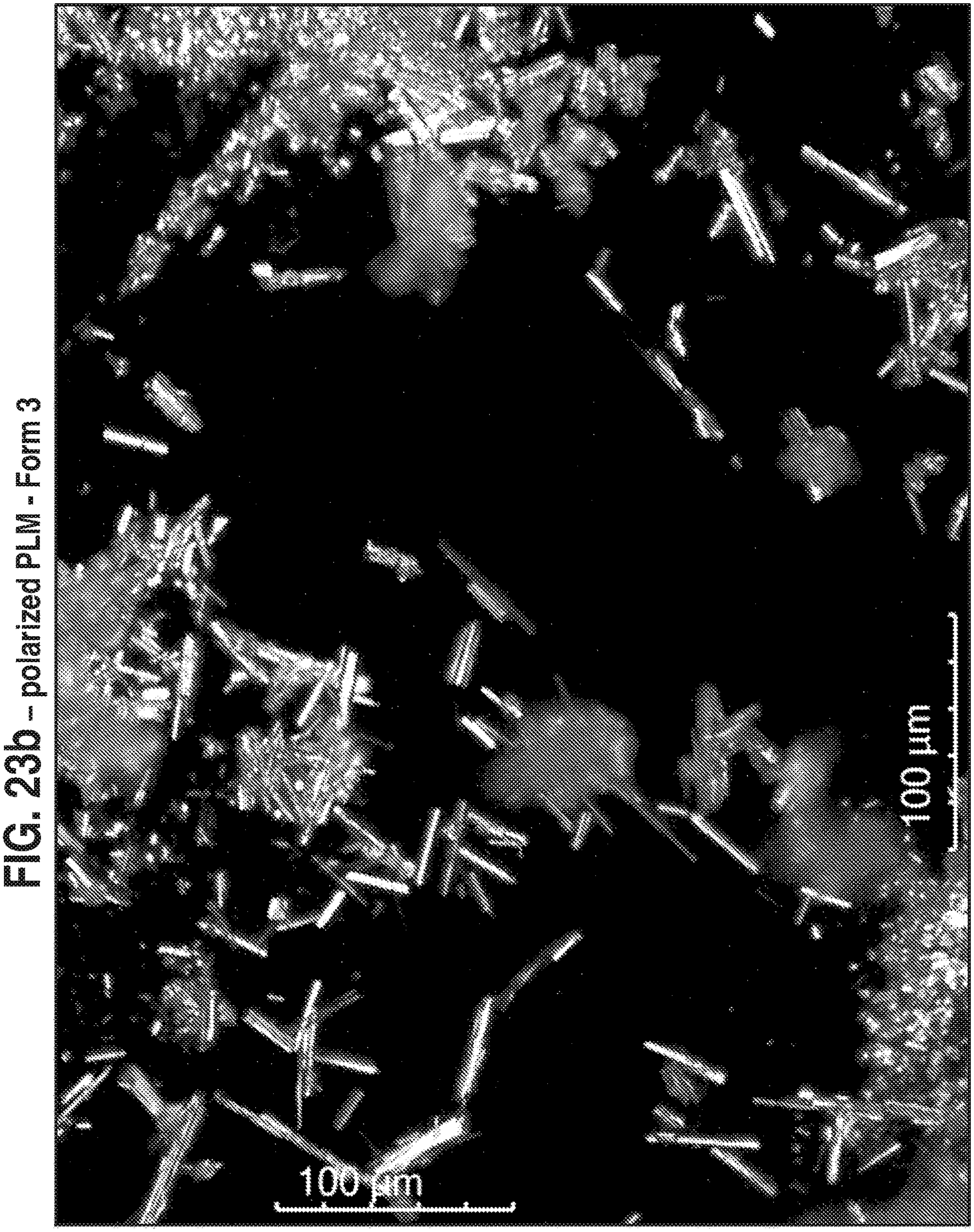
FIG. 23b – polarized PLM - Form 3

FIG. 24a – non-polarized PLM - Form 4
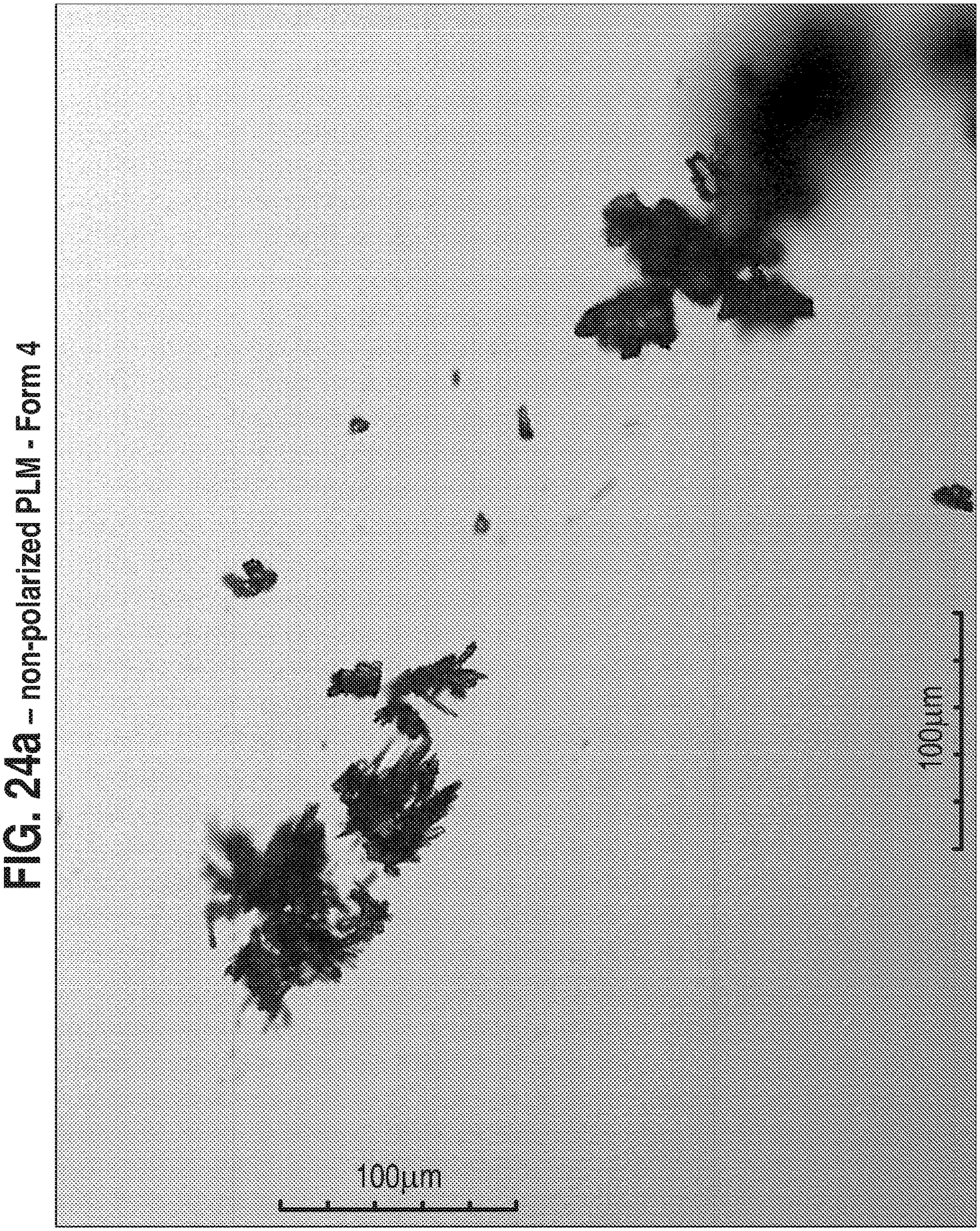

FIG. 24b – polarized PLM - Form 4
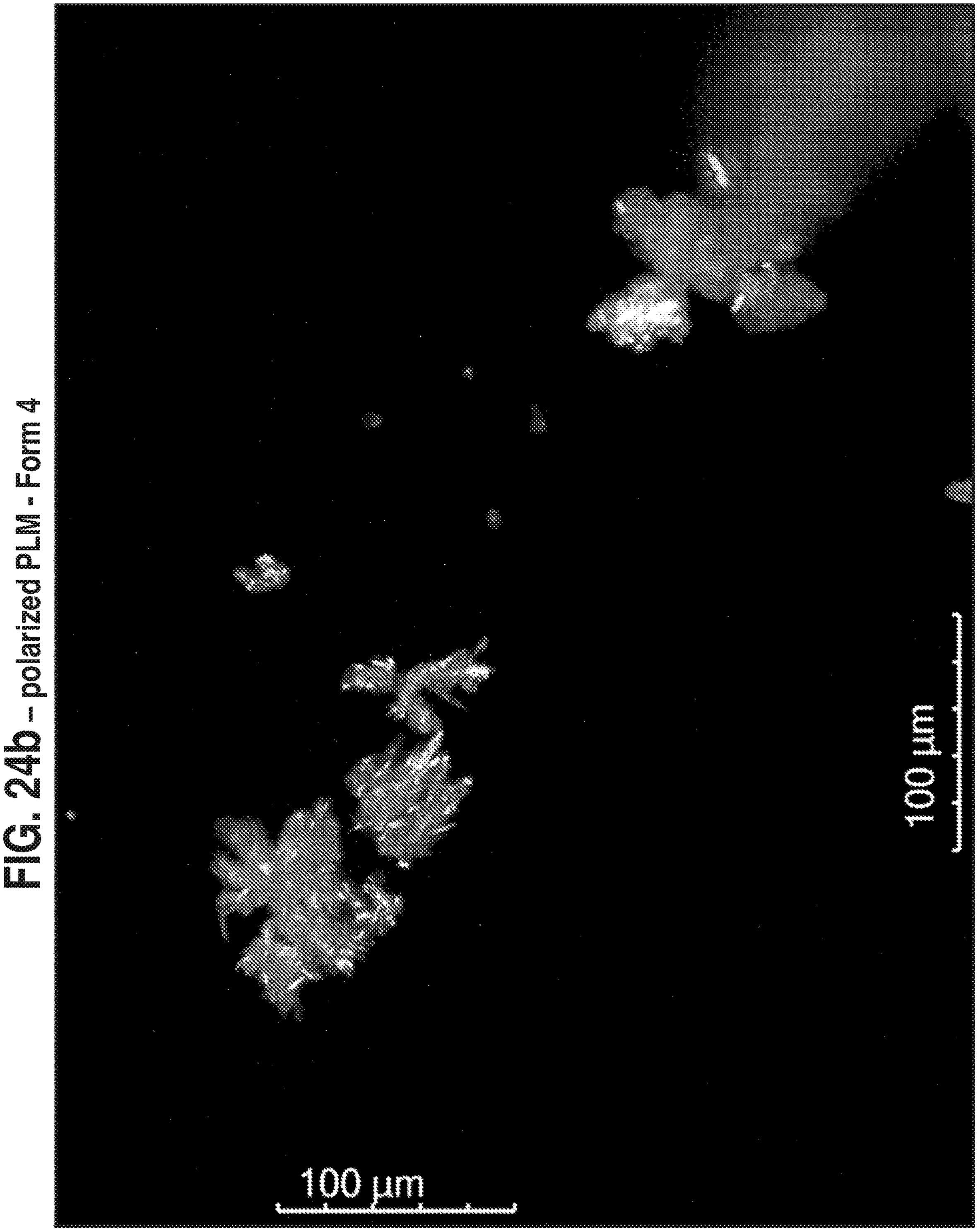

FIG. 25a – non-polarized PLM - Form 5
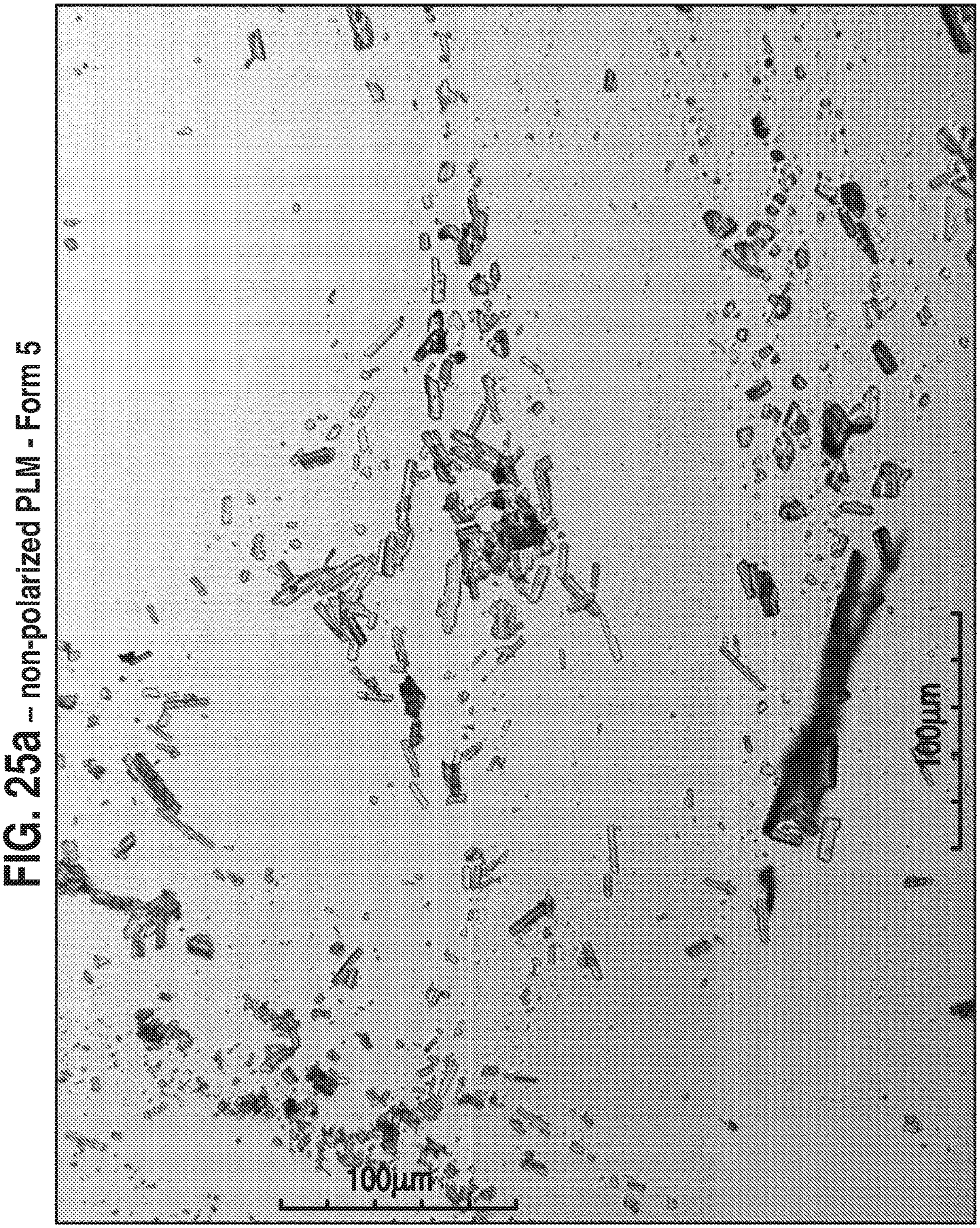

FIG. 25b – polarized PLM - Form 5
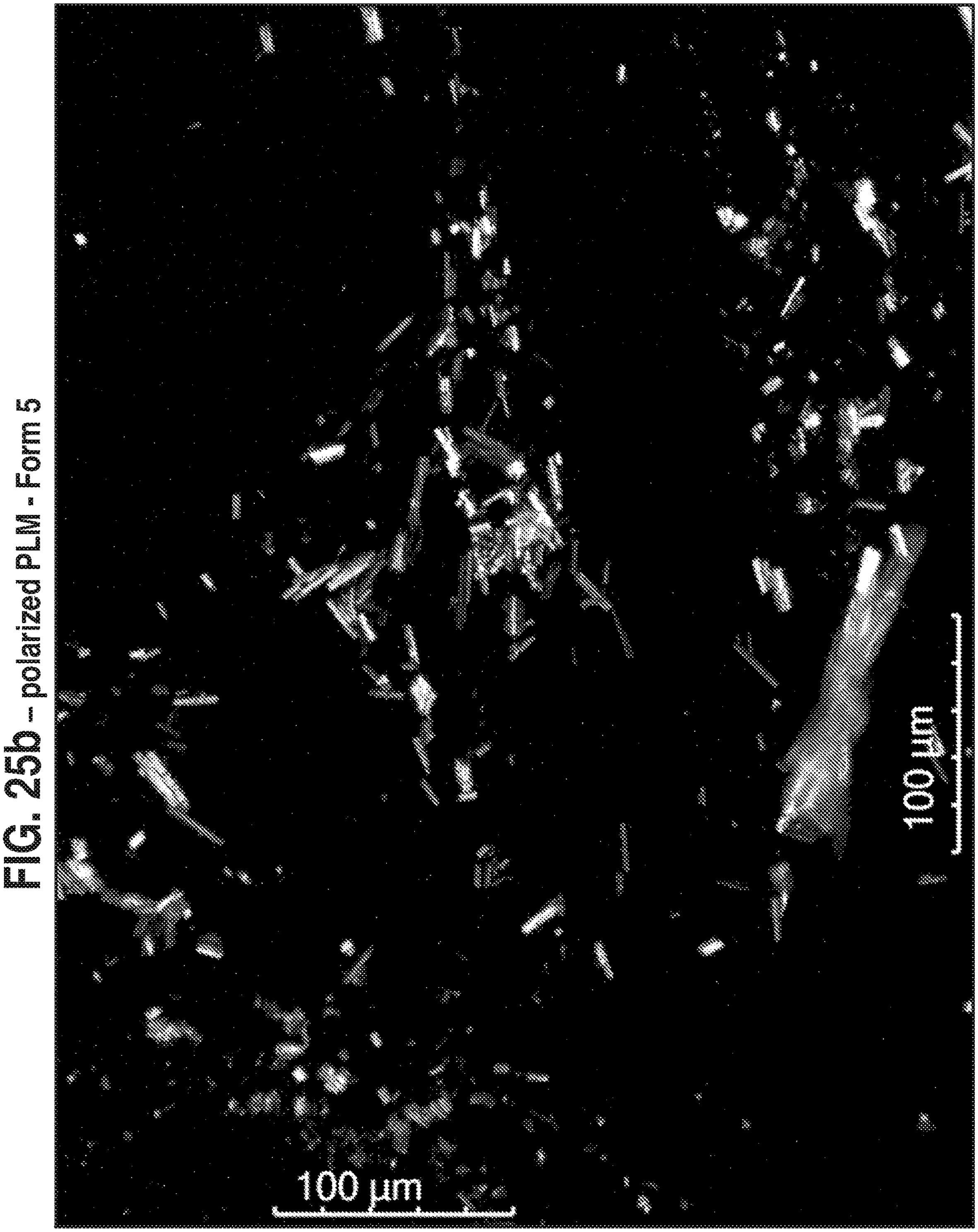

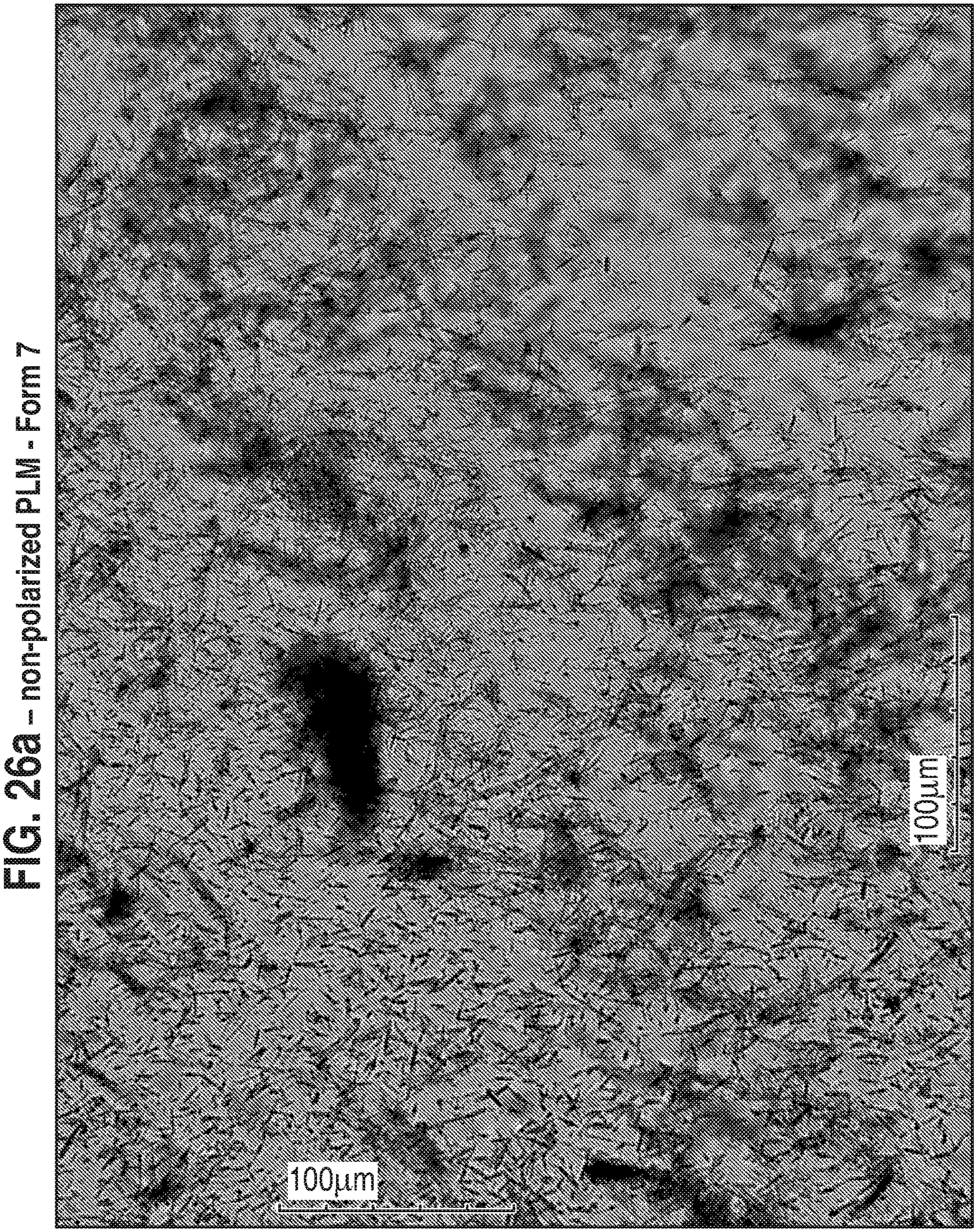
FIG. 26a – non-polarized PLM - Form 7

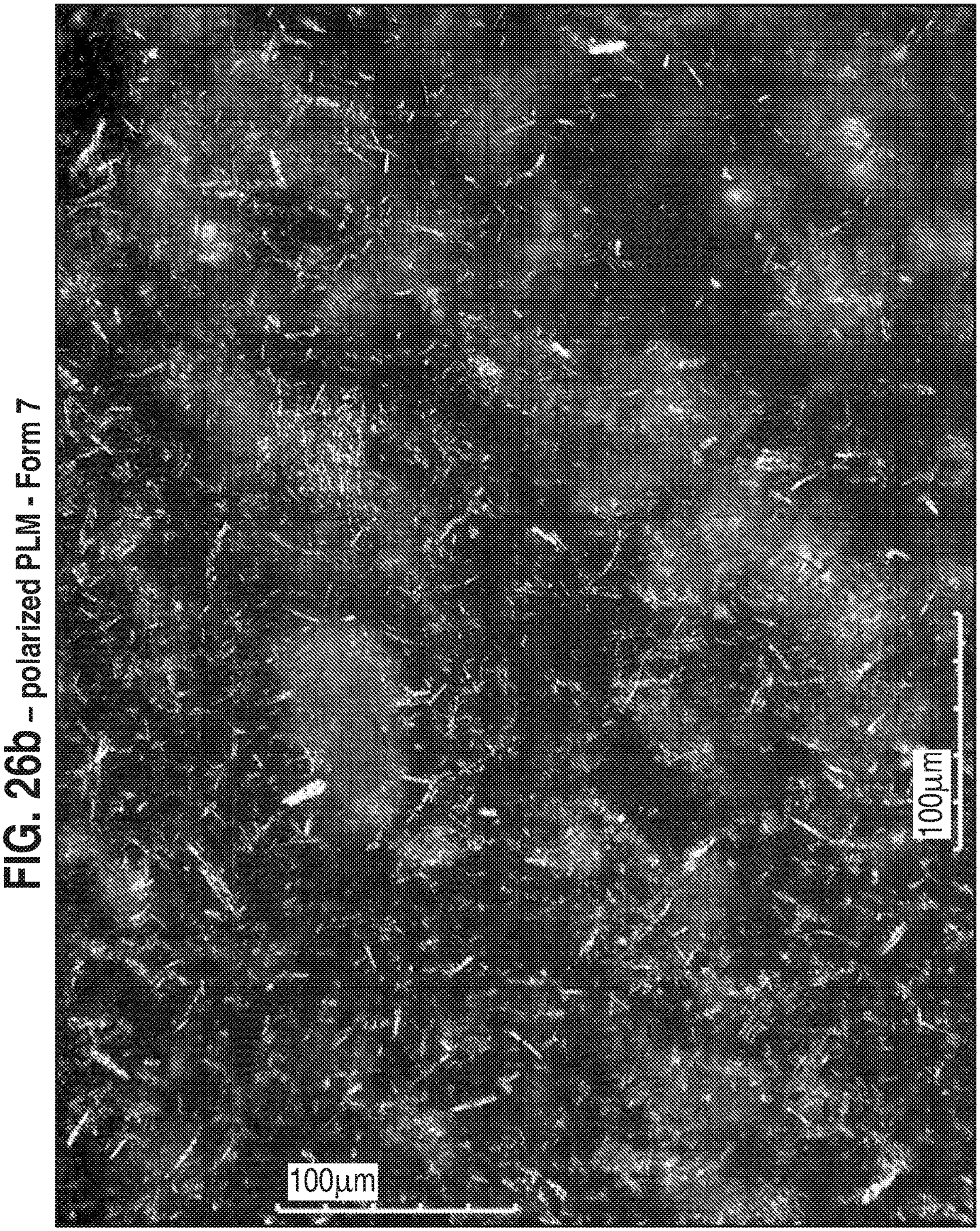
FIG. 26b – polarized PLM - Form 7

FIG. 27a – non-polarized PLM - Form 8
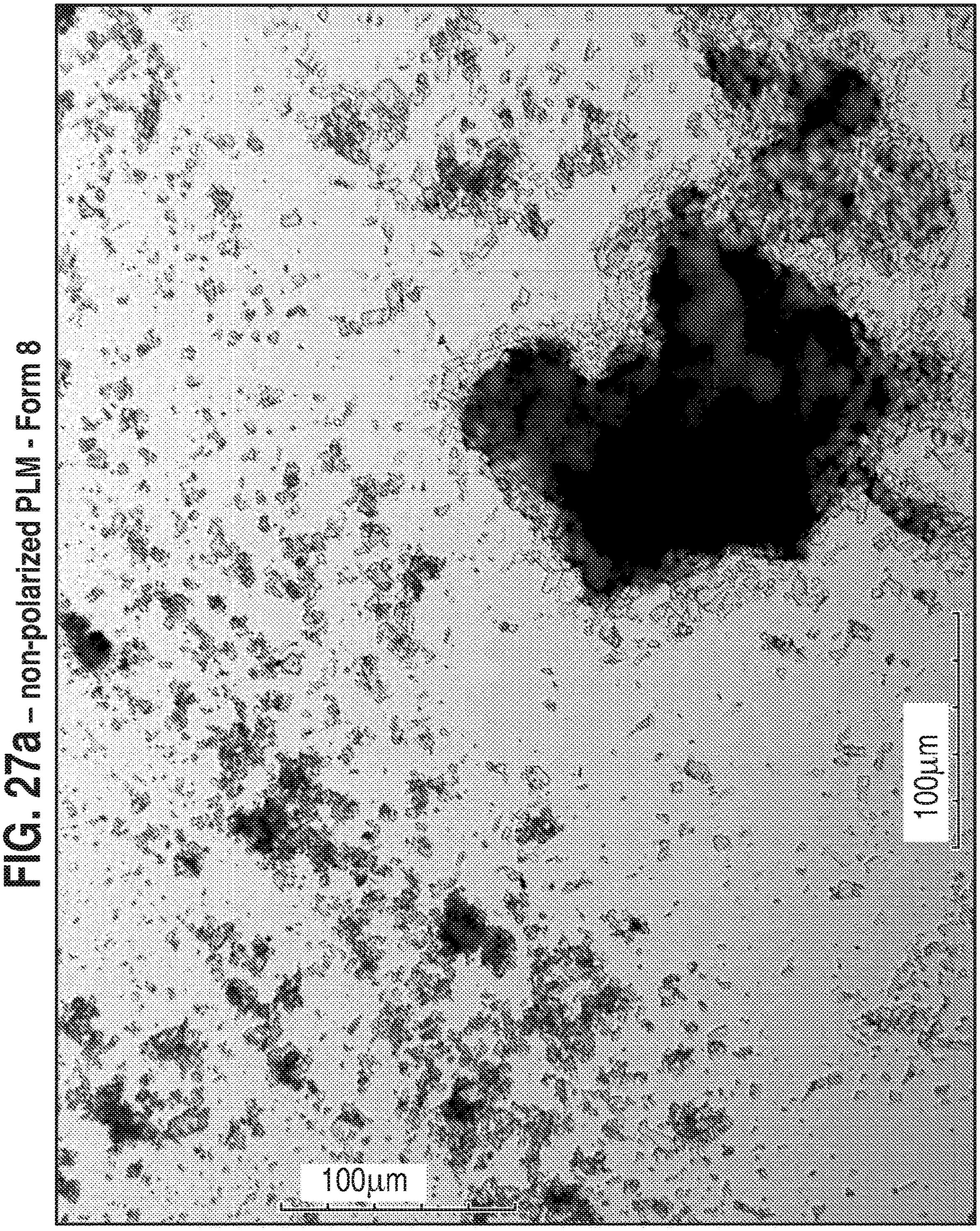

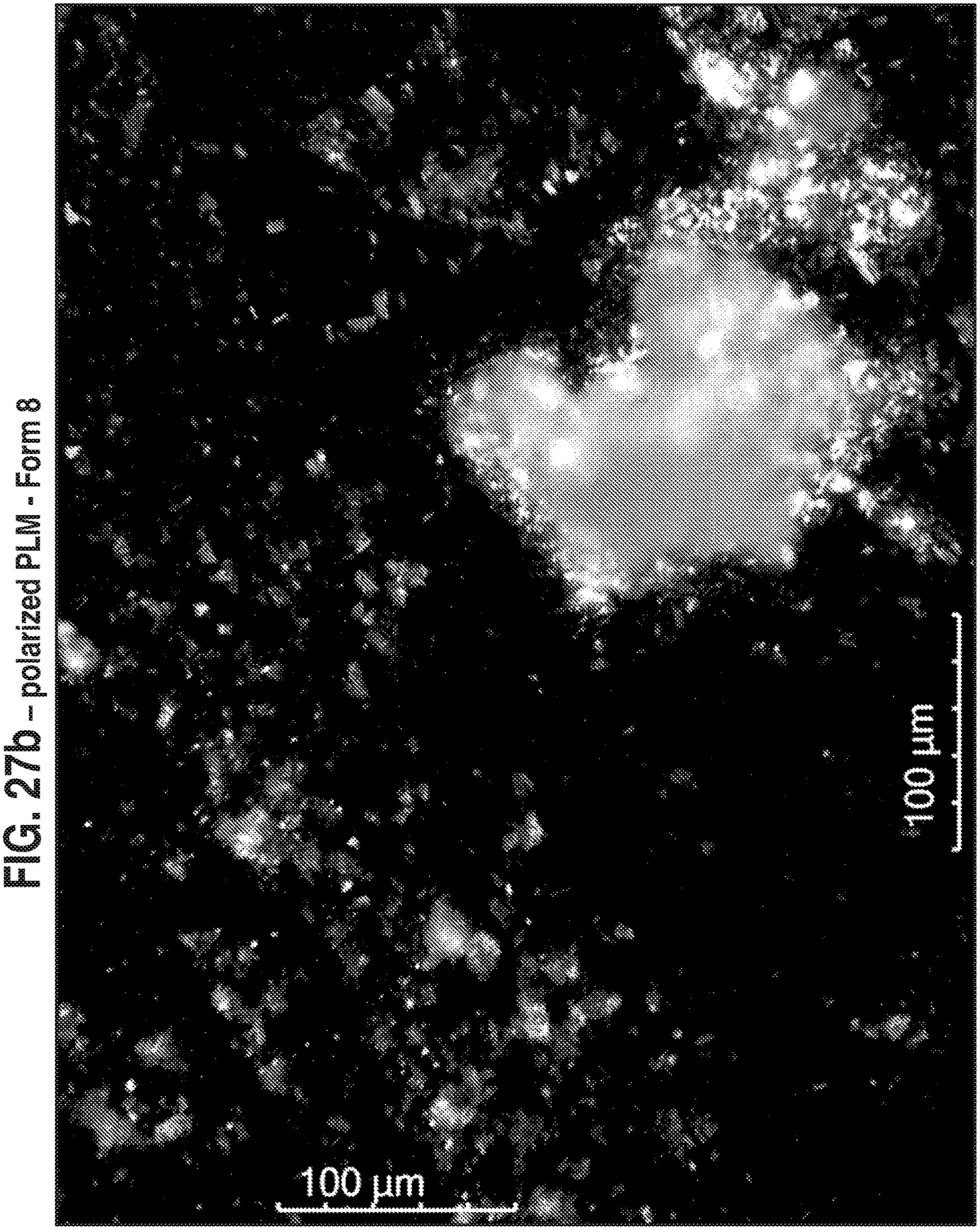
FIG. 27b – polarized PLM - Form 8

FIG. 28 – Form 1 - 1H NMR
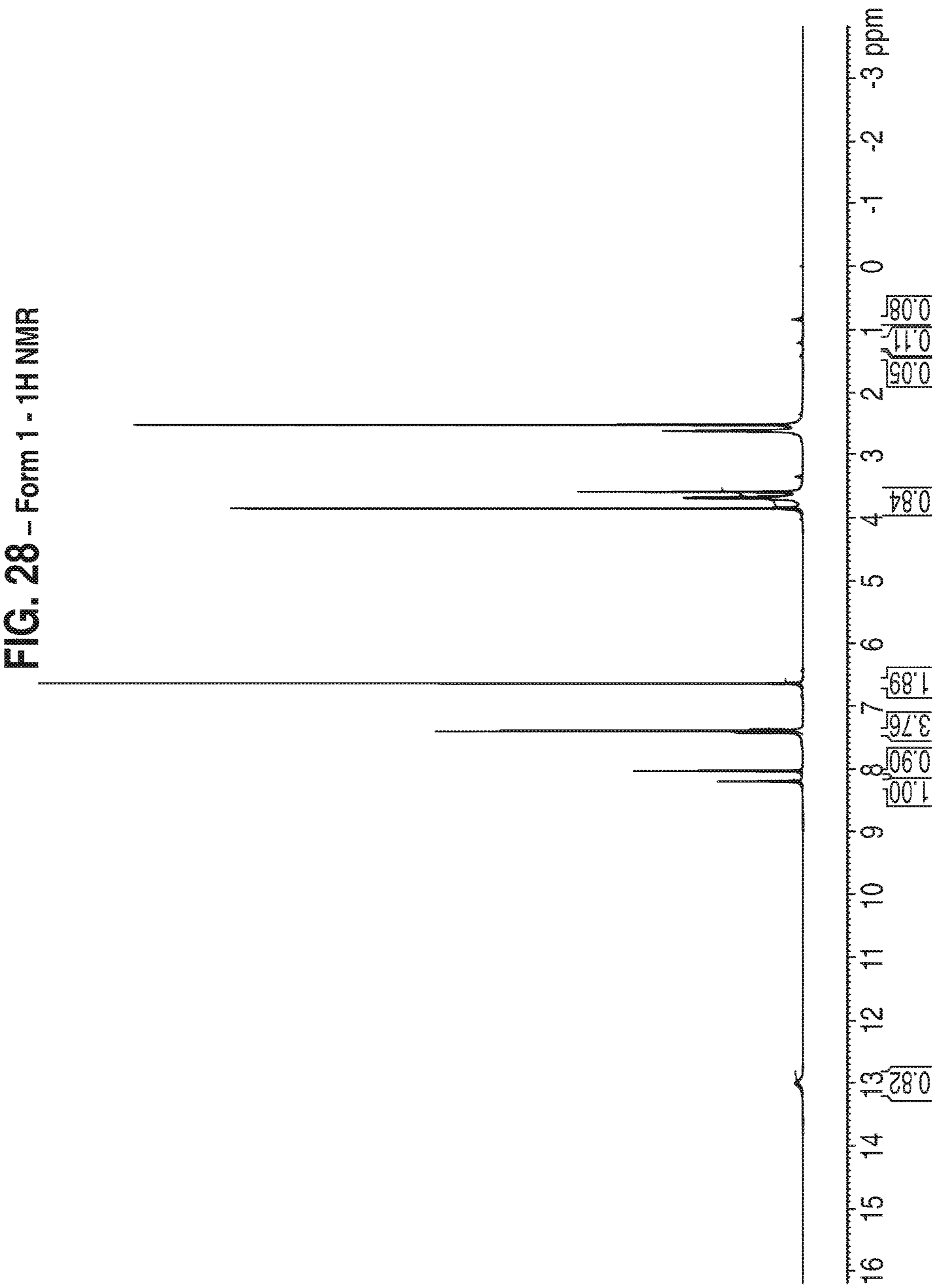

FIG. 28 (contd) – Form 1 - 1H NMR

Current Data Parameters

| | | |
|---|---|---|
| EXPNO | 1 | |
| PROCNO | 1 | |

F2 - Acquisition Parameters

| | | |
|---|---|---|
| Time | 13.11 | h |
| INSTRUM | spect | |
| PROBHD | Z108618_0863 ( | |
| PULPROG | zg30 | |
| TD | 65536 | |
| SOLVENT | DMSO | |
| NS | 16 | |
| DS | 2 | |
| SWH | 8012.820 | Hz |
| FIDRESAQ | 0.244532 | Hz |
| | 4.0894465 | sec |
| RG | 117.05 | |
| DW | 62.400 | use |
| DE | 6.50 | use |
| TE | 298.0 | K |
| D1 | 15.00000000 | sec |
| TD0 | 1 | |
| SFO1 | 400.0324702 | MHz |
| NUC1 | 1H | |
| P0 | 4.67 | use |
| P1 | 14.00 | use |
| PLW1 | 12.63199997 | W |

F2 - Processing parameters

| | | |
|---|---|---|
| SI | 65536 | |
| SF | 400.0299979 | MHz |
| WDW | EM | |
| SSB | 0 | |
| LB | 0.30 | Hz |
| GB | 0 | |
| PC | 1.00 | |

FIG. 29 – Form 2 - 1H NMR
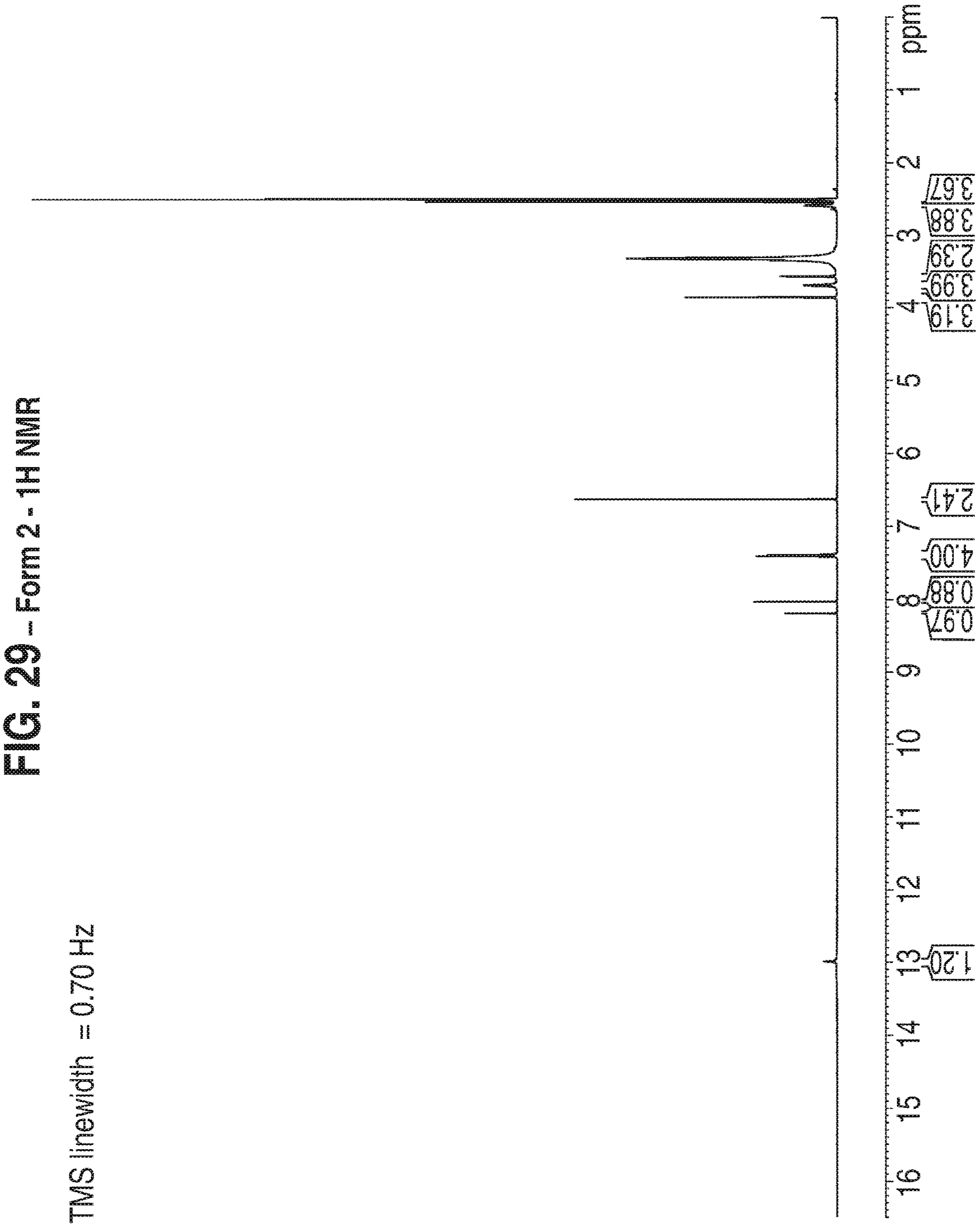

FIG. 29 (contd) – Form 2 - 1H NMR

Current Data Parameters

| | | |
|---|---|---|
| EXPNO | 10 | |
| PROCNO | 1 | |

F2 - Acquisition Parameters

| | | |
|---|---|---|
| Time | 18.47 | h |
| INSTRUM | av500 | |
| PROBHD | Z107909_0010 ( | |
| PULPROG | zg30 | |
| TD | 65536 | |
| SOLVENT | DMSO | |
| NS | 8 | |
| DS | 2 | |
| SWH | 10330.578 | Hz |
| FIDRES | 0.315264 | Hz |
| AQ | 3.1719425 | sec |
| RG | 57 | |
| DW | 48.400 | use |
| DE | 14.00 | use |
| TE | 300.1 | K |
| D1 | 1.00000000 | sec |
| TD0 | 1 | |
| SFO1 | 500.1230884 | MHz |
| NUC1 | 1H | |
| P1 | 10.00 | use |
| PLW1 | 10.39999962 | W |

F2 - Processing parameters

| | | |
|---|---|---|
| SI | 131072 | |
| SF | 500.1200000 | MHz |
| WDW | EM | |
| SSB | 0 | |
| LB | 0.30 | Hz |
| GB | 0 | |
| PC | 4.00 | |

FIG. 30 – Form 3 - 1H NMR
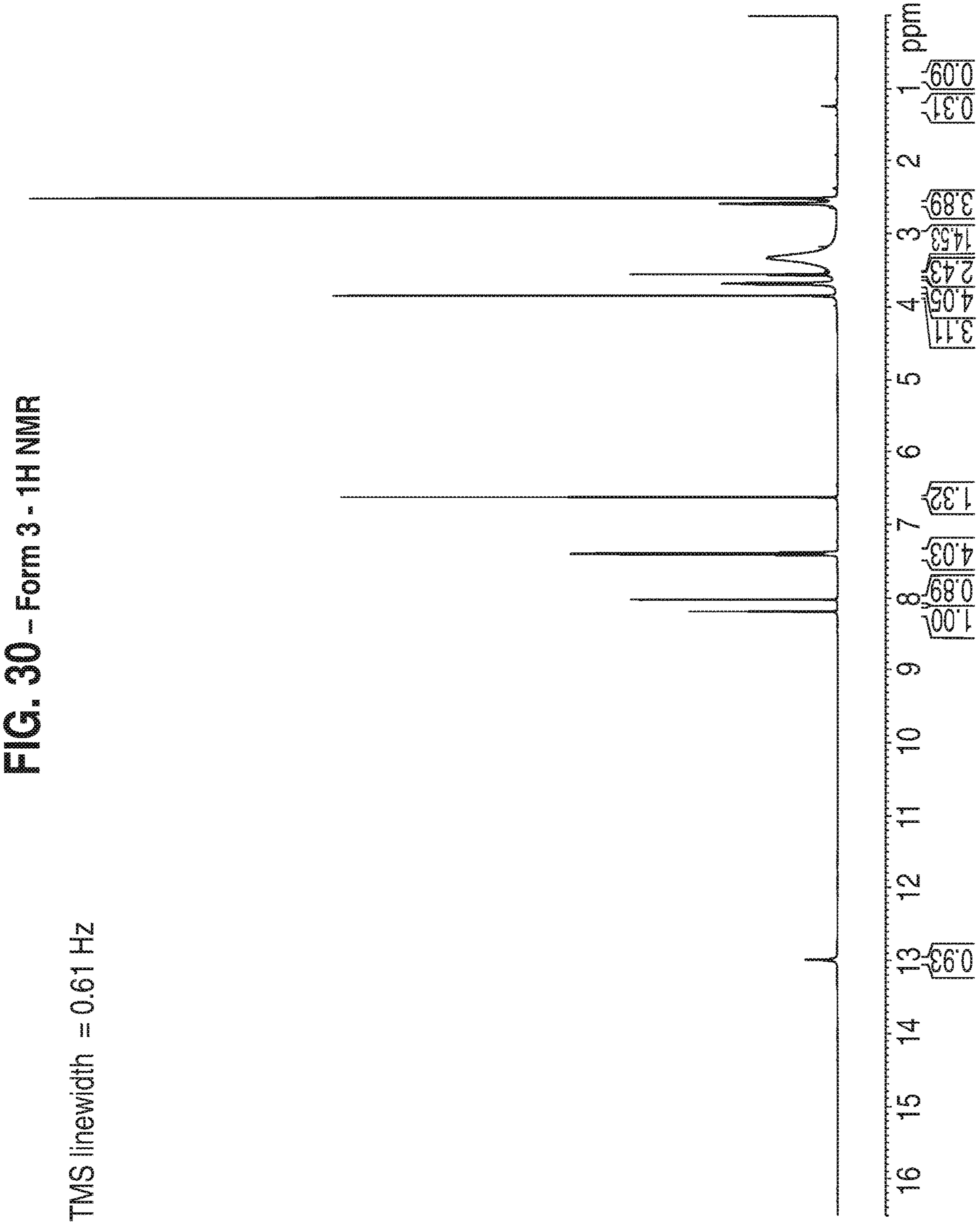

Figure 30:
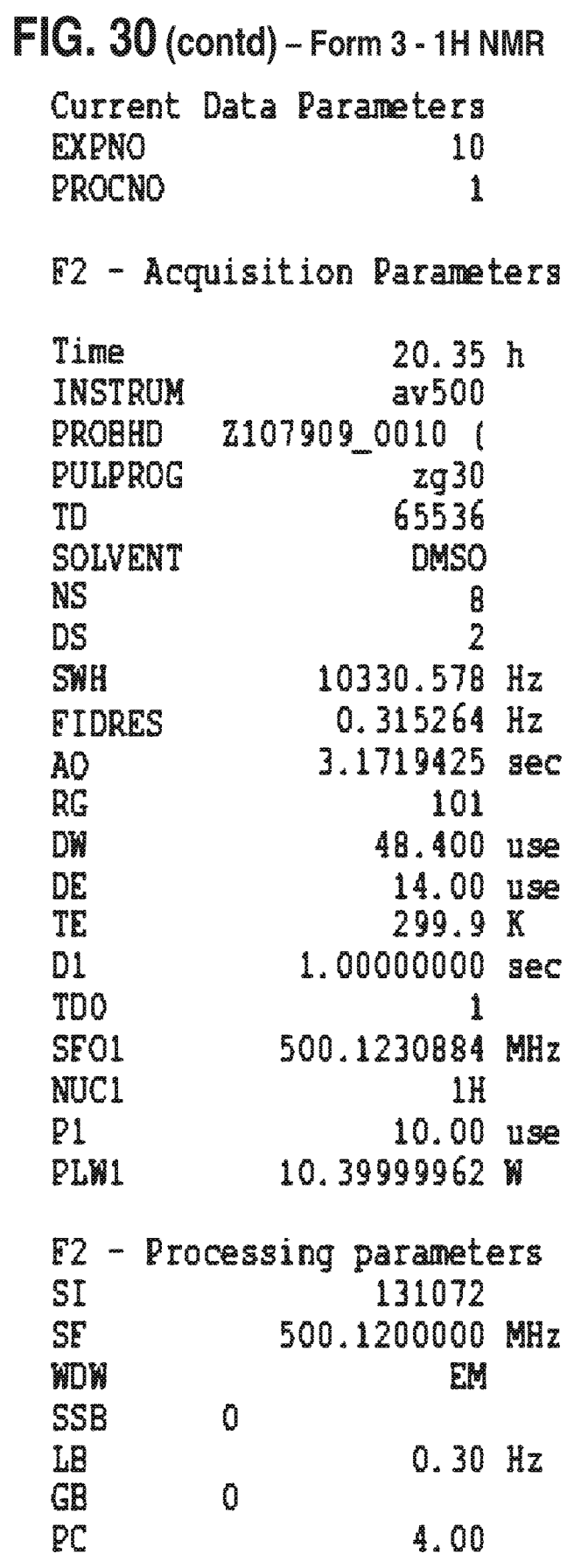

FIG. 30 (contd) – Form 3 - 1H NMR

Current Data Parameters

| | | |
|---|---|---|
| EXPNO | 10 | |
| PROCNO | 1 | |

F2 - Acquisition Parameters

| | | |
|---|---|---|
| Time | 20.35 | h |
| INSTRUM | av500 | |
| PROBHD | Z107909_0010 ( | |
| PULPROG | zg30 | |
| TD | 65536 | |
| SOLVENT | DMSO | |
| NS | 8 | |
| DS | 2 | |
| SWH | 10330.578 | Hz |
| FIDRES | 0.315264 | Hz |
| AQ | 3.1719425 | sec |
| RG | 101 | |
| DW | 48.400 | use |
| DE | 14.00 | use |
| TE | 299.9 | K |
| D1 | 1.00000000 | sec |
| TD0 | 1 | |
| SFO1 | 500.1230884 | MHz |
| NUC1 | 1H | |
| P1 | 10.00 | use |
| PLW1 | 10.39999962 | W |

F2 - Processing parameters

| | | |
|---|---|---|
| SI | 131072 | |
| SF | 500.1200000 | MHz |
| WDW | EM | |
| SSB | 0 | |
| LB | 0.30 | Hz |
| GB | 0 | |
| PC | 4.00 | |

FIG. 31 – Form 4 - 1H NMR
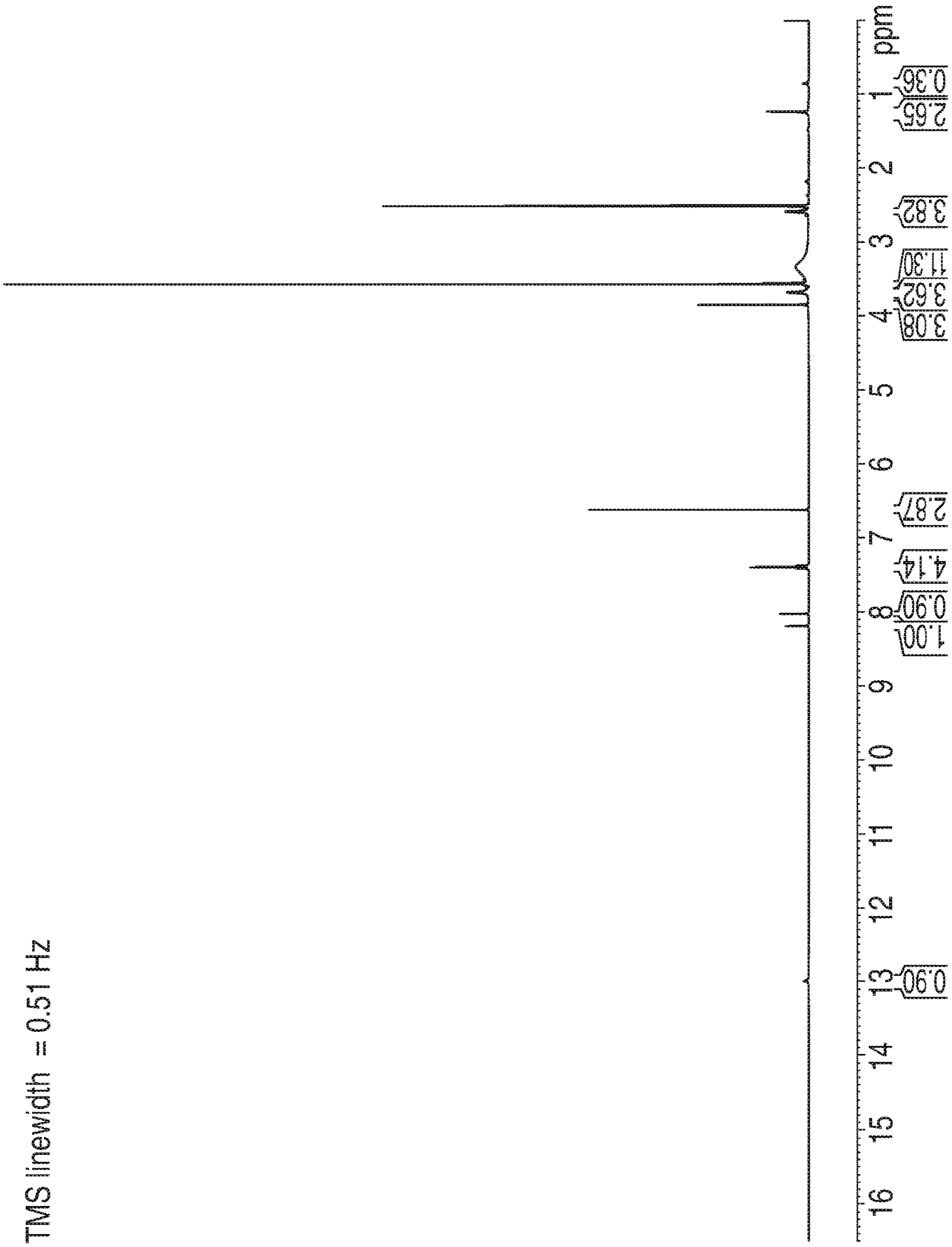

FIG. 31 (contd) – Form 4 - 1H NMR

Current Data Parameters

| | | |
|---|---|---|
| EXPNO | 10 | |
| PROCNO | 1 | |

F2 - Acquisition Parameters

| | | |
|---|---|---|
| Time | 11.37 | h |
| INSTRUM | av500 | |
| PROBHD | Z107909_0010 ( | |
| PULPROG | zg30 | |
| TD | 65536 | |
| SOLVENT | DMSO | |
| NS | 8 | |
| DS | 2 | |
| SWH | 10330.578 | Hz |
| FIDRES | 0.315264 | Hz |
| AQ | 3.1719425 | sec |
| RG | 57 | |
| DW | 48.400 | use |
| DE | 14.00 | use |
| TE | 299.9 | K |
| D1 | 1.00000000 | sec |
| TD0 | 1 | |
| SFO1 | 500.1230884 | MHz |
| NUC1 | 1H | |
| P1 | 10.00 | use |
| PLW1 | 10.39999962 | W |

F2 - Processing parameters

| | | |
|---|---|---|
| SI | 131072 | |
| SF | 500.1200000 | MHz |
| WDW | EM | |
| SSB | 0 | |
| LB | 0.30 | Hz |
| GB | 0 | |
| PC | 1.00 | |

FIG. 32 – Form 5 - 1H NMR
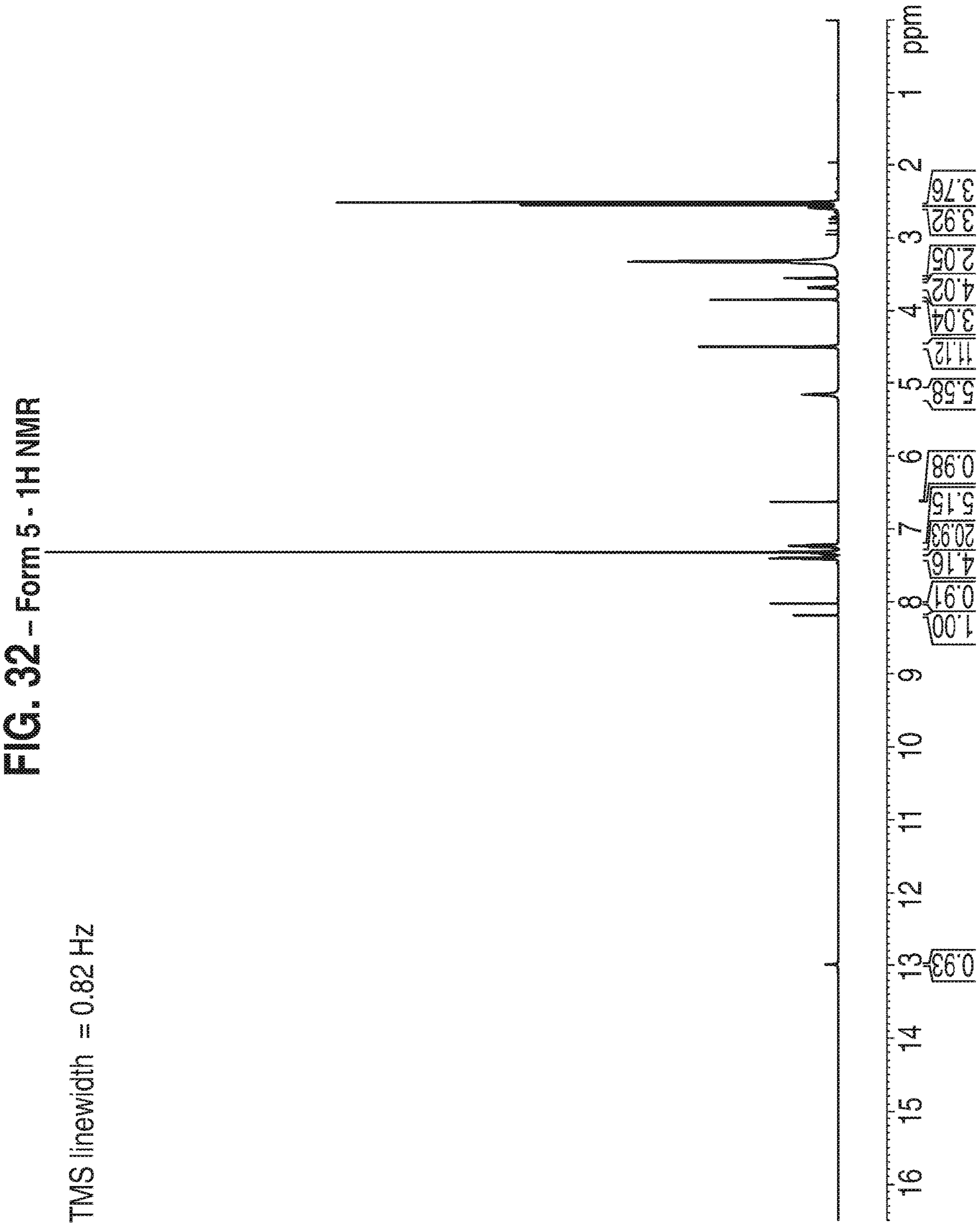

FIG. 32 (contd) – Form 5 - 1H NMR

```
Current Data Parameters
EXPNO                     10
PROCNO                     1

F2 - Acquisition Parameters

Time                   18.51 h
INSTRUM                av500
PROBHD    Z107909_0010 (
PULPROG                 zg30
TD                     65536
SOLVENT                 DMSO
NS                         8
DS                         2
SWH                10330.578 Hz
FIDRES              0.315264 Hz
AQ                 3.1719425 sec
RG                        57
DW                    48.400 use
DE                     14.00 use
TE                     300.1 K
D1                1.00000000 sec
TD0                        1
SFO1             500.1230884 MHz
NUC1                      1H
P1                     10.00 use
PLW1             10.39999962 W

F2 - Processing parameters
SI                    131072
SF               500.1200000 MHz
WDW                       EM
SSB         0
LB                      0.30 Hz
GB          0
PC                      4.00
```

FIG. 33 – Form 7 - 1H NMR
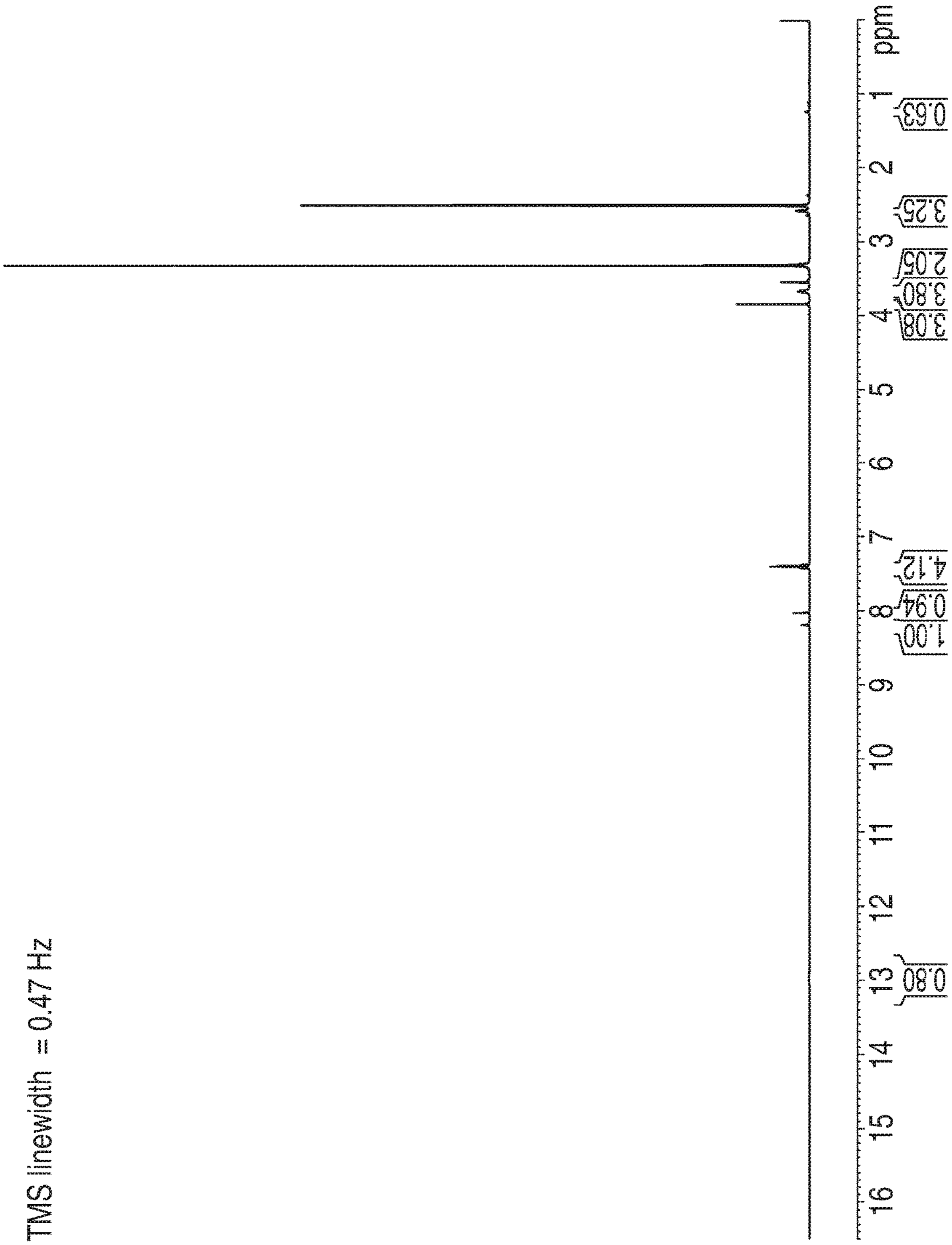

FIG. 33 (contd) – Form 7 - 1H NMR

Current Data Parameters

| | | |
|---|---|---|
| EXPNO | 10 | |
| PROCNO | 1 | |

F2 - Acquisition Parameters

| | | |
|---|---|---|
| Time | 13.49 | h |
| INSTRUM | av500 | |
| PROBHD | Z107909_0010 ( | |
| PULPROG | zg30 | |
| TD | 65536 | |
| SOLVENT | DMSO | |
| NS | 8 | |
| DS | 2 | |
| SWH | 10330.578 | Hz |
| FIDRES | 0.315264 | Hz |
| AQ | 3.1719425 | sec |
| RG | 57 | |
| DW | 48.400 | use |
| DE | 14.00 | use |
| TE | 299.9 | K |
| D1 | 1.00000000 | sec |
| TD0 | 1 | |
| SFO1 | 500.1230884 | MHz |
| NUC1 | 1H | |
| P1 | 10.00 | use |
| PLW1 | 10.39999962 | W |

F2 - Processing parameters

| | | |
|---|---|---|
| SI | 131072 | |
| SF | 500.1200000 | MHz |
| WDW | EM | |
| SSB | 0 | |
| LB | 0.30 | Hz |
| GB | 0 | |
| PC | 4.00 | |

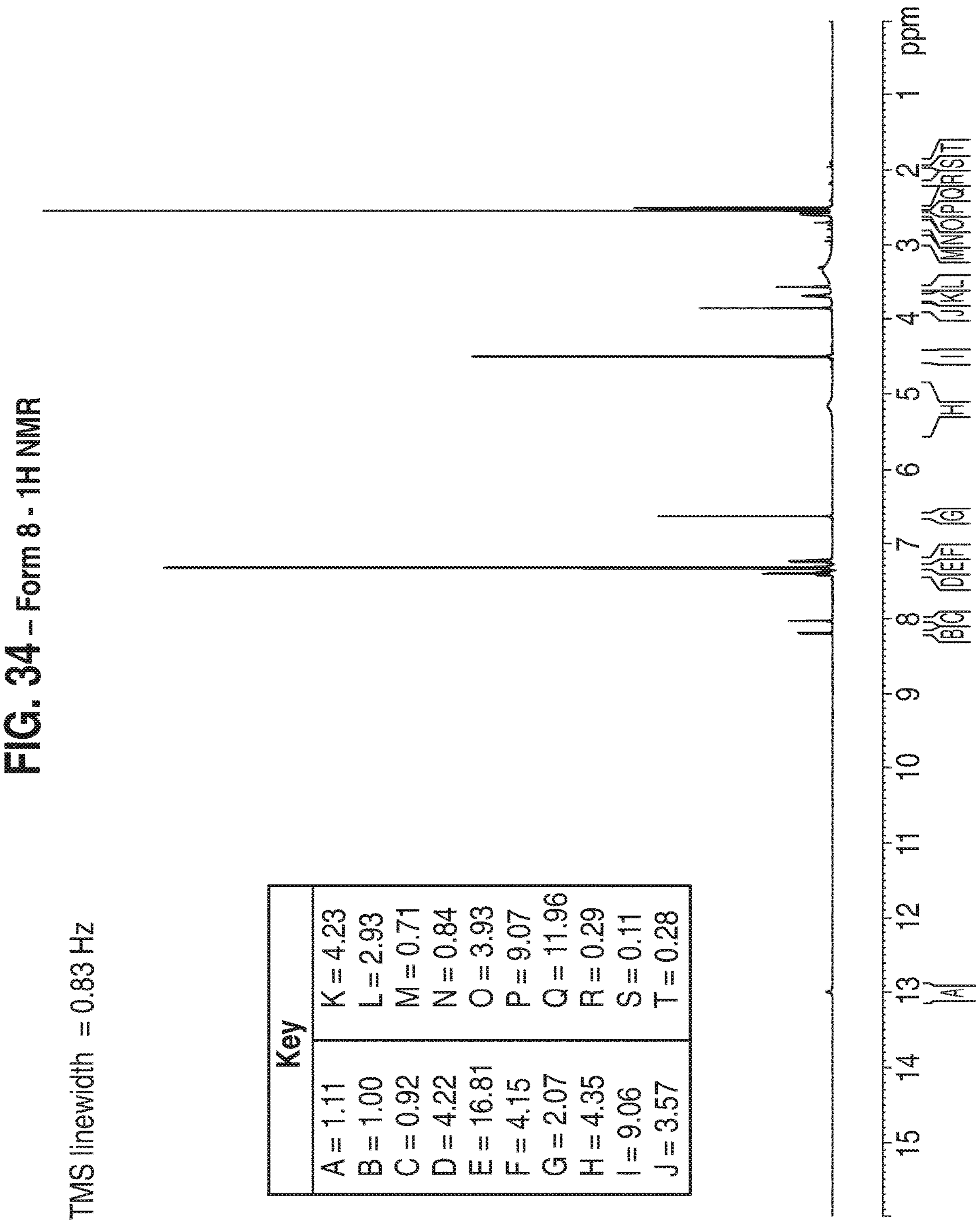
FIG. 34 – Form 8 - 1H NMR
TMS linewidth = 0.83 Hz
| Key | |
|---|---|
| A = 1.11 | K = 4.23 |
| B = 1.00 | L = 2.93 |
| C = 0.92 | M = 0.71 |
| D = 4.22 | N = 0.84 |
| E = 16.81 | O = 3.93 |
| F = 4.15 | P = 9.07 |
| G = 2.07 | Q = 11.96 |
| H = 4.35 | R = 0.29 |
| I = 9.06 | S = 0.11 |
| J = 3.57 | T = 0.28 |

Figure 34:
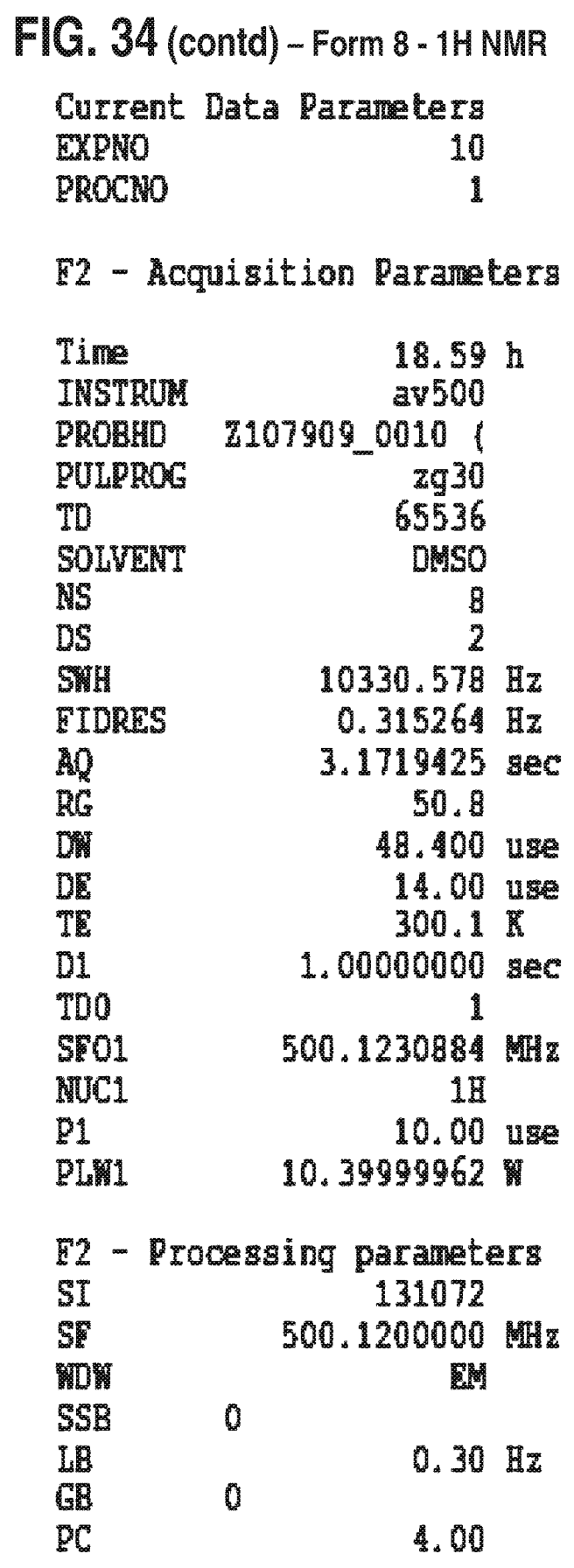

FIG. 34 (contd) – Form 8 - 1H NMR

Current Data Parameters

| | | |
|---|---|---|
| EXPNO | 10 | |
| PROCNO | 1 | |

F2 - Acquisition Parameters

| | | |
|---|---|---|
| Time | 18.59 | h |
| INSTRUM | av500 | |
| PROBHD | Z107909_0010 ( | |
| PULPROG | zg30 | |
| TD | 65536 | |
| SOLVENT | DMSO | |
| NS | 8 | |
| DS | 2 | |
| SWH | 10330.578 | Hz |
| FIDRES | 0.315264 | Hz |
| AQ | 3.1719425 | sec |
| RG | 50.8 | |
| DW | 48.400 | use |
| DE | 14.00 | use |
| TE | 300.1 | K |
| D1 | 1.00000000 | sec |
| TD0 | 1 | |
| SFO1 | 500.1230884 | MHz |
| NUC1 | 1H | |
| P1 | 10.00 | use |
| PLW1 | 10.39999962 | W |

F2 - Processing parameters

| | | |
|---|---|---|
| SI | 131072 | |
| SF | 500.1200000 | MHz |
| WDW | EM | |
| SSB | 0 | |
| LB | 0.30 | Hz |
| GB | 0 | |
| PC | 4.00 | |

FIG. 35 – Form 1 DVS isotherm
DVS Isotherm Plot
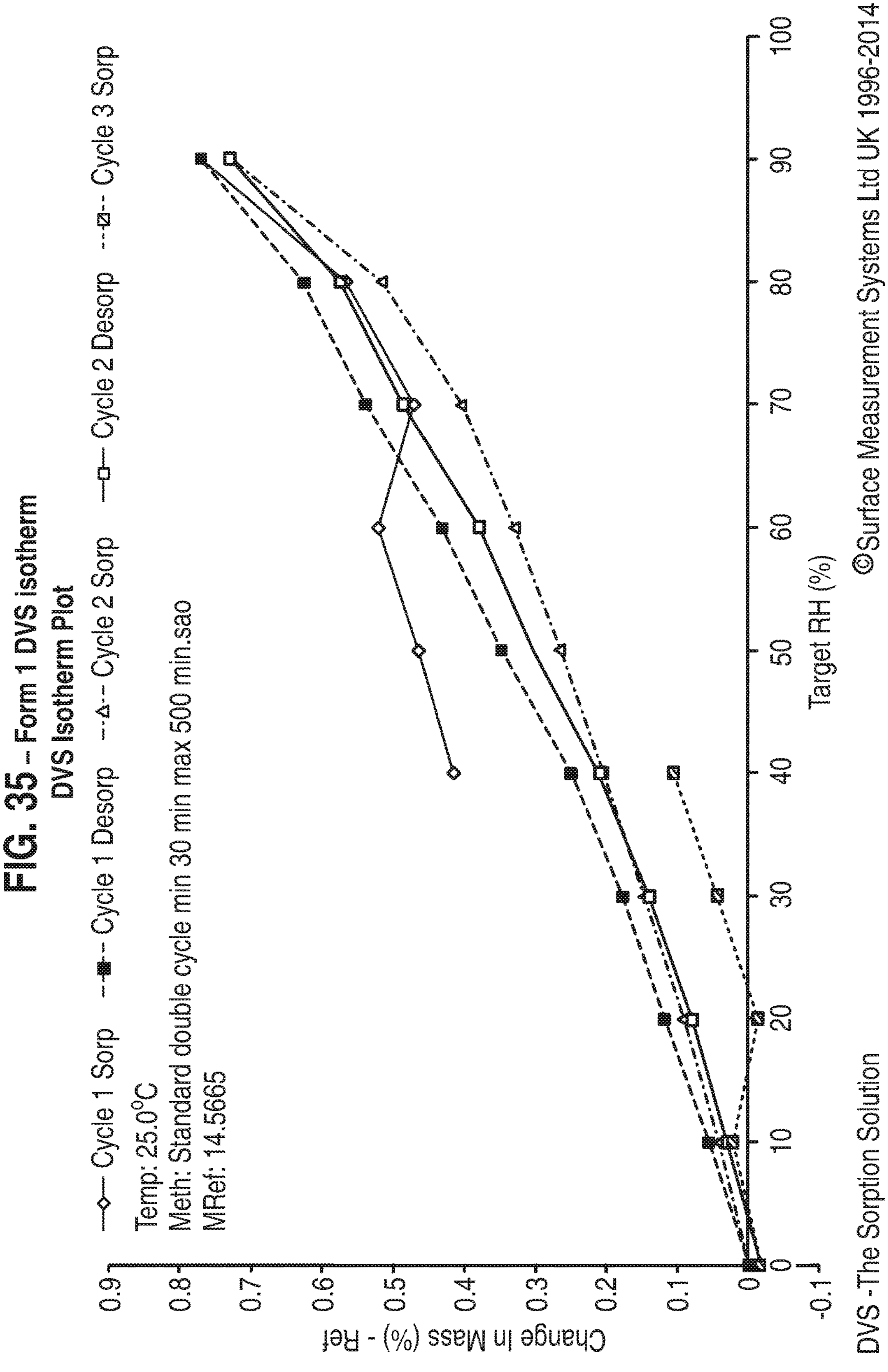

FIG. 36 – Form 1 DVS kinetic
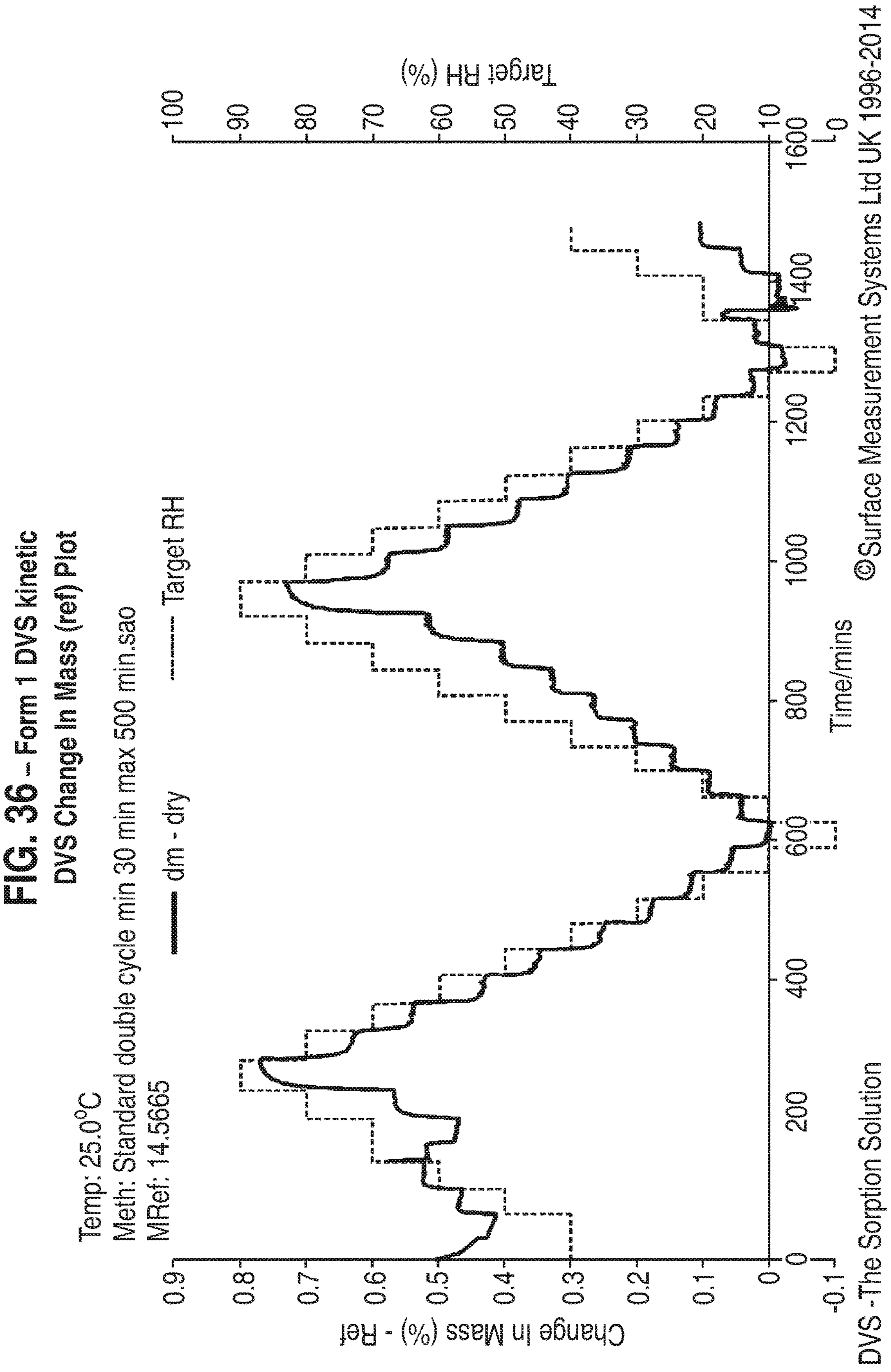

FIG. 37 – Form 3 DVS isotherm
DVS Isotherm Plot
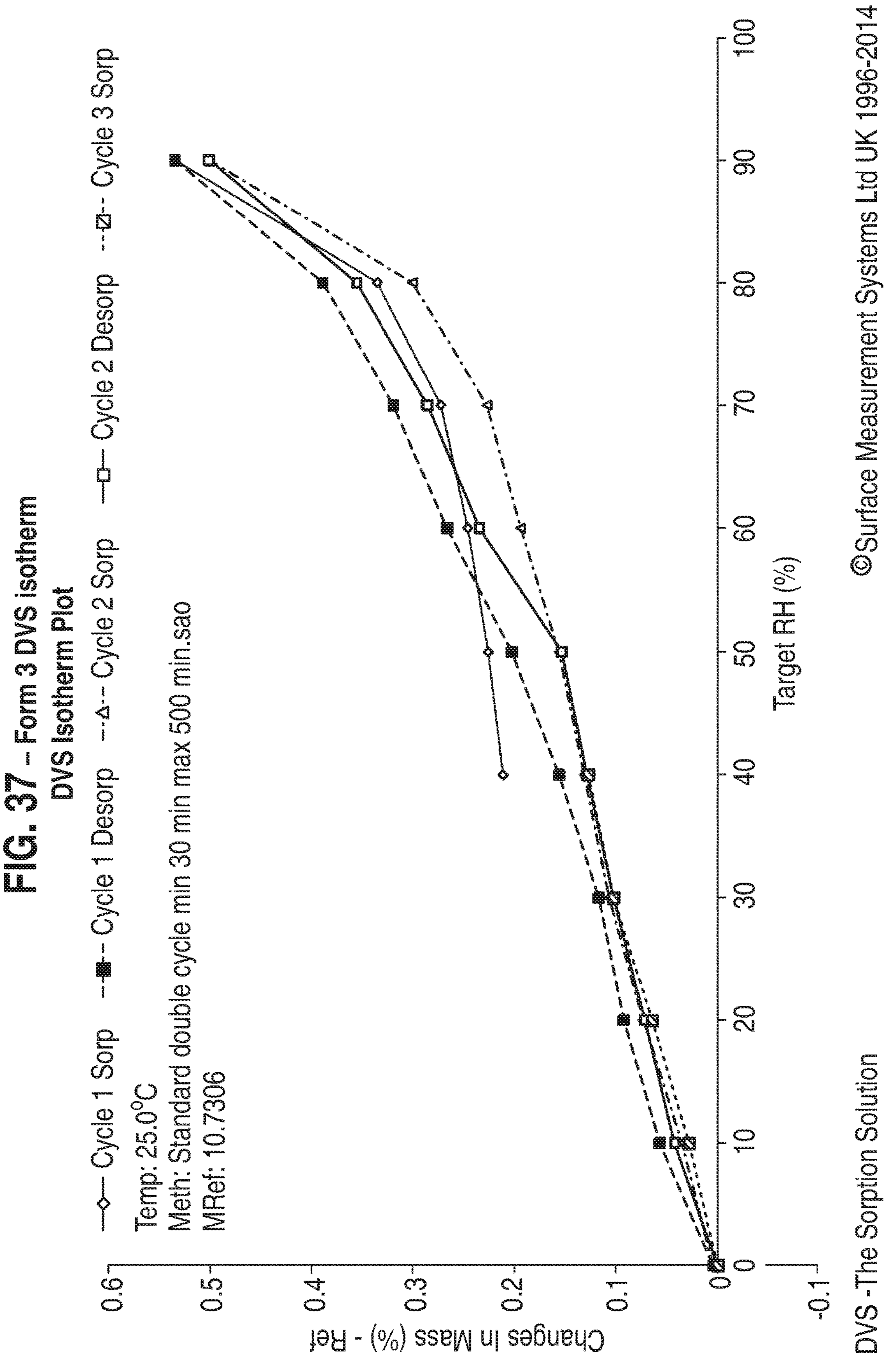

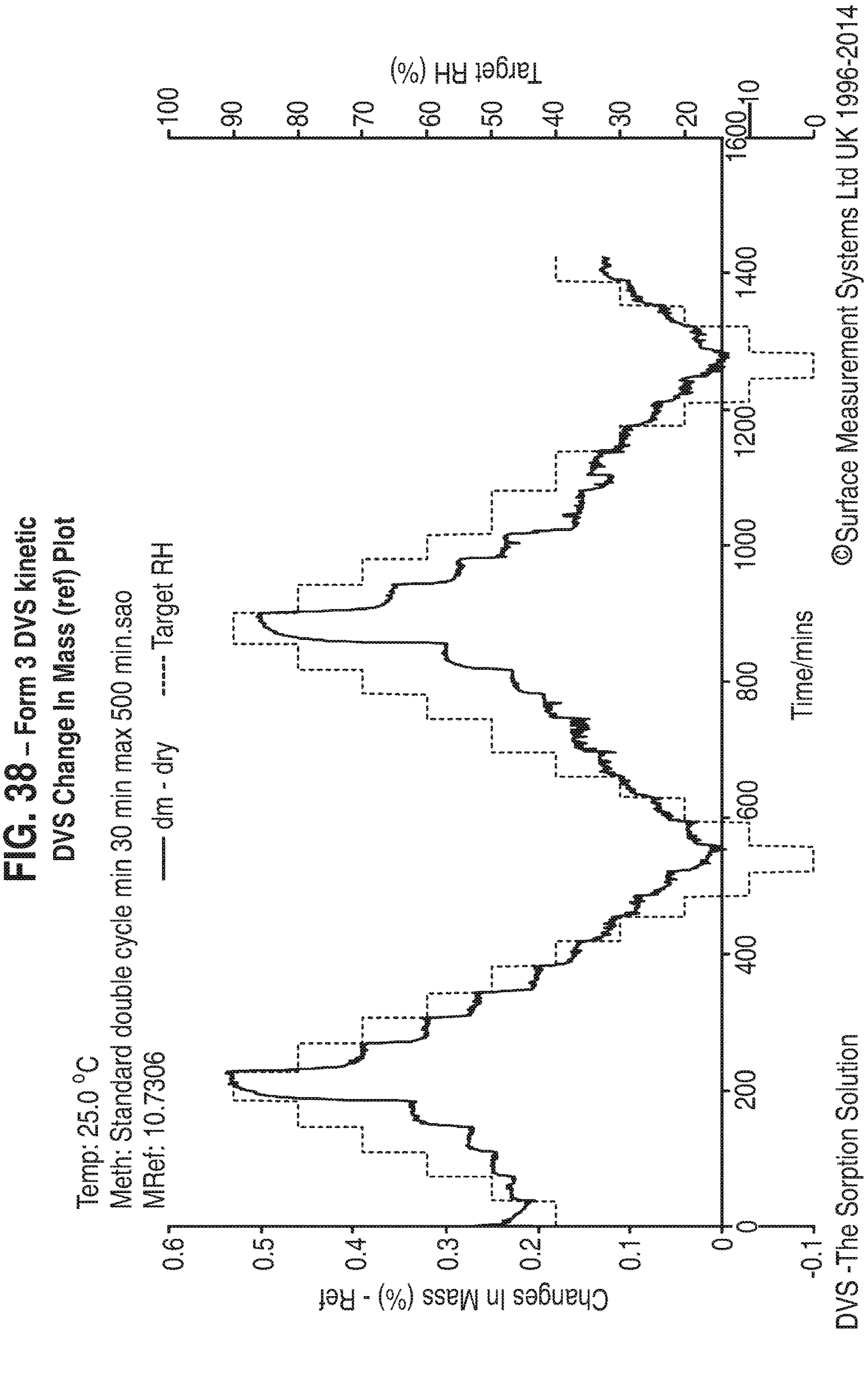
FIG. 38 – Form 3 DVS kinetic
DVS Change In Mass (ref) Plot
Temp: 25.0 °C
Meth: Standard double cycle min 30 min max 500 min.sao
MRef: 10.7306
—— dm - dry    - - - - - Target RH
Changes In Mass (%) - Ref
Target RH (%)
Time/mins
©Surface Measurement Systems Ltd UK 1996-2014
DVS -The Sorption Solution

FIG. 39 – Salt assessment

| | Base | Mono-mesylate | Di-mesylate | Mono-HCl | Di-HCl | Fumarate (1:1) |
|---|---|---|---|---|---|---|
| Aqueous solubility | 1 | 3 | 3 | 2 | 3 | 2 |
| Purity (HPLC) | 1 | 1 | 1 | 2 | 2 | 3 |
| Melting point/DSC | 3 | 1 | 2 | 2 | 1 | 3 |
| Hygroscopicity/DVS | 3 | 1 | 1 | 1 | 1 | 3 |
| Potency | 3 | 1 | 1 | 2 | 2 | 1 |
| Stoichiometry/elementary analysis | 3 | 1 | 1 | 3 | 3 | 2 |
| Processability | 2 | 1 | 1 | 3 | 2 | 3 |
| Dissolution | 3 | 3 | 3 | 3 | 3 | 3 |
| Suitability index | 2.4 | 1.5 | 1.6 | 2.3 | 2.1 | 2.5 |

FIG. 40 – Stability of Form 1
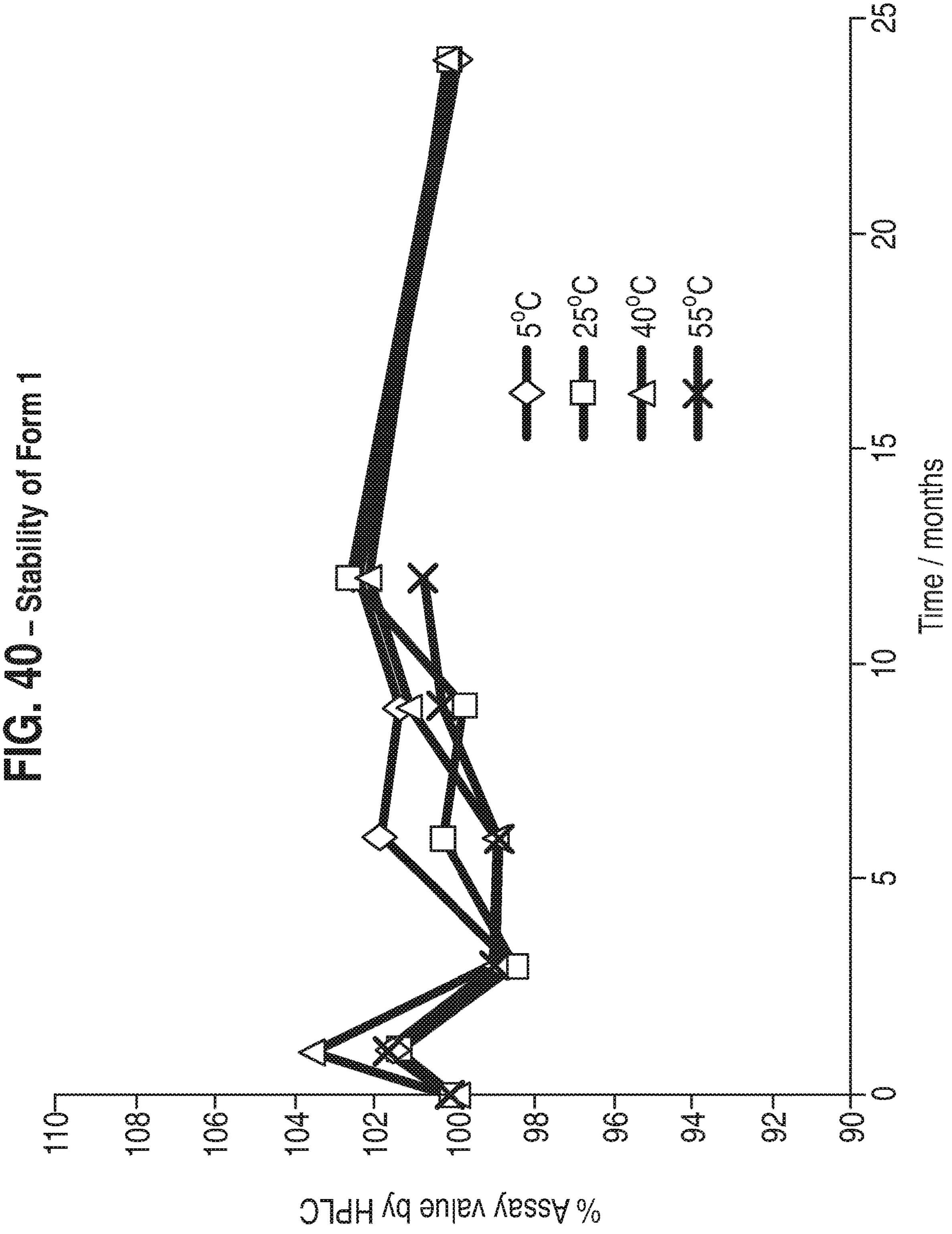

FIG. 40 (contd) – Stability of Form 1
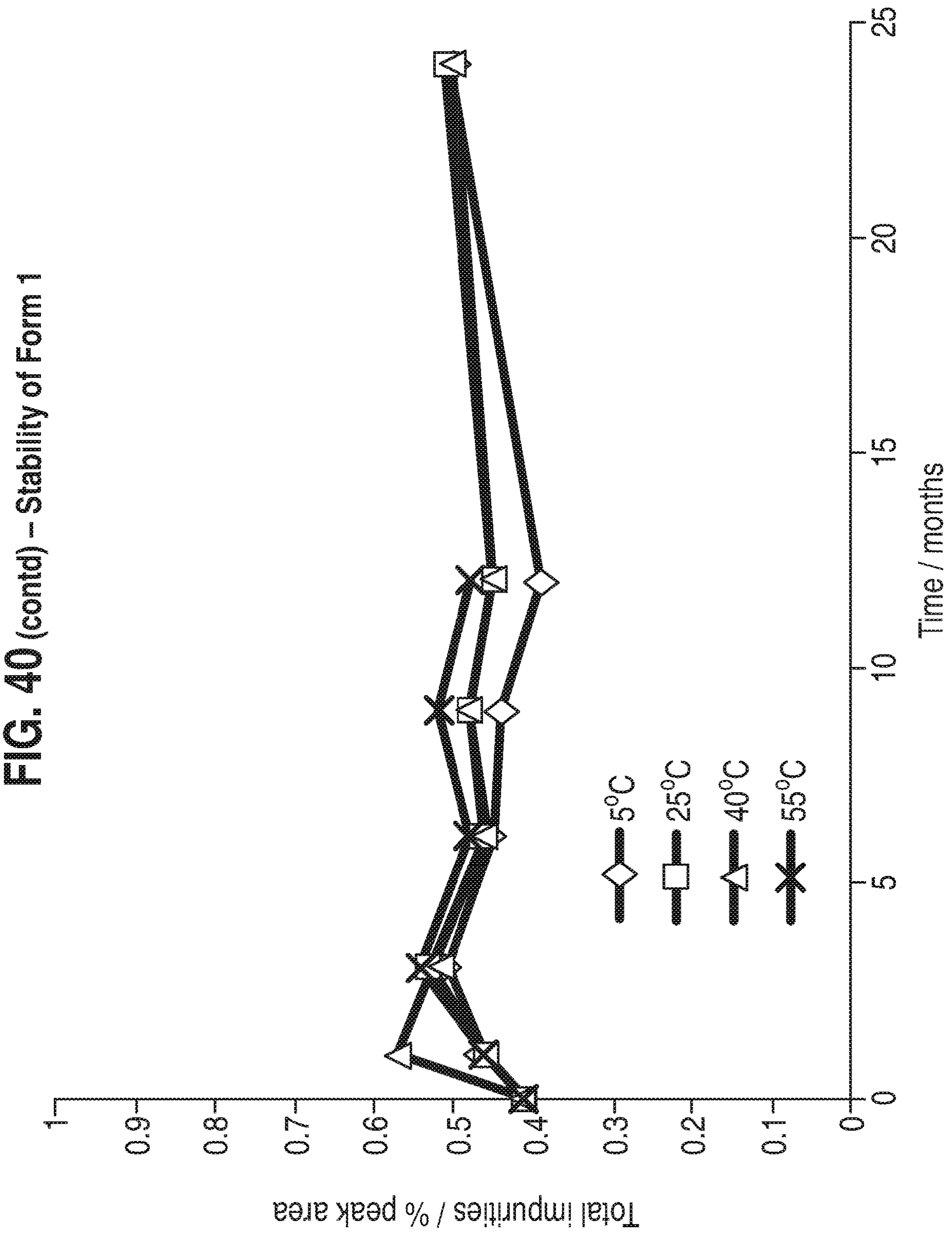

SALTS AND POLYMORPHIC FORMS OF 6-CHLORO-7-(4-(4-CHLOROBENZYL) PIPERAZIN-1-YL)-2-(1,3-DIMETHYL-1H-PYRAZOL-4-YL)-3H-IMIDAZO[4,5-B]PYRIDINE

FIELD OF INVENTION

The present invention relates to salts and polymorphic forms of a pharmaceutically active compound. More specifically, the present invention relates to salts and physical forms of a compounds that is an inhibitor of Aurora kinase enzyme activity. The compound of the invention is also an inhibitor of FMS-like tyrosine kinase 3 (FLT3) activity. The present invention also relates to processes for the preparation of the salts and crystalline forms of the compound, to pharmaceutical compositions comprising them, and to their use in the treatment of proliferative disorders, such as cancer, as well as other diseases or conditions in which Aurora kinase and/or FLT3 activity is implicated.

BACKGROUND

Proliferative diseases, such as cancer, are characterised by uncontrolled and unregulated cellular proliferation. Precisely what causes a cell to proliferate in an uncontrolled and unregulated manner has been the focus of intense research over recent decades.

Aurora kinases, a family of three serine-threonine kinases designated as A, B, and C, play key and distinct roles in different stages of mitosis. At the early stages of mitosis, Aurora-A forms a complex with the targeting protein for Xklp2 (TPX2) that regulates centrosome maturation and mitotic spindle assembly. Aurora-B forms complexes with the inner centromere protein (INCENP), survivin and borealin thereby regulating chromosome condensation, chromosome alignment, mitotic checkpoint and cytokinesis. Over expression of Aurora-A and Aurora-B has been reported in a wide range of human malignancies including breast, colorectal, ovarian, glioma, thyroid carcinoma, and seminoma. The function of Aurora-C during mitosis is less well understood. However, high expression of Aurora-C has been reported in the testis.

FLT3 is a trans-membrane kinase that belongs to the class III receptor tyrosine kinase (RTK) family. Binding of FLT3-ligand (FL) to its receptor leads to dimerisation, autophosphorylation and subsequent activation of downstream signalling pathways. High levels of FLT3 expression have been found in acute myeloid leukaemia (AML) blasts, and two major classes of mutations, i.e. internal-tandem duplications (ITDs) and tyrosine kinase domain (TKD) point mutations, have been identified in AML patients. Internal-tandem duplications are detected in 20-25% of AML patients, and tyrosine kinase domain point mutations in 5-10% of AML patients.

There is, therefore, a further need for compounds that have a dual function of inhibiting both Aurora kinases and FLT3. Such compounds would be useful for the treatment of diseases and/or conditions in which Aurora and/or FLT3 are implicated, such as, for example, AML.

Compound A described herein is one of such dual inhibitory compounds, having high activity against Aurora A, B, and C, and FLT3 kinases, as well an advantageous therapeutic window resulting from minimal interaction with cytochrome P450 activity and hERG. The preparation and biological testing of Compound A is described in WO 2013/190319. Other promising dual aurora/FLT3 kinase inhibitors are also described in WO 2013/190319.

In order for an active pharmaceutical ingredient (API) to be prepared for clinical use, it must possess certain physical properties that enable a commercially viable manufacturing process. Accordingly, the physical and chemical stability of the API are important factors. For example, the API and formulations containing it must be capable of being effectively stored over reasonable periods of time without exhibiting changes in physico-chemical properties. Moreover, an API often needs to contacted with solvents during the manufacturing process, so it is desirable for the API to have stability in commonly used organic solvents.

In addition, the compound ideally possesses a degree of inherent aqueous solubility so that it can be formulated in a manner that provides acceptable bioavailability, e.g. through gastrointestinal absorption. Obtaining a form of a therapeutically promising API that meets these complex and often contradicting requirements is a significant obstacle to pharmaceutical development.

It is therefore an object of the invention to provide new forms of the API Compound A that has one or more of the advantageous properties mentioned above.

SUMMARY OF INVENTION

The invention relates to salts and polymorphic forms of Compound A. Compound A (6-chloro-7-(4-(4-chlorobenzyl) piperazin-1-yl)-2-(1,3-dimethyl-1H-pyrazol-4-yl)-3H-imidazo[4,5-b]pyridine) has the structure:

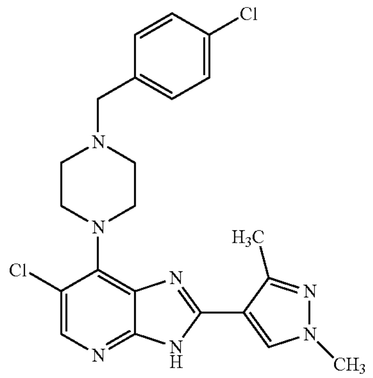 [SMILES: Cc1nn(C)cc1-c1nc2c(N3CCN(Cc4ccc(Cl)cc4)CC3)c(Cl)cnc2[nH]1]

Compound A is a potent Aurora A, B, C and FLT3 kinase inhibitor with a large therapeutic index due to minimal interaction with the hERG channel and cytochrome P450 enzymes. The inventors have discovered multiple salts and polymorphic forms of Compound A.

Salts of Compound A

The invention provides salts of Compound A. For example, the invention provides Compound A fumarate, Compound A mesylate, Compound A hydrochloride, Compound A malate, Compound A sulfate, and Compound A tartrate. More particular, the invention provides Compound A hemi-fumarate, Compound A mono-fumarate, Compound A mono-mesylate, Compound A di-mesylate, Compound A mono-hydrochloride, and Compound A di-hydrochloride.

The inventors discovered that many of these salts provided a desirable improvement in aqueous solubility of Compound A. For example, the mesylate and hydrochloride salts provided an unexpectedly large increase in solubility compared to the free base of Compound A, and was considered for further development. However, when taking into account a wider range of factors including hygroscopicity, Compound A fumarate was developed as an even more advantageous salt form.

A preferred salt of Compound A is the fumarate salt, in particular the mono-fumarate salt.

Polymorphic Forms of Compound A

The invention provides polymorphic forms of the dual aurora kinase/FLT3 inhibitor Compound A. The invention provides crystalline forms of Compound A, for example crystalline Compound A free base and crystalline Compound A fumarate. The invention provides amorphous Compound A, for example amorphous Compound A free base and amorphous Compound A fumarate. The invention provides Form 1 of Compound A. The invention provides Form 2 of Compound A. The invention provides Form 3 of Compound A. The invention provides Form 4 of Compound A. The invention provides Form 5 of Compound A. The invention provides Form 6 of Compound A. The invention provides Form 7 of Compound A. The invention provides Form 8 of Compound A. The inventors have discovered that Form 1 of Compound A is particularly advantageous.

Form 1

In one aspect, the invention relates to Form 1 of Compound A. Form 1 is characterised by one or more of the following properties:

a) Form 1 exhibits an XRPD pattern with at least the following XRPD peaks (CuK °2θ) at approximately (±0.1): 12.9, 20.5, 21.2, 22.9, and 23.4;

b) Form 1 exhibits an XRPD pattern substantially the same as shown in FIG. 1;

c) Form 1 exhibits substantially the following unit cell parameters at 298 K:

| System | a | b | c | alpha | beta | gamma | A |
|---|---|---|---|---|---|---|---|
| Monoclinic P | 9.7(1) Å | 17.4(2) Å | 32.5(1) Å | 90 | 88.35 | 90 | 5483 Å$^3$ |

d) Form 1 exhibits a DTA-TGA thermogram comprising a major endotherm with onset temperature at around (±0.5) 238° C.;

e) Form 1 exhibits a DTA-TGA thermogram substantially the same as shown in FIG. 11;

f) Form 1 contains a 1:1 molar ratio of fumarate to Compound A (Form 1 is a stoichiometric fumarate);

g) Form 1 is an unsolvated crystalline form; and/or h) Form 1 is obtainable from 1-butanol, 1-propanol, 2-ethoxyethanol, acetone, acetonitrile, methylethyl ketone (MEK), tetrahydrofuran (THF), 1,1-dimethoxymethane, or dimethylsulfoxide (DMSO).

Form 1 is preferably characterised by at least a), b) and/or c) above. Form 1 is has an advantageous balance of properties unexpected of a single physical form, including: stability in a wide range of conditions; solubility; no solvates; a lack of hygroscopicity; and useful particle morphology.

Form 2

In another aspect, the invention relates to Form 2 of Compound A. Form 2 is characterised by one or more of the following properties:

a) Form 2 exhibits an XRPD pattern with at least the following XRPD peaks (CuK 20) at approximately (±0.1): 15.4, 15.8, 16.3, and 24.5;

b) Form 2 exhibits an XRPD pattern substantially the same as shown in FIG. 2;

c) Form 2 exhibits substantially the following unit cell parameters at 298 K:

| System | a | b | c | alpha | beta | gamma |
|---|---|---|---|---|---|---|
| Triclinic P | 8.3(1) Å | 14.1(2) Å | 20.8(4) Å | 86.72 | 90.24 | 95.95 |

d) Form 2 exhibits a DTA-TGA thermogram comprising a major endotherm with onset temperature at around (±0.5) 231° C.;

e) Form 2 exhibits a DTA-TGA thermogram substantially the same as shown in FIG. 12;

f) Form 2 contains a 1:1 molar ratio of fumarate to Compound A (Form 2 is a stoichiometric fumarate);

g) Form 2 is an unsolvated crystalline form; and/or h) Form 2 is obtainable from 1,4-dioxane Form 2 is preferably characterised by at least a), b) and/or c) above. Form 2 has unexpected stability in 1,4-dioxane and under lyophilisation conditions.

Form 3

In another aspect, the invention relates to Form 3 of Compound A. Form 3 is characterised by one or more of the following properties:

a) Form 3 exhibits an XRPD pattern with at least the following XRPD peaks (CuK 2θ) at approximately (±0.1): 8.8, 17.4, 17.7, and 18.2;

b) Form 3 exhibits an XRPD pattern substantially the same as shown in FIG. 3;

c) Form 3 exhibits substantially the following unit cell parameters at 298 K:

| System | a | b | c | alpha | beta | gamma | A |
|---|---|---|---|---|---|---|---|
| Triclinic P | 9.7(2) Å | 12.7(3) Å | 24.6(3) Å | 78.92 | 86.15 | 102.2 | 2888 Å$^3$ |

d) Form 3 exhibits a DTA-TGA thermogram comprising a major endotherm with onset temperature at around (±0.5) 184° C.;

e) Form 3 exhibits a DTA-TGA thermogram substantially the same as shown in FIG. 13;

f) Form 3 contains a 1:2 molar ratio of fumarate to Compound A (Form 3 is a hemi-fumarate);

g) Form 3 is an monohydrate (1:1 molar ratio of water to Compound A); and/or h) Form 3 is obtainable from dimethoxymethane, 2-MeTHF, water:methanol (0:100, 40:60, 80:20, 95:5, 100:0), EtOAc IPA, MEK, MIBK, THF, acetone, acetonitrile.

Form 3 is preferably characterised by at least a), b) and/or c) above. Form 3 has the advantage that it is stable with respect to organic solvents such as dimethoxymethane, 2-MeTHF, water:methanol (0:100, 40:60, 80:20, 95:5, 100:0), EtOAc IPA, MEK, MIBK, THF, acetone, and acetonitrile. Form 3 has good stability under stressed and ambient conditions. Form 3 is only slightly hygroscopic.

Form 4

In another aspect, the invention relates to Form 4 of Compound A. Form 4 is characterised by one or more of the following properties:

a) Form 4 exhibits an XRPD pattern with at least the following XRPD peaks (CuK 2θ) at approximately (±0.1): 16.3, 18.7, 22.8, 23.1, and 25.7;

b) Form 4 exhibits an XRPD pattern substantially the same as shown in FIG. 4;

c) Form 4 exhibits a DTA-TGA thermogram comprising a major endotherm with onset temperature at around (±0.5) 142° C.;

d) Form 4 exhibits a DTA-TGA thermogram substantially the same as shown in FIG. 14;

e) Form 4 contains a 1:1 molar ratio of fumarate to Compound A (Form 4 is a stoichiometric fumarate); and/or f) Form 4 is a 1,4-dioxane solvate;

Form 4 is preferably characterised by at least a) and/or b). Form 4 is stable in organic solvents such as 1,4-dioxane. Form 4 converts to Form 2 on drying.

Form 5

In another aspect, the invention relates to Form 5 of Compound A. Form 5 is characterised by one or more of the following properties:

a) Form 5 exhibits an XRPD pattern with at least the following XRPD peaks (CuK 2θ) at approximately (±0.1): 21.5, 24.5, and 27.3;

b) Form 5 exhibits an XRPD pattern substantially the same as shown in FIG. 5;

c) Form 5 exhibits substantially the following unit cell parameters at 298 K:

| System | a | b | c | alpha | beta | gamma |
|---|---|---|---|---|---|---|
| Monoclinic P | 32.06(5) Å | 11.28(1) Å | 8.43(1) Å | 90 | 93.65(2) | 90 |

d) Form 5 exhibits a DTA thermogram comprising a major endotherm with onset temperature at around (±0.5) 229° C.;

e) Form 5 exhibits a DTA thermogram substantially the same as shown in FIG. 15;

f) Form 5 contains a 1:2 molar ratio of fumarate to Compound A (Form 5 is a hemi-fumarate);

g) Form 5 is a benzyl alcohol solvate; and/or h) Form 5 is obtainable from benzyl alcohol.

Form 5 is preferably characterised by at least a), b) and/or c) above. Form 5 is stable in organic solvents such as benzyl alcohol.

Form 6

In another aspect, the invention relates to Form 6 of Compound A. Form 6 is characterised by one or more of the following properties:

a) Form 6 exhibits an XRPD pattern with at least the following XRPD peaks (CuK 2θ) at approximately (±0.1): 9.1, 9.4, 9.8, 16.0, and 26.4;

b) Form 6 exhibits an XRPD pattern substantially the same as shown in FIG. 6;

c) Form 6 exhibits substantially the following unit cell parameters at 298 K:

| System | a | b | c | alpha | beta | gamma |
|---|---|---|---|---|---|---|
| Monoclinic P | 13.07 Å | 18.78 Å | 11.08 Å | 90 | 118.62 | 90 |

d) Form 6 is a free base of Compound A;

e) Form 6 is a DMSO solvate; and/or f) Form 6 is obtainable from DMSO.

Form 6 is preferably characterised by at least a), b) and/or c) above. Form 6 is stable in organic solvents such as DMSO.

Form 7

In another aspect, the invention relates to Form 7 of Compound A. Form 7 is characterised by one or more of the following properties:

a) Form 7 exhibits an XRPD pattern with at least the following XRPD peaks (CuK 2θ) at approximately (±0.1): 7.5, 7.9, 25.6, and 26.2;

b) Form 7 exhibits an XRPD pattern substantially the same as shown in FIG. 7;

c) Form 7 exhibits substantially the following unit cell parameters at 298 K:

| System | a | b | c | alpha | beta | Gamma |
|---|---|---|---|---|---|---|
| Triclinic P | 13.86 Å | 20.54 Å | 7.98 Å | 96.12 | 93.2 | 92.4 |

d) Form 7 exhibits a DTA thermogram comprising a major endotherm with onset temperature at around (±0.5) 240° C.;

e) Form 7 exhibits a DTA thermogram substantially the same as shown in FIG. 16;

f) Form 7 is unsolvated;

g) Form 7 is a free base of Compound A; and/or h) Form 7 is obtainable on drying Form 6 or from methanol.

Form 7 is preferably characterised by at least a), b) and/or c) above. Form 7 is stable in organic solvents such as methanol.

Form 8

In another aspect, the invention relates to Form 8 of Compound A. Form 8 is characterised by one or more of the following properties:

a) Form 8 exhibits an XRPD pattern with at least the following XRPD peaks (CuK 2θ) at approximately (±0.1): 10.4, 10.7, 11.1, 24.2, and 24.5;

b) Form 8 exhibits an XRPD pattern substantially the same as shown in FIG. 8;

c) Form 8 exhibits substantially the following unit cell parameters at 298 K:

| System | a | b | c | alpha | beta | gamma |
|---|---|---|---|---|---|---|
| Monoclinic P | 10.67 Å | 14.15 Å | 16.19 Å | 90 | 97.31 | 90 |

d) Form 8 exhibits a DTA thermogram comprising a major endotherm with onset temperature at around (±0.5) 232° C.;

e) Form 8 exhibits a DTA thermogram substantially the same as shown in FIG. 17;

f) Form 8 is a benzyl alcohol solvate;

g) Form 8 contains a 1:1 molar ratio of fumarate to Compound A (Form 8 is a stoichiometric fumarate); and/or h) Form 8 is obtainable from benzyl alcohol.

Form 8 is preferably characterised by at least a), b) and/or c) above. Form 8 is stable in organic solvents such as benzyl alcohol.

The invention also provides processes for the preparation of the crystalline forms of Compound A. Thus, The invention provides a process for the preparation of any of Forms 1, 2, 3, 4, 5, 6, 7, and 8 comprising the crystallisation of that form from Compound A. In a preferred embodiment, the form is prepared by lyophilisation of Compound A.

Use and Applications of the Invention

Each of the salts and polymorphs of the invention described above have a number of useful applications. The salts and/or polymorphs may be used together or individually. For example, the aspects described herein may involve a combination of two forms, for example Forms 1 and 2, 1 and 3, 1 and 4, 1 and 5, 1 and 6, 1 and 7, 1 and 8, 2 and 3, 2 and 4, 2 and 5, 2 and 6, 2 and 7, 2 and 8, 3 and 4, 3 and 5, 3 and 6, 3 and 7, 3 and 8, 4 and 5, 4 and 6, 4 and 7, 4 and 8, 5 and 6, 5 and 7, 5 and 8, 6 and 7, 6 and 8, or 7 and 8. The aspects described herein may involve a combination three, four, five, six, seven, or eight forms.

The invention also provides pharmaceutical compositions comprising one or more salts and/or polymorphs of Compound A. The invention also provides processes for formulating pharmaceutical compositions comprising Compound A.

The present invention also provides one or more salts and/or polymorphs of Compound A, or a pharmaceutical composition as defined herein, for use in therapy.

FIGURES

FIG. 1 illustrates the XRPD spectrum of Form 1.
FIG. 2 illustrates the XRPD spectrum of Form 2.
FIG. 3 illustrates the XRPD spectrum of Form 3.
FIG. 4 illustrates the XRPD spectrum of Form 4.
FIG. 5 illustrates the XRPD spectrum of Form 5.
FIG. 6 illustrates the XRPD spectrum of Form 6.
FIG. 7 illustrates the XRPD spectrum of Form 7.
FIG. 8 illustrates the XRPD spectrum of Form 8.
FIG. 9 illustrates XRPD spectra of Form 1 after 1, 3, and 6 months storage (Example 5).
FIG. 10 illustrates the XRPD spectrum of lyophilised Compound A fumarate.
FIG. 11 illustrates a DTA-TGA thermogram of Form 1.
FIG. 12 illustrates a DTA-TGA thermogram of Form 2.
FIG. 13 illustrates a DTA-TGA thermogram of Form 3.
FIG. 14 illustrates a DTA-TGA thermogram of Form 4.
FIG. 15 illustrates a DTA-TGA thermogram of Form 5.
FIG. 16 illustrates a DTA-TGA thermogram of Form 7.
FIG. 17 illustrates a DTA-TGA thermogram of Form 8.
FIG. 18 illustrates a DSC thermogram of Form 1.
FIG. 19 illustrates a DSC thermogram of Form 3.
FIG. 20 illustrates a DSC thermogram of Form 7.
FIG. 21 illustrates non-polarized (a) and polarized (b) PLM images of Form 1.
FIG. 22 illustrates non-polarized (a) and polarized (b) PLM images of Form 2.
FIG. 23 illustrates non-polarized (a) and polarized (b) PLM images of Form 3.
FIG. 24 illustrates non-polarized (a) and polarized (b) PLM images of Form 4.
FIG. 25 illustrates non-polarized (a) and polarized (b) PLM images of Form 5.
FIG. 26 illustrates non-polarized (a) and polarized (b) PLM images of Form 7.
FIG. 27 illustrates non-polarized (a) and polarized (b) PLM images of Form 8.
FIG. 28 illustrates a 1H NMR of Form 1.
FIG. 29 illustrates a 1H NMR of Form 2.
FIG. 30 illustrates a 1H NMR of Form 3.
FIG. 31 illustrates a 1H NMR of Form 4.
FIG. 32 illustrates a 1H NMR of Form 5.
FIG. 33 illustrates a 1H NMR of Form 7.
FIG. 34 illustrates a 1H NMR of Form 8.
FIG. 35 shows a DVS isotherm plot of Form 1.
FIG. 36 shows a DVS kinetic plot of Form 1.
FIG. 37 shows a DVS isotherm plot of Form 3.
FIG. 38 shows a DVS kinetic plot of Form 3.
FIG. 39 shows the results from the salt assessment experiment (Example 4).
FIG. 40 shows the change in the level of impurities over 24 months for Form 1 (Example 5).

DETAILED DESCRIPTION

Salts of Compound A

The invention provides salts of Compound A. The invention provides Compound A fumarate. The invention provides Compound A mesylate. The invention provides Compound A hydrochloride. The invention provides Compound A malate. The invention provides Compound A sulfate. The invention provides Compound A L-tartrate. More particularly, the invention provides Compound A hemi-fumarate. The invention provides Compound A mono-fumarate. The invention provides Compound A mono-mesylate. The invention provides Compound A di-mesylate. The invention provides Compound A mono-hydrochloride. The invention provides Compound A di-hydrochloride.

The inventors discovered that many of these salts provide a desirable improvement in aqueous solubility of Compound A. For example, the mesylate and hydrochloride salts provided an unexpectedly large increase in solubility compared to the free base of Compound A, and were considered for further development. However, when taking into account a wider range of factors, Compound A fumarate was found to possess the best balance of properties.

Based on its advantageous properties, the mono-fumarate salt of Compound A was selected for further development. The fumarate salt of Compound A is only slightly hygroscopic. The fumarate salt of Compound A has aqueous solubility of from 0.05 to 4 mg/ml.

Polymorphs of Compound A

Form 1

In one aspect, the invention relates to Form 1 of Compound A. Form 1 is characterised by one or more of the following properties:

a) Form 1 exhibits an XRPD pattern with at least the following XRPD peaks (CuK ° 2θ) at approximately (±0.1): 12.9, 20.5, 21.2, 22.9, and 23.4;
b) Form 1 exhibits an XRPD pattern substantially the same as shown in FIG. 1;
c) Form 1 exhibits substantially the following unit cell parameters at 298 K:

| System | a | b | c | alpha | beta | gamma | A |
|---|---|---|---|---|---|---|---|
| Monoclinic P | 9.7(1) Å | 17.4(2) Å | 32.5(1) Å | 90 | 88.35 | 90 | 5483 $Å^3$ |

d) Form 1 exhibits a DTA-TGA thermogram comprising a major endotherm with onset temperature at around (±0.5) 238° C.;
e) Form 1 exhibits a DTA-TGA thermogram substantially the same as shown in FIG. 11;
f) Form 1 contains a 1:1 molar ratio of fumarate to Compound A (Form 1 is a stoichiometric fumarate);
g) Form 1 is an unsolvated crystalline form; and/or h) Form 1 is obtainable from 1-butanol, 1-propanol, 2-ethoxyethanol, acetone, acetonitrile, MEK, THF, 1,1-dimethoxymethane, or DMSO.

Form 1 may be characterised by at least a). Form 1 may be characterised by at least b). Form 1 may be characterised by at least c). Form 1 may be characterised by at least d). Form 1 may be characterised by at least e). Form 1 may be characterised by at least f). Form 1 may be characterised by at least g). Form 1 may be characterised by at least h).

Form 1 may be characterised by at least two of the above properties. Form 1 may be characterised by at least a) and b). Form 1 may be characterised by at least a) and c). Form 1 may be characterised by at least a) and d). Form 1 may be characterised by at least a) and e). Form 1 may be characterised by at least a) and f). Form 1 may be characterised by at least a) and g). Form 1 may be characterised by at least a) and h). Form 1 may be characterised by at least b) and c). Form 1 may be characterised by at least b) and d). Form 1 may be characterised by at least b) and e). Form 1 may be characterised by at least b) and f). Form 1 may be characterised by at least b) and g). Form 1 may be characterised by at least b) and h). Form 1 may be characterised by at least c) and d). Form 1 may be characterised by at least c) and e). Form 1 may be characterised by at least c) and f). Form 1 may be characterised by at least c) and g). Form 1 may be characterised by at least c) and h).

Form 1 may be characterised by at least three of the above properties. Form 1 may be characterised by at least four of the above properties. Form 1 may be characterised by at least five of the above properties. Form 1 may be characterised by at least six of the above properties. Form 1 may be characterised by at least seven of the above properties. Form 1 may be characterised by all of the above properties.

Preferably, Form 1 is characterised by at least one of a), b), and c). Form 1 may be characterised by at least one of a), b), and c), and d). Form 1 may be characterised by at least one of a), b), and c), and e). Form 1 may be characterised by at least one of a), b), and c), and f). Form 1 may be characterised by at least one of a), b), and c), and g). Form 1 may be characterised by at least one of a), b), and c), and h).

Preparation of Form 1

The invention provides processes of making or preparing Form 1. Form 1 can be prepared from a range of solvents. For example, Form 1 can be prepared from 1-butanol, 1-propanol, 2-ethoxyethanol, acetone, or acetonitrile, 1,1-dimethoxymethane, or dimethyl sulfoxide (DMSO).

Form 1 can be prepared by temperature cycling, evaporation, or post-solvent drop grinding. In one aspect, Form 1 can prepared from 1-butanol, 1-propanol, 2-ethoxyethanol, acetone, or acetonitrile by temperature cycling. In another aspect, Form 1 can be prepared from 1,1-dimethoxymethane or DMSO by post-solvent drop grinding.

Characterisation of Form 1

Form 1 is crystalline by XRPD, with characteristic peaks (CuK ° 2θ) at approximately (±0.1): 12.9, 20.5, 21.2, 22.9, and 23.4. For example, Form 1 may have characteristic peaks at approximately (±0.1): 12.9, 17.5, 20.5, 21.2, 22.9, 23.4, 26.8, and 27.1. For example, Form 1 may have characteristic peaks at approximately (±0.1): 5.9, 12.9, 17.5, 18.3, 19.6, 20.5, 21.2, 22.9, 23.4, 26.8, and 27.1.

Particles of Form 1 are weakly birefringent and comprised of fragmented plates, as shown in FIG. 21 and as determined by PLM. The consistent rounded shape of the Form 1 particles is advantageous as it allows for easier physical manipulation than other crystal shapes. This is particularly important in pharmaceutical processing. Round, consistent particles are preferable to e.g. long, thin or inconsistently shaped particles in this regard.

$^1$H NMR of Form 1 is consistent with the structure of Compound A and showed the expected connectivity. 1 equivalent of fumaric acid was observed by $^1$H NMR.

DTA/TG thermograms for Form 1 are shown in FIG. 11. Form 1 has an unsolvated crystal structure, as indicated by no significant weight loss at low temperatures in the thermogravimetric experiment. Unsolvated crystal forms are easier to work with than solvated forms, because the presence of solvent molecules in the lattice introduces a variability in analytical assaying which complicates their use as a pharmaceutical active. Furthermore, the reproducible absence of solvates avoids any potential dosing and toxicity complications.

DT analysis shows that Form 1 exhibits a small melt with an onset of ca. 227° C. relating to loss of fumarate, followed by the melt of the Compound A free base from an onset of ca. 237° C. (peak at 242° C.). The high melting temperature of the Form 1 lattice confirms its beneficial thermodynamic stability.

Form 1 is only slightly hygroscopic, with an uptake of 0.7 wt. % (0.07 equivalents of water) at 90% RH according to DVS. No evidence of form change by hydration or recrystallization was observed when the recovered solids were characterized by XRPD. See FIGS. 35 and 36.

A high purity of 99.7% (by area %) was observed by HPLC.

Stability experiments conducted on Form 1 showed no significant changes in form over a six month period or chemical composition over a 24 month period at ambient and accelerated conditions. Thus, Form 1 displays substantially the same characteristic peaks noted above after storage at 40° C./75% RH. Form 1 displays substantially the same XRPD as shown in FIG. 1 after storage at 40° C./75% RH.

Moreover, Form 1 is stable in a range of organic solvents—demonstrating no change in form (assessed by XRPD based on the characteristic peaks above and as shown in FIG. 1, and the unit cell described above) upon exposure to 1-butanol, 1-propanol, 2-ethoxyethanol, acetone, acetonitrile, MEK, THF, 1,1-dimethoxymethane, or DMSO. The chemical and physical stability, including a resistance to changing forms, in a range of environments indicates that Form 1 is particularly advantageous.

Form 2

In another aspect, the invention relates to Form 2 of Compound A. Form 2 is characterised by one or more of the following properties:

a) Form 2 exhibits an XRPD pattern with at least the following XRPD peaks (CuK 2θ) at approximately (±0.1): 15.4, 15.8, 16.3, and 24.5;

b) Form 2 exhibits an XRPD pattern substantially the same as shown in FIG. 2;

c) Form 2 exhibits substantially the following unit cell parameters at 298 K:

| System | a | b | c | alpha | beta | gamma |
|---|---|---|---|---|---|---|
| Triclinic P | 8.3(1) Å | 14.1(2) Å | 20.8(4) Å | 86.72 | 90.24 | 95.95 |

d) Form 2 exhibits a DTA-TGA thermogram comprising a major endotherm with onset temperature at around (±0.5) 231° C.;

e) Form 2 exhibits a DTA-TGA thermogram substantially the same as shown in FIG. 12;

f) Form 2 contains a 1:1 molar ratio of fumarate to Compound A (Form 2 is a stoichiometric fumarate);

g) Form 2 is an unsolvated crystalline form; and/or h) Form 2 is obtainable from 1,4-dioxane.

Form 2 may be characterised by at least a). Form 2 may be characterised by at least b). Form 2 may be characterised by at least c). Form 2 may be characterised by at least d). Form 2 may be characterised by at least e). Form 2 may be characterised by at least f). Form 2 may be characterised by at least g). Form 2 may be characterised by at least h).

Form 2 may be characterised by at least two of the above properties. Form 2 may be characterised by at least a) and b). Form 2 may be characterised by at least a) and c). Form 2 may be characterised by at least a) and d). Form 2 may be characterised by at least a) and e). Form 2 may be characterised by at least a) and f). Form 2 may be characterised by at least a) and g). Form 2 may be characterised by at least a) and h). Form 2 may be characterised by at least b) and c). Form 2 may be characterised by at least b) and d). Form 2 may be characterised by at least b) and e). Form 2 may be characterised by at least b) and f). Form 2 may be characterised by at least b) and g). Form 2 may be characterised by at least b) and h). Form 2 may be characterised by at least c) and d). Form 2 may be characterised by at least c) and e). Form 2 may be characterised by at least c) and f). Form 2 may be characterised by at least c) and g). Form 2 may be characterised by at least c) and h).

Form 2 may be characterised by at least three of the above properties. Form 2 may be characterised by at least four of the above properties. Form 2 may be characterised by at least five of the above properties. Form 2 may be characterised by at least six of the above properties. Form 2 may be characterised by at least seven of the above properties. Form 2 may be characterised by all of the above properties.

Preferably, Form 2 is characterised by at least one of a), b), and c). Form 2 may be characterised by at least one of a), b), and c), and d). Form 2 may be characterised by at least one of a), b), and c), and e). Form 2 may be characterised by at least one of a), b), and c), and f). Form 2 may be characterised by at least one of a), b), and c), and g). Form 2 may be characterised by at least one of a), b), and c), and h).

Preparation of Form 2

The invention provides processes of making or preparing Form 2. For example, Form 2 can be prepared from 1,4-dioxane. In one aspect, Form 2 can be prepared by drying of Form 4 in 1,4-dioxane. Form 2 can also be prepared by lyophilisation of Compound A fumarate (see FIG. 10).

Characterisation of Form 2

Form 2 is crystalline by XRPD, with characteristic peaks (CuK 2θ) at approximately (±0.1): 15.4, 15.8, 16.3, and 24.5; For example, Form 2 may have characteristic peaks at approximately (±0.1): 13.5, 15.4, 15.8, 16.3, 17.8, 24.5, 25.7, and 27.3. For example, Form 2 may have characteristic peaks at approximately (±0.1): 7.2, 9.3, 10.7, 13.5, 15.4, 15.8, 16.3, 17.8, 18.9, 24.5, 25.7, and 27.3.

Particles of Form 2 are highly birefringent with no defined morphology, as shown in FIG. 22 and as determined by PLM.

$^1$H NMR analysis of Form 2 is consistent with the structure of Compound A and showed the expected connectivity. 1 equivalent of fumaric acid was observed by $^1$H NMR.

DTA/TG thermograms for Form 2 are shown in FIG. 12. Form 2 has an unsolvated crystal structure, as indicated by no significant loss in mass until above approximately 120° C. Above 120° C. a continuous weight loss was observed, related to the potential loss of fumaric acid and onset of degradation. Form 2 has a complex thermal profile between ca. 120° C. and 230° C., and a large melting endotherm was observed from an onset of ca. 232° C. (peak at 239° C.).

Form 2 has unexpected stability in 1,4-dioxane and under lyophilisation conditions, (i.e. Form 2 exhibits no change in the characteristic XRPD peaks, spectra, or unit cell noted above in these conditions).

Form 3

In another aspect, the invention relates to Form 3 of Compound A. Form 3 is characterised by one or more of the following properties:

a) Form 3 exhibits an XRPD pattern with at least the following XRPD peaks (CuK 2θ) at approximately (±0.1): 8.8, 17.4, 17.7, and 18.2;

b) Form 3 exhibits an XRPD pattern substantially the same as shown in FIG. 3;

c) Form 3 exhibits substantially the following unit cell parameters at 298 K:

| System | a | b | c | alpha | beta | gamma | A |
|---|---|---|---|---|---|---|---|
| Triclinic P | 9.7(2) Å | 12.7(3) Å | 24.6(3) Å | 78.92 | 86.15 | 102.2 | 2888 Å$^3$ |

d) Form 3 exhibits a DTA-TGA thermogram comprising a major endotherm with onset temperature at around (±0.5) 184° C.;

e) Form 3 exhibits a DTA-TGA thermogram substantially the same as shown in FIG. 13;

f) Form 3 contains a 1:2 molar ratio of fumarate to Compound A (Form 3 is a hemi-fumarate);

g) Form 3 is an monohydrate (1:1 molar ratio of water to Compound A); and/or h) Form 3 is obtainable from dimethoxymethane, 2-MeTHF, water:methanol (0:100, 40:60, 80:20, 95:5, 100:0), EtOAc IPA, MEK, MIBK, THF, acetone, acetonitrile.

Form 3 may be characterised by at least a). Form 3 may be characterised by at least b). Form 3 may be characterised by at least c). Form 3 may be characterised by at least d). Form 3 may be characterised by at least e). Form 3 may be characterised by at least f). Form 3 may be characterised by at least g). Form 3 may be characterised by at least h).

Form 3 may be characterised by at least two of the above properties. Form 3 may be characterised by at least a) and b). Form 3 may be characterised by at least a) and c). Form 3 may be characterised by at least a) and d). Form 3 may be characterised by at least a) and e). Form 3 may be characterised by at least a) and f). Form 3 may be characterised by at least a) and g). Form 3 may be characterised by at least a) and h). Form 3 may be characterised by at least b) and c). Form 3 may be characterised by at least b) and d). Form 3 may be characterised by at least b) and e). Form 3 may be characterised by at least b) and f). Form 3 may be characterised by at least b) and g). Form 3 may be characterised by at least b) and h). Form 3 may be characterised by at least c) and d). Form 3 may be characterised by at least c) and e). Form 3 may be characterised by at least c) and f). Form 3 may be characterised by at least c) and g). Form 3 may be characterised by at least c) and h).

Form 3 may be characterised by at least three of the above properties. Form 3 may be characterised by at least four of the above properties. Form 3 may be characterised by at least five of the above properties. Form 3 may be characterised by at least six of the above properties. Form 3 may be characterised by at least seven of the above properties. Form 3 may be characterised by all of the above properties.

Preferably, Form 3 is characterised by at least one of a), b), and c). Form 3 may be characterised by at least one of a), b), and c), and d). Form 3 may be characterised by at least one of a), b), and c), and e). Form 3 may be characterised by at least one of a), b), and c), and f). Form 3 may be characterised by at least one of a), b), and c), and g). Form 3 may be characterised by at least one of a), b), and c), and h).

Preparation of Form 3

The invention provides processes of making or preparing Form 3. Form 3 can be prepared from a range of solvents. For example, Form 3 can be prepared from: dimethoxymethane; 2-MeTHF; water:MeOH (0:100, 40:60, 80:20, 95:5, 100:0); EtOAc; IPA; MEK; MIBK; THF; acetone; or acetonitrile.

Form 3 can be prepared by temperature cycling, evaporation, or anti-solvent addition. In one aspect, Form 3 can prepared from: dimethoxymethane; 2-MeTHF; water:MeOH (0:100, 40:60, 80:20, 95:5, 100:0); IPA; by temperature cycling. In another aspect, Form 3 can be prepared from: water:MeOH (0:100, 40:60, 80:20, 95:5, 100:0); EtOAc; MEK; acetone; or acetonitrile by evaporation. In another aspect, Form 3 can be prepared from THE and TMBE by anti-solvent addition.

Characterisation of Form 3

Form 3 is crystalline by XRPD, with characteristic (CuK 2θ) at approximately (±0.1): 8.8, 17.4, 17.7, and 18.2. For example, Form 3 may have characteristic peaks at approximately (±0.1): 8.8, 15.6, 17.4, 17.7, 18.2, and 22.5. For example, Form 3 may have characteristic peaks at approximately (±0.1): 3.7, 7.4, 8.8, 15.6, 17.4, 17.7, 18.2, 22.5, 26.8, and 27.0.

Particles of Form 3 are rods and agglomerated particles, as shown in FIG. 23 and as determined by PLM.

$^1$H NMR analysis of Form 3 is consistent with the structure of Compound A and showed the expected connectivity. Approximately 0.5 equivalents of fumaric acid were observed indicating the material is a hemi-fumarate salt.

DTA/TG thermograms for Form 3 are shown in FIG. 13. Form 3 is a monohydrate, as indicated by a mass loss of 3.3% (1.1 equivalent of water) from ca. 80 to 110° C. and associated endotherm with onset ca. 65° C. (peak at 110° C.). A further mass loss of ca. 10.3% and a sharp endothermic event was observed from an onset of ca. 184° C. (peak at 188° C.) potentially related to the loss of fumaric acid or the onset of degradation. From ca. 231° C., Form 3 has a complex thermal profile.

Form 3 is only slightly hygroscopic, as shown by DVS with a weight increase of ca. 0.5 wt. % at 90% RH. No evidence of hydration or dehydration was observed.

Form 3 is stable at ambient and stressed conditions (40° C./75% RH (open vial), and 80° C. (closed vial)), with no changes in appearance, purity or XRPD pattern after 1 week at these conditions. Form 3 can be handled in organic solvents without change in form (i.e. no change in the characteristic XRPD peaks, spectra, or unit cell noted above), for example: dimethoxymethane; 2-MeTHF; water: MeOH (0:100, 40:60, 80:20, 95:5, 100:0); EtOAc; IPA; MEK; MIBK; THF; acetone; or acetonitrile.

Form 4

In another aspect, the invention relates to Form 4 of Compound A. Form 4 is characterised by one or more of the following properties:

a) Form 4 exhibits an XRPD pattern with at least the following XRPD peaks (CuK 2θ) at approximately (±0.1): 16.3, 18.7, 22.8, 23.1, and 25.7;
b) Form 4 exhibits an XRPD pattern substantially the same as shown in FIG. 4;
c) Form 4 exhibits a DTA-TGA thermogram comprising a major endotherm with onset temperature at around (±0.5) 142° C.;
d) Form 4 exhibits a DTA-TGA thermogram substantially the same as shown in FIG. 14;
e) Form 4 contains a 1:1 molar ratio of fumarate to Compound A (Form 4 is a stoichiometric fumarate); and/or
f) Form 4 is a 1,4-dioxane solvate;

Form 4 may be characterised by at least a). Form 4 may be characterised by at least b). Form 4 may be characterised by at least c). Form 4 may be characterised by at least d). Form 4 may be characterised by at least e). Form 4 may be characterised by at least f).

Form 4 may be characterised by at least two of the above properties. Form 4 may be characterised by at least a) and b). Form 4 may be characterised by at least a) and c). Form 4 may be characterised by at least a) and d). Form 4 may be characterised by at least a) and e). Form 4 may be characterised by at least a) and f). Form 4 may be characterised by at least b) and c). Form 4 may be characterised by at least b) and d). Form 4 may be characterised by at least b) and e). Form 4 may be characterised by at least b) and f). Form 4 may be characterised by at least c) and d). Form 4 may be characterised by at least c) and e). Form 4 may be characterised by at least c) and f). Form 4 may be characterised by at least d) and e). Form 4 may be characterised by at least e) and f).

Form 4 may be characterised by at least three of the above properties. Form 4 may be characterised by at least four of the above properties. Form 4 may be characterised by at least five of the above properties. Form 4 may be characterised by all of the above properties.

Preferably, Form 4 is characterised by at least one of a) and b). Form 3 may be characterised by at least one of a) and b), and c). Form 4 may be characterised by at least one of a) and b), and d). Form 4 may be characterised by at least one of a) and b), and e). Form 4 may be characterised by at least one of a) and b), and f).

Form 4 is preferably characterised by at least a) and/or b). Form 4 is stable in organic solvents such as 1,4-dioxane (i.e. exhibits no change in the characteristic XRPD peaks, or spectra noted above).

Form 5

In another aspect, the invention relates to Form 5 of Compound A. Form 5 is characterised by one or more of the following properties:

a) Form 5 exhibits an XRPD pattern with at least the following XRPD peaks (CuK 2θ) at approximately (±0.1): 21.5, 24.5, and 27.3;

b) Form 5 exhibits an XRPD pattern substantially the same as shown in FIG. 5;

c) Form 5 exhibits substantially the following unit cell parameters at 298 K:

| System | a | b | c | alpha | beta | gamma |
|---|---|---|---|---|---|---|
| Monoclinic P | 32.06(5) Å | 11.28(1) Å | 8.43(1) Å | 90 | 93.65 (2) | 90 |

d) Form 5 exhibits a DTA thermogram comprising a major endotherm with onset temperature at around (±0.5) 229° C.;

e) Form 5 exhibits a DTA thermogram substantially the same as shown in FIG. 15;

f) Form 5 contains a 1:2 molar ratio of fumarate to Compound A (Form 5 is a hemi-fumarate);

g) Form 5 is a benzyl alcohol solvate; and/or h) Form 5 is obtainable from benzyl alcohol.

Form 5 may be characterised by at least a). Form 5 may be characterised by at least b). Form 5 may be characterised by at least c). Form 5 may be characterised by at least d). Form 5 may be characterised by at least e). Form 5 may be characterised by at least f). Form 5 may be characterised by at least g). Form 5 may be characterised by at least h).

Form 5 may be characterised by at least two of the above properties. Form 5 may be characterised by at least a) and b). Form 5 may be characterised by at least a) and c). Form 5 may be characterised by at least a) and d). Form 5 may be characterised by at least a) and e). Form 5 may be characterised by at least a) and f). Form 5 may be characterised by at least a) and g). Form 5 may be characterised by at least a) and h). Form 5 may be characterised by at least b) and c). Form 5 may be characterised by at least b) and d). Form 5 may be characterised by at least b) and e). Form 5 may be characterised by at least b) and f). Form 5 may be characterised by at least b) and g). Form 5 may be characterised by at least b) and h). Form 5 may be characterised by at least c) and d). Form 5 may be characterised by at least c) and e). Form 5 may be characterised by at least c) and f). Form 5 may be characterised by at least c) and g). Form 5 may be characterised by at least c) and h).

Form 5 may be characterised by at least three of the above properties. Form 5 may be characterised by at least four of the above properties. Form 5 may be characterised by at least five of the above properties. Form 5 may be characterised by at least six of the above properties. Form 5 may be characterised by at least seven of the above properties. Form 5 may be characterised by all of the above properties.

Preferably, Form 5 is characterised by at least one of a), b), and c). Form 5 may be characterised by at least one of a), b), and c), and d). Form 5 may be characterised by at least one of a), b), and c), and e). Form 5 may be characterised by at least one of a), b), and c), and f). Form 5 may be characterised by at least one of a), b), and c), and g). Form 5 may be characterised by at least one of a), b), and c), and h).

Preparation of Form 5

The invention provides processes of making or preparing Form 5. Form 5 can be prepared from benzyl alcohol. Form 5 can be prepared by temperature cycling, or post-solvent drop grinding. In one aspect, Form 5 can prepared from benzyl alcohol by temperature cycling. In another aspect, Form 5 can be prepared from benzyl alcohol by post-solvent drop grinding.

Characterisation of Form 5

Form 5 is crystalline by XRPD, with characteristic peaks at (CuK 2θ) at approximately (±0.1): 21.5, 24.5, and 27.3. For example, Form 5 may have characteristic peaks at approximately (±0.1): 21.5, 22.2, 22.4, 23.2, 24.5, and 27.3. For example, Form 5 may have characteristic peaks at approximately (±0.1): 15.7, 15.9, 16.6, 21.5, 22.2, 22.4, 23.2, 24.5, and 27.3.

Particles of Form 5 are highly birefringent rods and agglomerated particles, as shown in FIG. 25 and as determined by PLM.

$^1$H NMR analysis of Form 5 is consistent with the structure of Compound A and showed the expected connectivity. Approximately 0.5 equivalents of fumaric acid were observed indicating the material is a hemi-fumarate salt. The $^1$H NMR of Form 5 displayed peaks characteristic of benzyl alcohol.

DTA/TG thermograms for Form 5 are shown in FIG. 15. Form 5 is a benzyl alcohol solvate, as indicated by mass loss of 41.7% (3.8 equiv. of benzyl alcohol) from the onset of heating up to approximately 135° C. and a broad endothermic event from an onset of ca. 120° C. (peak at 136° C.). Form 5 displays a sharp melting endotherm from an onset of ca. 229° C. (peak at 236° C.).

Form 5 can be handled in organic solvents such as benzyl alcohol without any change in form ((i.e. Form 5 exhibits no change in the characteristic XRPD peaks, spectra, or unit cell noted above in these conditions).

Form 6

In another aspect, the invention relates to Form 6 of Compound A. Form 6 is characterised by one or more of the following properties:

a) Form 6 exhibits an XRPD pattern with at least the following XRPD peaks (CuK 2θ) at approximately (±0.1): 9.1, 9.4, 9.8, 16.0, and 26.4;

b) Form 6 exhibits an XRPD pattern substantially the same as shown in FIG. 6;

c) Form 6 exhibits substantially the following unit cell parameters at 298 K:

| System | a | b | c | alpha | beta | gamma |
|---|---|---|---|---|---|---|
| Monoclinic P | 13.07 Å | 18.78 Å | 11.08 Å | 90 | 118.62 | 90 |

d) Form 6 is a free base of Compound A;

e) Form 6 is a DMSO solvate; and/or f) Form 6 is obtainable from DMSO.

Form 6 may be characterised by at least a). Form 6 may be characterised by at least b). Form 6 may be characterised by at least c). Form 6 may be characterised by at least d). Form 6 may be characterised by at least e). Form 6 may be characterised by at least f).

Form 6 may be characterised by at least two of the above properties. Form 6 may be characterised by at least a) and b). Form 6 may be characterised by at least a) and c). Form 6 may be characterised by at least a) and d). Form 6 may be characterised by at least a) and e). Form 6 may be characterised by at least a) and f). Form 6 may be characterised by at least b) and c). Form 6 may be characterised by at least b) and d). Form 6 may be characterised by at least b) and e). Form 6 may be characterised by at least b) and f). Form 6 may be characterised by at least c) and d). Form 6 may be characterised by at least c) and e) Form 6 may be characterised by at least c) and f). Form 6 may be characterised by at least d) and e). Form 6 may be characterised by at least d) and f). Form 6 may be characterised by at least e) and f).

Form 6 may be characterised by at least three of the above properties. Form 6 may be characterised by at least four of the above properties. Form 6 may be characterised by all of the above properties.

Preferably, Form 6 is characterised by at least one of a), b), and c). Form 6 may be characterised by at least one of a), b), and c), and d). Form 6 may be characterised by at least one of a), b), and c), and e). Form 6 may be characterised by at least one of a), b), and c), and f).

Preparation of Form 6

The invention provides processes of making or preparing Form 6. For example, Form 6 can be prepared from DMSO. In one aspect, Form 6 can be prepared from DMSO by temperature cycling.

Characterisation of Form 6

Form 6 is crystalline by XRPD, with characteristic peaks at (CuK 2θ) at approximately (±0.1): 9.1, 9.4, 9.8, 16.0, and 26.4. For example, Form 6 may have characteristic peaks at approximately (±0.1): 9.1, 9.4, 9.8, 12.7, 16.0, 20.4, 21.0, and 26.4. For example, Form 6 may have characteristic peaks at approximately (±0.1): 9.1, 9.4, 9.8, 12.7, 16.0, 20.4, 21.0, 24.5, 25.2, and 26.4.

$^1$H NMR analysis of Form 6 is consistent with the structure of Compound A and showed the expected connectivity. The $^1$H NMR of Form 6 displayed peaks characteristic of DMSO.

Form 6 can be handled in DMSO without any change in form (i.e. Form 6 exhibits no change in the characteristic XRPD peaks, spectra, or unit cell noted above in these conditions).

Form 7

In another aspect, the invention relates to Form 7 of Compound A. Form 7 is characterised by one or more of the following properties:

a) Form 7 exhibits an XRPD pattern with at least the following XRPD peaks (CuK 2θ) at approximately (±0.1): 7.5, 7.9, 25.6, and 26.2;
b) Form 7 exhibits an XRPD pattern substantially the same as shown in FIG. 7;
c) Form 7 exhibits substantially the following unit cell parameters at 298 K:

| System | a | b | c | alpha | beta | Gamma |
|---|---|---|---|---|---|---|
| Triclinic P | 13.86 Å | 20.54 Å | 7.98 Å | 96.12 | 93.2 | 92.4 |

d) Form 7 exhibits a DTA thermogram comprising a major endotherm with onset temperature at around (±0.5) 240° C.;
e) Form 7 exhibits a DTA thermogram substantially the same as shown in FIG. 16;
f) Form 7 is unsolvated;
g) Form 7 is a free base of Compound A; and/or
h) Form 7 is obtainable on drying Form 6 or from methanol.

Form 7 may be characterised by at least a). Form 7 may be characterised by at least b). Form 7 may be characterised by at least c). Form 7 may be characterised by at least d). Form 7 may be characterised by at least e). Form 7 may be characterised by at least f). Form 7 may be characterised by at least g). Form 7 may be characterised by at least h).

Form 7 may be characterised by at least two of the above properties. Form 7 may be characterised by at least a) and b). Form 7 may be characterised by at least a) and c). Form 7 may be characterised by at least a) and d). Form 7 may be characterised by at least a) and e). Form 7 may be characterised by at least a) and f). Form 7 may be characterised by at least a) and g). Form 7 may be characterised by at least a) and h). Form 7 may be characterised by at least b) and c). Form 7 may be characterised by at least b) and d). Form 7 may be characterised by at least b) and e). Form 7 may be characterised by at least b) and f). Form 7 may be characterised by at least b) and g). Form 7 may be characterised by at least b) and h). Form 7 may be characterised by at least c) and d). Form 7 may be characterised by at least c) and e). Form 7 may be characterised by at least c) and f). Form 7 may be characterised by at least c) and g). Form 7 may be characterised by at least c) and h).

Form 7 may be characterised by at least three of the above properties. Form 7 may be characterised by at least four of the above properties. Form 7 may be characterised by at least five of the above properties. Form 7 may be characterised by at least six of the above properties. Form 7 may be characterised by at least seven of the above properties. Form 7 may be characterised by all of the above properties.

Preferably, Form 7 is characterised by at least one of a), b), and c). Form 7 may be characterised by at least one of a), b), and c), and d). Form 7 may be characterised by at least one of a), b), and c), and e). Form 7 may be characterised by at least one of a), b), and c), and f). Form 7 may be characterised by at least one of a), b), and c), and g). Form 7 may be characterised by at least one of a), b), and c), and h).

Preparation of Form 7

The invention provides processes of making or preparing Form 7. Form 7 can be prepared by drying Form 6. Form 7 can be prepared by slurrying Form 6 in TBME. Alternatively, Form 7 can be prepared from methanol. In one aspect, Form 7 can be prepared from methanol by temperature cycling.

Characterisation of Form 7

Form 7 is crystalline by XRPD, with characteristic peaks at (CuK 2θ) at approximately (±0.1): 7.5, 7.9, 25.6, and 26.2. For example, Form 7 may have characteristic peaks at approximately (±0.1): 4.3, 6.4, 7.5, 7.9, 14.4, 19.9, 25.6, and 26.2. For example, Form 7 may have characteristic peaks at approximately (±0.1): 4.3, 6.4, 7.5, 7.9, 14.4, 15.7, 16.2, 18.5, 19.9, 22.2, 25.6, and 26.2.

Particles of Form 7 are highly birefringent rods and agglomerated particles, as shown in FIG. 26 and as determined by PLM.

$^1$H NMR analysis of Form 7 is consistent with the structure of Compound A and showed the expected connectivity. Form 7 displays no fumaric acid peaks by NMR, indicating the material is Compound A free base. This provides a higher active content than other forms. In some embodiments, low levels of fumarate may be detected as an impurity in the Form 7 material.

DTA/TG thermograms for Form 7 are shown in FIG. 16. Form 7 displays a sharp melting endotherm from an onset of ca. 241° C. (peak at 244° C.), indicating a thermodynamically favourable lattice. Mass loss at low temperatures related to removal of surface moisture and solvent.

Form 7 can be handled in organic solvents such as methanol and TBME without any change in form (i.e. Form 7 exhibits no change in the characteristic XRPD peaks, spectra, or unit cell noted above in these conditions). Form 7 is only slightly hygroscopic, and is stable under long term-storage conditions.

Form 8

In another aspect, the invention relates to Form 8 of Compound A. Form 8 is characterised by one or more of the following properties:

a) Form 8 exhibits an XRPD pattern with at least the following XRPD peaks (CuK 2θ) at approximately (±0.1): 10.4, 10.7, 11.1, 24.2, and 24.5;

b) Form 8 exhibits an XRPD pattern substantially the same as shown in FIG. 8;

c) Form 8 exhibits substantially the following unit cell parameters at 298 K:

| System | A | b | c | alpha | beta | gamma |
|---|---|---|---|---|---|---|
| Monoclinic P | 10.67 Å | 14.15 Å | 16.19 Å | 90 | 97.31 | 90 |

d) Form 8 exhibits a DTA thermogram comprising a major endotherm with onset temperature at around (±0.5) 232° C.;

e) Form 8 exhibits a DTA thermogram substantially the same as shown in FIG. 17.

f) Form 8 is a benzyl alcohol solvate;

g) Form 8 contains a 1:1 molar ratio of fumarate to Compound A (Form 8 is a stoichiometric fumarate); and/or h) Form 8 is obtainable from benzyl alcohol.

Form 8 may be characterised by at least a). Form 8 may be characterised by at least b). Form 8 may be characterised by at least c). Form 8 may be characterised by at least d). Form 8 may be characterised by at least e). Form 8 may be characterised by at least f). Form 8 may be characterised by at least g). Form 8 may be characterised by at least h).

Form 8 may be characterised by at least two of the above properties. Form 8 may be characterised by at least a) and b). Form 8 may be characterised by at least a) and c). Form 8 may be characterised by at least a) and d). Form 8 may be characterised by at least a) and e). Form 8 may be characterised by at least a) and f). Form 8 may be characterised by at least a) and g). Form 8 may be characterised by at least a) and h). Form 8 may be characterised by at least b) and c). Form 8 may be characterised by at least b) and d). Form 8 may be characterised by at least b) and e). Form 8 may be characterised by at least b) and f). Form 8 may be characterised by at least b) and g). Form 8 may be characterised by at least b) and h). Form 8 may be characterised by at least c) and d). Form 8 may be characterised by at least c) and e). Form 8 may be characterised by at least c) and f). Form 8 may be characterised by at least c) and g). Form 8 may be characterised by at least c) and h).

Form 8 may be characterised by at least three of the above properties. Form 8 may be characterised by at least four of the above properties. Form 8 may be characterised by at least five of the above properties. Form 8 may be characterised by at least six of the above properties. Form 8 may be characterised by at least seven of the above properties. Form 8 may be characterised by all of the above properties.

Preferably, Form 8 is characterised by at least one of a), b), and c). Form 8 may be characterised by at least one of a), b), and c), and d). Form 8 may be characterised by at least one of a), b), and c), and e). Form 8 may be characterised by at least one of a), b), and c), and f). Form 8 may be characterised by at least one of a), b), and c), and g). Form 8 may be characterised by at least one of a), b), and c), and h).

Preparation of Form 8

The invention provides processes of making or preparing Form 8. Form 8 can be prepared from benzyl alcohol. In one aspect, Form 8 can be prepared from benzyl alcohol by solvent drop grinding. Optionally, excess benzyl alcohol can be removed by slurrying in tert-butylmethyl ether.

Characterisation of Form 8

Form 8 is crystalline by XRPD, with characteristic peaks at (CuK 2θ) at approximately (±0.1): 10.4, 10.7, 11.1, 24.2, and 24.5. For example, Form 8 may have characteristic peaks at approximately (±0.1): 5.2, 5.5, 10.4, 10.7, 11.1, 15.5, 16.5, 24.2, and 24.5. For example, Form 8 may have characteristic peaks at approximately (±0.1): 5.2, 5.5, 8.2, 10.4, 10.7, 11.1, 15.5, 16.5, 21.4, 23.3, 24.2, and 24.5.

Particles of Form 8 are highly birefringent agglomerates with no defined morphology, as shown in FIG. 27 and as determined by PLM.

$^1$H NMR analysis of Form 8 is consistent with the structure of Compound A and showed the expected connectivity. Approximately 1 equivalent of fumaric acid was observed. The $^1$H NMR of Form 8 displays peaks characteristic of benzyl alcohol.

DTA/TG thermograms for Form 8 are shown in FIG. 17. Form 8 displays loss of mass up to ~120° C. (corresponding to removal of benzyl alcohol). Form 8 displays a sharp melting endotherm from an onset of ca. 232° C. (peak at 240° C.). Mass loss at low temperatures related to removal of surface moisture and solvent.

DEFINITIONS

"Compound A" refers to a compound having the chemical name: 6-chloro-7-(4-(4-chlorobenzyl)piperazin-1-yl)-2-(1,3-dimethyl-1H-pyrazol-4-yl)-3H-imidazo[4,5-b]pyridine. The compound has CAS No. 1402709-93-6. For the avoidance of doubt, unless stated to the contrary, reference to Compound A, or the "compound" is a reference to this compound having the structure above, optionally in the form of a pharmaceutically acceptable salt and/or solvate.

A salt of Compound A refers to the product of Compound A with an acidic or basic compound to form an ionic pair. Without wishing to be bound by any theory, the compounds of Formula (I) are capable of forming acid salts by virtue of the presence of nitrogen-containing groups that can accept one or more protons from an acidic moiety.

Compound A can form salts in a variety of molar ratios, for example a 1:1, or a 1:2 molar ratio of the acidic salt-forming moiety:Compound A. In this context, "Compound A" encompasses the ionic species formed e.g. from protonation of Compound A. For example, a 1:1 molar ratio of fumarate:Compound A would result from reaction of a 1:1 ratio of fumaric acid and Compound A.

Preferably, the pharmaceutically acceptable salt of Compound A is a fumarate salt, for example a stoichiometric fumarate or a hemi fumarate, preferably a stoichiometric fumarate (1:1 molar ratio of the Compound A:fumarate).

The crystalline forms of the present invention can exist in both unsolvated and solvated forms. The term "solvate" is used herein to describe a molecular complex comprising an API such as Compound A and an amount of one or more pharmaceutically acceptable solvents. Where the solvent is water the term "hydrate" is used. In the case of crystalline forms, the solvent may be interspersed throughout the lattice through intermolecular interactions.

The term "pharmaceutically acceptable excipient" as used herein, refers to a material, such as a carrier, diluent, stabilizer, dispersing agent, suspending agent, thickening agent, etc. which allows processing the active pharmaceutical ingredient (API) into a form suitable for administration to a mammal such as a human. Pharmaceutically acceptable excipients refer to materials which do not substantially abrogate the desired biological activity or desired properties of the compound (i.e. API), and is relatively nontoxic, i.e., the material is administered to an individual without causing undesirable biological effects or interacting in a deleterious manner with any of the components of the composition in which it is contained.

"Active pharmaceutical ingredient" or API refers to a compound that possesses a desired biological activity or desired properties. In the present invention, the API is Compound A. In some embodiments, the API has a purity of greater than 90%, greater than 95%, greater than 96%, greater than 97%, greater than 98%, greater than 98%, or greater than 99%.

The term "pharmaceutical composition" refers to a mixture of Compound A, or pharmaceutically acceptable salt and/or solvate thereof, with other chemical components, such as carriers, stabilizers, diluents, dispersing agents, suspending agents, thickening agents, excipients, etc. The pharmaceutical composition facilitates administration of the compound to a mammal.

The term "acceptable" with respect to a formulation, composition or ingredient, as used herein, means having no persistent detrimental effect on the general health of the subject being treated.

The terms "effective amount" or "therapeutically effective amount," as used herein, refer to a sufficient amount of an agent being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. The term "therapeutically effective amount" includes, for example, a prophylactically effective amount. The effective amount will be selected based on the particular patient and the disease level. It is understood that "an effect amount" or "a therapeutically effective amount" varies from subject to subject, due to variation in metabolism of drug, age, weight, general condition of the subject, the condition being treated, the severity of the condition being treated, and the judgment of the prescribing physician. In one embodiment, an appropriate "effective" amount in any individual case is determined using techniques, such as a dose escalation study.

"Substantially", "approximately", "about" etc. as applied to terms herein is understood to account for the natural degree of variation in a given parameter. For example, a person skilled in the art of XRPD comparing two spectra which are said to be "substantially the same" would focus on the major, characterising peaks, and certainly would not expect the two spectra to be identical. In other words, "substantially" is consistent with the degree of variation inherent in spectroscopic techniques such as XRPD. The unit cell parameters, which are determined from the diffraction data, are similarly subject to variation. For example, "substantially", "approximately", "about" etc. may be understood to refer to variation within the degree of significance reported. By way of example, a value of substantially, approximately, or about 60 would encompass from at least 55 to less than 65, whereas a value of substantially, approximately, or about 60.0 would encompass from at least 59.5 to less than 60.5.

The term "subject" or "patient" encompasses mammals. In a preferred aspect, the mammal is a human. In another aspect, the mammal is a non-human primate such as chimpanzee, and other apes and monkey species. In one aspect, the mammal is a farm animal such as cattle, horse, sheep, goat, or swine. In one aspect, the mammal is a domestic animal such as rabbit, dog, or cat. In one aspect, the mammal is a laboratory animal, including rodents, such as rats, mice and guinea pigs, and the like.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions/Formulations

According to a further aspect of the invention there is provided a pharmaceutical composition which comprises a salt and/or polymorph of Compound A as defined herein. The pharmaceutical composition may further comprise a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing). Preferably, the dosage form is a hard or soft capsule.

The compositions of the invention may be obtained by conventional procedures using conventional pharmaceutical excipients, well known in the art. For example, compositions intended for oral use may contain, for example, one or more colouring, sweetening, flavouring and/or preservative agents. Suitable techniques, carriers, and excipients include those found within, for example, *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), herein incorporated by reference in their entirety.

An effective amount of Compound A for use in therapy of proliferative disease is an amount sufficient to symptomatically relieve in a warm-blooded animal, particularly a human the symptoms of infection, to slow the progression of infection, or to reduce in patients with symptoms of infection the risk of getting worse.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent, for example from 10 to 150 mg, such as 20, 50 or 100 mg of Compound A (according to the weight of free base) compounded with an appropriate and convenient amount of excipients which may vary from about 5 to about 98 percent by weight of the total composition.

The size of the dose for therapeutic or prophylactic purposes of Compound A will naturally vary according to the nature and severity of the conditions, the age and sex of the animal or patient and the route of administration, according to well-known principles of medicine. Contemplated pharmaceutical compositions provide a therapeutically effective amount of Compound A enabling, for example, once-a-day, twice-a-day, three times a day, etc. administration.

Therapeutic Uses and Applications

The salts and/or polymorphs of Compound A of the invention are inhibitors of Aurora kinase and FLT3 activity.

Thus, the present invention also provides one or more salts and/or polymorphs of Compound A, or a pharmaceutical composition as defined herein, for use in the treatment of diseases or conditions in which Aurora kinase and/or FLT3 activity is implicated.

The present invention also provides the use of one or more salts and/or polymorphs of Compound A as defined herein, in the manufacture of a medicament for use in the treatment of diseases or conditions in which Aurora kinase and/or FLT3 activity is implicated.

The present invention also provides a method of treating a disease or condition in which Aurora kinase and/or FLT3 activity is implicated, said method comprising administering to a subject in need of such treatment a therapeutically effective amount of one or more salts and/or polymorphs of Compound A, or a pharmaceutical composition as defined herein.

The present invention also provides a one or more salts and/or polymorphs of Compound A for use in the treatment of a proliferative disorder, such as cancer. In a particular embodiment, the cancer is a human cancer.

The present invention also provides the use of one or more salts and/or polymorphs of Compound A in the manufacture of a medicament for use in the treatment of a proliferative disorder, such as cancer. In a particular embodiment, the cancer is a human cancer.

The present invention also provides a method of treating a proliferative disorder, such as cancer, said method comprising administering to a subject in need of such treatment a therapeutically effective amount of one or more salts and/or polymorphs of Compound A, or a pharmaceutical composition as defined herein. In a particular embodiment, the cancer is a human cancer.

The present invention also provides one or more salts and/or polymorphs of Compound A for use in the production of an Aurora kinase and/or FLT3 inhibitory effect.

The present invention provides the use of a compound, or a pharmaceutically acceptable salt or solvate thereof, in the manufacture of a medicament for use in the production of an Aurora kinase and/or FLT3 inhibitory effect.

The present invention also provides a method of producing an in vitro or in vivo Aurora kinase and/or FLT3 inhibitory effect, said method comprising administering an effective amount of one or more salts and/or polymorphs of Compound A.

The present invention also provides a method of inhibiting cell proliferation in vitro or in vivo, said method comprising contacting a cell with an effective amount of a compound as defined herein, or a pharmaceutically acceptable salt or solvate thereof.

Processes and Methods Involving the Claimed Invention

The invention provides processes for the preparation of the crystalline forms of Compound A. Thus, the invention provides a process for the preparation of any of Forms 1, 2, 3, 4, 5, 6, 7, and 8 comprising the crystallisation of that form from Compound A. In a preferred embodiment, the process comprises lyophilising Compound A fumarate, and optionally exposing the lyophile to one or more solvents.

The process may further comprise crystallising a form of Compound A using one of the crystallisation techniques described herein. For example, the process may comprise crystallising a form of Compound A by temperature cycling, anti-solvent addition, crash cooling, evaporation, and/or solvent drop grinding. In one embodiment, the crystallisation technique is temperature cycling. In one embodiment, the crystallisation technique is anti-solvent addition. In one embodiment, the crystallisation technique is crash cooling. In one embodiment, the crystallisation technique is evaporation. In one embodiment, the crystallisation technique is solvent drop grinding.

Owing to their advantageous properties, the claimed salts and/or polymorphs are useful in the manufacturing process for Compound A and pharmaceutical formulations thereof. Thus, the invention also provides processes for formulating a pharmaceutical composition comprising Compound A, wherein the process involves one or more salts and/or polymorphs of Compound A described herein. The process may comprise:

a) synthesising a salt and/or polymorph of Compound A;
b) storing a salt and/or polymorph of Compound A, for example prior to or after manufacture of the final pharmaceutical form or composition;
c) Analysing a salt and/or polymorph of Compound A, for example by one of the techniques described herein such as XRPD, NMR, DSC, DTA, TG, and/or DVS; and/or
d) formulating a salt and/or polymorph of Compound A into a pharmaceutical composition, optionally wherein the pharmaceutical composition is selected from the group consisting of: tablets, lozenges, hard or soft capsules, solid dispersions, aqueous or oily suspensions, emulsions, dispersible powders or granules, syrups or elixirs, creams, ointments, gels, or aqueous or oily solutions or suspensions, liquid aerosols, sterile aqueous or oily solution, or suppository.

The process may comprise any or all of the steps a)-d) above. For example, the process may comprise: steps a) and b); steps a) and c); steps a) and d); steps b) and c); steps b) and d); steps c) and d); steps a), b) and c); steps a), b) and d); steps a), c) and d); steps b), c) and d); or steps a), b), c) and d).

Formulating may be by any means known in the art, for example tabletting, compacting, granulating (wet or dry) micronizing, capsule filing, dissolving, dispersing, emulsifying spray drying, melt extruding, and/or lyophilising. The final composition may comprise any form of Compound A described herein, for example Form 1, Form 2, Form 3, Form 4, Form 5, Form 6, Form 7, Form 8, or amorphous Compound A.

The invention also provides compositions made by these processes.

EXAMPLES

Methods of Analysis

X-Ray Powder Diffraction (XRPD)

XRPD analysis was carried out on a PANalytical X'pert pro with PIXcel detector (128 channels), scanning the samples between 3 and 35° 2θ. The material was gently ground to release any agglomerates and loaded onto a multi-well plate with Kapton or Mylar polymer film to support the sample. The multi-well plate was then placed into the diffractometer and analyzed using Cu K radiation ($\alpha_1$ λ=1.54060 Å; $\alpha_2$=1.54443 Å; β=1.39225 Å; $\alpha_1$:$\alpha_2$ ratio=0.5) running in transmission mode (step size 0.01300 2θ, step time 18.87 s) using 40 kV/40 mA generator settings. Data were visualized and images generated using the HighScore Plus 4.7 desktop application (PANalytical, 2017).

Polarized Light Microscopy (PLM)

The presence of crystallinity (birefringence) was determined using an Olympus BX53 microscope, equipped with cross-polarizing lenses and a Motic camera. Images were captured using Motic Images Plus 2.0. All images were recorded using the 20× objective, unless otherwise stated.

Thermogravimetric/Differential Thermal Analysis (TG/DTA)

Approximately 5 mg of material was weighed into an open aluminum pan and loaded into a simultaneous thermogravimetric/differential thermal analyzer (TG/DTA) and held at room temperature. The sample was then heated at a rate of 10° C./min from 20° C. to 300° C. during which time the change in sample weight was recorded along with any differential thermal events (DTA). Nitrogen was used as the purge gas, at a flow rate of 300 $cm^3$/min.

Thermogravimetric Analysis/Differential Scanning Calorimetry (TGA/DSC)

Approximately, 5-10 mg of material was added into a pre-tared open aluminum pan and loaded into a TA Instruments Discovery SDT 650 Auto-Simultaneous DSC and held at room temperature. The sample was then heated at a rate of 10° C./min from 30° C. to 300° C. during which time the change in sample weight was recorded along with the heat flow response (DSC). Nitrogen was used as the purge gas, at a flow rate of 200 $cm^3$/min.

Differential Scanning Calorimetry (DSC)

Approximately, 1-5 mg of material was weighed into an aluminum DSC pan and sealed non-hermetically with an aluminum lid. The sample pan was then loaded into a TA Instruments Discovery DSC 2500 differential scanning calorimeter equipped with a RC90 cooler. The sample and reference were heated to 240° C. at a scan rate of 10° C./min and the resulting heat flow response monitored. The sample was re-cooled to 20° C. and then reheated again to 240° C. all at 10° C./min. Nitrogen was used as the purge gas, at a flow rate of 50 $cm^3$/min.

Nuclear Magnetic Resonance (NMR)

NMR experiments were performed on a Bruker AVIIIHD spectrometer equipped with a DCH cryoprobe operating at 500.12 MHz for protons. Experiments were performed in deuterated dimethyl sulfoxide and each sample was prepared to ca. 10 mM concentration.

Dynamic Vapour Sorption (DVS)

Approximately, 10-20 mg of sample was placed into a mesh vapor sorption balance pan and loaded into a DVS Intrinsic dynamic vapour sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 minutes, maximum step length 500 minutes) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on any solid retained.

High Performance Liquid Chromatography-Ultraviolet Detection (HPLC-UV)

HPLC experiments were performed with the following parameters:

| | |
|---|---|
| Column | Ace Excel 3 C18-PFP, 75 × 4.6 mm, 3 μm |
| Column Temperature (° C.) | 40° C. |
| Flow Rate (mL/min) | 1 |
| Column Pressure at start of Run (Bar) | 210 |
| Injection Volume (μL) | 5 |
| Autosampler Temperature (° C.) | 5° C. |
| Detection parameters | 249 nm |
| Mobile Phase A | 0.1% TFA in $H_2O$ |
| Mobile Phase B | 0.1% TFA in Methanol |
| Diluent | 50:50 $H_2O$:Methanol + 10 μL TFA |

HPLC was run on the following gradient program:

| Time (minutes) | MP A % | MP B % |
|---|---|---|
| 0.0 | 50 | 50 |
| 10.0 | 15 | 85 |
| 10.1 | 50 | 50 |
| 15 | 50 | 50 |

Solutions preparation can be altered to obtain working concentration.

Standard/Sample Preparation: (in Duplicate)

Weigh 10 mg into a 10 mL volumetric flask. Dissolve material in 5 ml of diluent and make to volume with diluent and mix. Std A+B. Working Concentration: 1 mg/ml Sensitivity Solution:

Pipette 50 μL of Std A into a 100 mL volumetric flask. Make the flask to volume and mix. Concentration of the sensitivity solution: 0.0005 mg/mL equivalent to 0.05%.

Calculations:

Detailed calculations required for Chromeleon: Bracketing Standards, calibration curve forced through the origin.

System Suitability:

Precision: 50-2% RSD. Standard verification 98-102%. Sensitivity solution requirement.

Mass Spectrometry

Mass spectrometry experiments were performed with the following parameters:

| | |
|---|---|
| Instrument | Dionex Ultimate 3000 |
| Column | ACE Excel 3 SuperC18, 3.0 μm, 75 × 4.6 mm |
| Autosampler Temperature | Ambient |
| Column Temperature | 30° C. |

-continued

| | |
|---|---|
| Injection Volume | 10 µL |
| Flow Rate | 1.0 mL/min |
| Mobile Phase A | 0.1% Formic Acid in Water |
| Mobile Phase B | 0.1% Formic Acid in Acetonitrile |
| UV Wavelength | 210 nm (monitoring wavelength may be changed as required) |

Gradient Program:

| Time (minutes) | Solvent B [%] |
|---|---|
| 0.00 | 5 |
| 12.00 | 95 |
| 15.00 | 95 |
| 15.10 | 5 |
| 20.00 | 5 |

Both +ve and −ve ESI are used.

Tune Method:

| | |
|---|---|
| Capillary temp | 200° C. |
| Sheath Gas Flow | 20.0 |
| Source Voltage | 4.50 kV |
| Source Current | 80.00 uA |
| Capillary Voltage | 8.0 V |
| Tube Lens Outset | 40.0 V |

Example 1—Synthesis of Compound A

Means of preparing the physical forms of the invention are described below. However, alternative methods (e.g. alternative synthetic routes or sample preparation methods) may be used to provide materials with the same properties as the present invention.

The preparation of Compound A is a two-step process beginning with the starting materials 5-chloro-4-[4-{4-chlorobenzyl)piperazin-1-yl]-3-nitropyridin-2-amine (CR8B) and 1,3-dimethyl-1H-pyrazole-4-carbaldehyde. The representative batch size of Compound A is approximately 1 kg but may be varied as appropriate to meet development and clinical demand. The synthetic route used to manufacture Compound A is outlined below:

Scheme 1 Synthetic route for Compound A

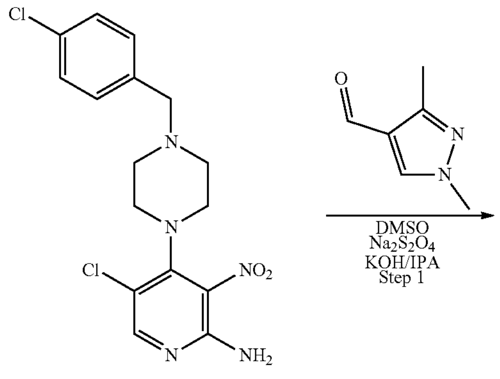

CR8B

-continued

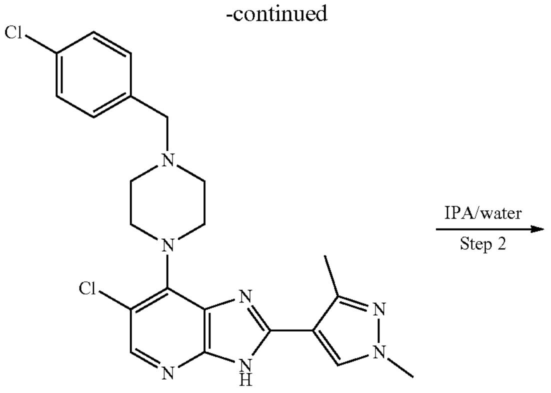

Cruce EP0042

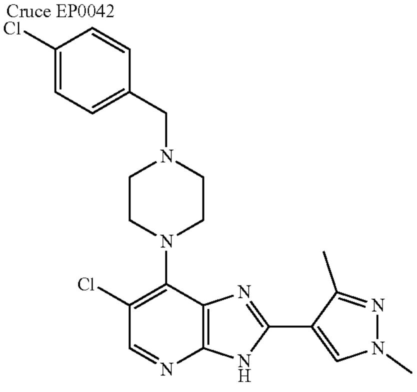

Purified EP0042

Step 1—Crude Compound A

CR8B and 1,3-dimethyl-1H-pyrazole-4-carbaldehyde are dissolved in dimethyl sulfoxide and the mixture is heated gently to approximately 35° C. A slurry of sodium hydrosulphite in water is added in portions allowing the temperature to exotherm (maximum temp approx. 72° C.). Following addition, the reaction is allowed to stabilise at 80° C.±5° C. and is maintained at this temperature until the reaction is complete. The reaction is cooled to <15° C., then an aqueous solution of potassium hydroxide is added by dropwise addition to a pH of 9-10, while maintaining the temperature at <20° C. The slurry is stirred at this temperature for approximately 15 to 30 minutes.

The slurry is filtered, and the crude product washed with water. The crude solid is slurried in water at approximately 40° C. with agitation, then cooled and the solid isolated by filtration. The solid is slurry washed on the filter using water, followed by 2-propanol/water and then dried under vacuum at <60° C.

Step 2—Purified Compound A

Crude Compound A is slurried in 2-propanol (IPA) under nitrogen. Water is added and the mixture heated to a gentle reflux and stirred at this temperature for approximately 30 minutes. The mixture is then cooled with stirring to 2-8° C. The product is isolated by filtration and dried under vacuum at <60° C.

Preparation of Salts

Compound a Mono Fumarate

Purified Compound A (1 eq) and excess fumaric acid (1.15 eq) are dissolved in warm n-propanol (26 relative volumes). The mixture is heated to reflux and is stirred for approximately 60 minutes.

The solution is clarified by hot filtration and the solution is concentrated by approximately 25% by vacuum distillation at approximately 60° C.

The mixture is heated again to reflux, then cooled to approximately 3° C. and the product isolated by filtration. The product is washed with ethyl acetate (2×1 vol), pulled dry and dried under vacuum at <50° C.

Compound A Hemi-Fumarate

Purified Compound A (around 25 mg) is dissolved in 100 to 300 μl of dichloromethane, or acetone:water (10%), and mixed with 0.5 equivalents of fumaric acid. The mixture is then subjected to temperature cycling (3 days of four-hour ambient to 40° C. cycles at a cooling/heating rate of 1° C./min), and the solid was isolated and dried. If no solid is formed, ethyl acetate can be added to encourage precipitation.

Compound A Mesylate

Purified Compound A (around 25 mg) is dissolved in 100 to 300 μl of dichloromethane, ethyl acetate, 2-propanol, tetrahydrofuran, or acetone:water (10%), and mixed with 1 or 2 equivalents of methane sulfonic acid. The mixture is then subjected to temperature cycling (3 days of four-hour ambient to 40° C. cycles at a cooling/heating rate of 1° C./min), and the solid was isolated and dried. If no solid is formed, ethyl acetate can be added to encourage precipitation.

Compound a Hydrochloride (Mono- or Di-Hydrochloride)

Purified Compound A (around 25 mg) is dissolved in 100 to 300 μl of dichloromethane, ethyl acetate, 2-propanol, N-methyl-2-pyrrolidone, tetrahydrofuran, or acetone:water (10%), and mixed with 1 or 2 equivalents of hydrochloric acid. The mixture is then subjected to temperature cycling (3 days of four-hour ambient to 40° C. cycles at a cooling/heating rate of 1° C./min), and the solid was isolated and dried. If no solid is formed, ethyl acetate can be added to encourage precipitation.

Compound a Malate (Mono- or Di-Malate)

Purified Compound A (around 25 mg) is dissolved in 100 to 300 μl of acetone:water (10%), and mixed with 1 or 2 equivalents of malic acid. The mixture is then subjected to temperature cycling (3 days of four-hour ambient to 40° C. cycles at a cooling/heating rate of 1° C./min), and the solid was isolated and dried. If no solid is formed, ethyl acetate can be added to encourage precipitation.

Compound a Sulfate (Mono- or Di-Sulfate)

Purified Compound A (around 25 mg) is dissolved in 100 to 300 μl of, ethyl acetate, 2-propanol, N-methyl-2-pyrrolidone, tetrahydrofuran, or acetone:water (10%), and mixed with 1 or 2 equivalents of sulfuric acid. The mixture is then subjected to temperature cycling (3 days of four-hour ambient to 40° C. cycles at a cooling/heating rate of 1° C./min), and the solid was isolated and dried. If no solid is formed, ethyl acetate can be added to encourage precipitation.

Compound A L-Tartrate

Purified Compound A (around 25 mg) is dissolved in 100 to 300 μl of tetrahydrofuran and mixed with 1 or 2 equivalents of L-tartaric acid. The mixture is then subjected to temperature cycling (3 days of four-hour ambient to 40° C. cycles at a cooling/heating rate of 1° C./min), and the solid was isolated and dried. If no solid is formed, ethyl acetate can be added to encourage precipitation.

Preparation of Crystalline Forms—General Techniques

Lyophilisation

Preparation of the physical forms of Compound A uses lyophilised Compound A fumarate as a starting material. Lyophilised Compound A fumarate (the "lyophile") can be prepared as described below.

1.2 g of Compound A monofumarate as prepared above was weighed into a beaker and dissolved in 84 ml of 1,4-dioxane. Gentle heating was applied until dissolution was observed. The solution was then split between 24×2 mL vials (50 mg/ml per vial), and the solutions then frozen and lyophilized using a Lablyo mini freeze drier. Samples were frozen at −50° C. then held at 19-22° C. and solvent was removed under vacuum at 0.09 mbar. Once lyophilized, a sub-sample was analyzed by XRPD and found to be a mixture of Form 2 Crystallisation techniques Temperature Cycling A slurry of Compound A fumarate lyophile is prepared by adding aliquots of solvent to the lyophile until a mobile slurry was observed. Solvents and volumes can be found in Table 1 below. The slurries are temperature cycled with agitation, between ambient (ca. 25° C.) and 40° C. in 4-hour cycles over 72 hours. Post-temperature cycling the samples were filtered via centrifugation. Isolated solids can be analysed by XRPD.

Saturated solution (mother liquor) from the temperature cycling experiments can be used for further experiments. The mother liquor can be filtered through 0.22 μm syringe filters to remove any potential seed material and split between vials for use in preparation of further crystalline forms.

Anti-Solvent Addition

The selected anti-solvent can be added to the mother liquors of Compound A fumarate obtained from temperature cycling experiments. Anti-solvent can be added in 100 μL aliquots until precipitation is observed or until 1 mL had been added. The samples can be capped and stored at 5° C. for 3 days to promote precipitation. Any resulting solid is analysed by XRPD. Selected anti-solvents and volumes are detailed in Table 1.

Crash Cooling

The saturated solutions (mother liquors) of Compound A fumarate produced from temperature cycling experiments were placed into the fridge at ca. 4° C. After 24 hours, observations were made. Samples in which clear solutions were observed were placed into the freezer at ca. −18° C. for 7 days.

Evaporation

Saturated solutions (mother liquors) of Compound A fumarate produced from temperature cycling experiments can be transferred to 2 mL vials. These vials are uncapped and allowed to evaporate under ambient conditions. Observations are made after 3 days and any solids produced are analyzed by XRPD.

Solvent Drop-Grinding

10 μL of saturated solutions of Compound A fumarate produced from temperature cycling experiments can be added to 20 mg of lyophilised material in bead mill vials. 2×2.4 mm aluminum balls are placed into each vial. The milling of Compound A is completed by a Precellys® Evolution SUPER Homogenizer using the following procedure:

Speed: 4500 RPM;

Cycle time: 30 seconds;

Cycle repeats: 3;

Pause time between each cycle: 10 seconds;

Solids are analysed by XRPD.

TABLE 1

| Volume of Solvent Used During the Primary Polymorph Screening Experiments | | | | | | |
|---|---|---|---|---|---|---|
| Solvent system | | Volume (μL) | | | | |
| Solvent | Anti-Solvent | Temperature cycling | Anti-solvent | Cooling | Evaporation | Drop-grinding |
| 1,1-Dimethoxymethane | Methanol | 1600 | 400 | 400 | 350 | 10 |
| 1,4-Dioxane | Heptane | 400 | 100 | 100 | 75 | 10 |
| 1-Butanol | tert-butylmethyl ether | 700 | 175 | 175 | 150 | 10 |
| 1-Propanol | tert-butylmethyl ether | 3500 | 875 | 875 | 850 | 10 |
| 2-Ethoxyethanol | Water | 1500 | 375 | 375 | 350 | 10 |
| 2-Methyl THF | tert-butylmethyl ether | 1000 | 250 | 250 | 225 | 10 |
| 2-Propanol | Heptane | 1000 | 250 | 250 | 225 | 10 |
| 40% Methanol: 60% Water (% v/v) | tert-butylmethyl ether | 3000 | 750 | 750 | 725 | 10 |
| 80% Methanol: 20% Water (% v/v) | tert-butylmethyl ether | 3000 | 750 | 750 | 725 | 10 |
| 95% Methanol: 5% Water (% v/v) | tert-butylmethyl ether | 3000 | 750 | 750 | 725 | 10 |
| Acetone | tert-butylmethyl ether | 4000 | 1000 | 1000 | 950 | 10 |
| Acetonitrile | tert-butylmethyl ether | 4000 | 1000 | 1000 | 950 | 10 |
| Anisole | Ethanol | 3000 | 750 | 750 | 725 | 10 |
| Butyl Acetate | tert-butylmethyl ether | 1400 | 350 | 350 | 325 | 10 |
| Dimethyl sulfoxide | Methanol | 700 | 175 | 175 | 150 | 10 |
| Ethyl Acetate | tert-butylmethyl ether | 2500 | 625 | 625 | 600 | 10 |
| Isopropyl Acetate | Methanol | 1400 | 350 | 350 | 325 | 10 |
| Methanol | tert-butylmethyl ether | 4000 | 1000 | 1000 | 950 | 10 |
| Methylethyl Ketone | tert-butylmethyl ether | 1600 | 400 | 400 | 375 | 10 |
| Methyl isobutyl Ketone | tert-butylmethyl ether | 4000 | 1000 | 1000 | 950 | 10 |
| N,N'-Dimethylacetamide | Water | 200 | 50 | 50 | 40 | 10 |
| N,N'-Dimethylformamide | tert-butylmethyl ether | 200 | 50 | 50 | 40 | 10 |
| N-Methyl pyrrolidone | Water | 200 | 50 | 50 | 40 | 10 |
| Tetrahydrofuran | tert-butylmethyl ether | 1600 | 400 | 400 | 375 | 10 |
| Toluene | tert-butylmethyl ether | 3000 | 750 | 750 | 725 | 10 |
| Water | Acetonitrile | 3000 | 750 | 750 | 725 | 10 |
| Benzyl Alcohol | Isopropyl acetate | 800 | 200 | 200 | 175 | 10 |
| Tert-Butylmethyl Ether | n-pentane | 2600 | 650 | 650 | 625 | 10 |

Preparation of Form 1

Form 1 was prepared by taking approximately 175 mg of lyophilised Compound A fumarate as prepared above and adding 1-butanol, 1-propanol, 2-ethoxyethanol, acetone, or acetonitrile in the amount listed in the "Temperature Cycling" column in Table 1 above to form a mobile slurry. Temperature cycling was carried out using the conditions described above (4-hour cycles between ambient (ca. 25° C. and 40° C., with agitation, for 72 hours). Following temperature cycling, solid crystalline material was filtered by centrifugation and characterised by XRPD as Form 1.

Form 1 was also prepared from 10 μL of saturated Compound A fumarate solution in 1,1-dimethyoxmethane or DMSO, which was added to 20 mg of lyophilised Compound A in bead mill vials, and subjecting to the solvent drop grinding process described above. Solid was isolated and characterised by XRPD as Form 1.

Form 1 was also prepared by dissolving Purified Compound A (1 eq) and excess fumaric acid (1.15 eq) in warm n-propanol (26 relative volumes), and heating the mixture to reflux and stirring for approximately 60 minutes. The solution is clarified by hot filtration and the solution is concentrated by approximately 25% by vacuum distillation at approximately 60° C. The mixture is heated again to reflux, then cooled to approximately 3° C. and the product isolated by filtration. The product is washed with ethyl acetate (2×1 vol), pulled dry and dried under vacuum at <50° C. Solid was isolated and characterised by XRPD as Form 1.

XRPD Peaks for Form 1:

| Pos. [°2θ] | Height [cts] | Rel. Int. [%] |
|---|---|---|
| 5.92 | 1590.6 | 35.5 |
| 7.07 | 747.7 | 16.7 |
| 10.55 | 665.8 | 14.9 |
| 11.19 | 745.6 | 16.6 |
| 12.86 | 2370.4 | 52.9 |
| 13.75 | 859.6 | 19.2 |
| 14.83 | 932.1 | 20.8 |
| 16.38 | 514.7 | 11.5 |
| 17.53 | 1774.7 | 39.6 |
| 18.28 | 862.0 | 19.2 |
| 19.59 | 1430.0 | 31.9 |
| 20.52 | 1031.0 | 23.0 |
| 21.19 | 4480.9 | 100.0 |
| 22.88 | 3149.2 | 70.3 |
| 23.37 | 1606.1 | 35.8 |
| 24.42 | 814.3 | 18.2 |
| 25.87 | 607.0 | 13.6 |
| 26.83 | 1018.6 | 22.7 |
| 27.11 | 1437.3 | 32.1 |
| 29.13 | 506.8 | 11.3 |

Preparation of Form 2

Form 2 was prepared by dissolving approximately 330 mg of Compound A monofumarate as prepared above into in a 20 mL glass vial in 33 mL of 1,4-dioxane. Gentle heating was applied until dissolution was observed. The solution was then split equally between 33×1.5 mL vials (ca. 10 mg per vial), the solutions then frozen and lyophilized using a Lablyo mini freeze drier. The solid material was analysed by XPRD and found to be Form 2.

Form 2 was also prepared by taking approximately 175 mg of lyophilised Compound A fumarate as prepared above and adding 400 μL 1,4-dioxane to form a mobile slurry. Temperature cycling was carried out using the conditions described above (4-hour cycles between ambient and 40° C., with agitation, for 72 hours). Following temperature cycling, the material was dried at 40° C. under ambient pressure and characterised by XRPD as Form 2 (FIG. 10).

XRPD Peaks for Form 2:

| Pos. [°2θ] | Height [cts] | Rel. Int. [%] |
|---|---|---|
| 7.22 | 871.6 | 36.0 |
| 9.34 | 818.3 | 33.8 |
| 10.74 | 501.2 | 20.7 |
| 13.53 | 835.2 | 34.5 |
| 15.43 | 784.3 | 32.4 |
| 15.80 | 1229.7 | 50.8 |
| 16.28 | 727.1 | 30.0 |
| 17.78 | 1102.7 | 45.6 |
| 18.73 | 383.5 | 15.9 |
| 18.91 | 698.1 | 28.8 |
| 21.55 | 457.8 | 18.9 |
| 22.08 | 393.0 | 16.2 |
| 22.40 | 411.3 | 17.0 |
| 22.60 | 562.4 | 23.2 |
| 23.94 | 564.0 | 23.3 |
| 24.52 | 2420.5 | 100.0 |
| 25.20 | 338.8 | 14.0 |
| 25.71 | 932.5 | 38.5 |
| 27.29 | 804.9 | 33.3 |
| 29.14 | 494.9 | 20.5 |

Preparation of Form 3

Form 3 was prepared by taking approximately 175 mg of lyophilised Compound A fumarate as prepared above and adding dimethoxymethane; 2-MeTHF; water:MeOH (0:100, 40:60, 80:20, 95:5, 100:0); or IPA in the amount listed in Table 1 above to form a mobile slurry. Temperature cycling was carried out using the conditions described above (4-hour cycles between ambient and 40° C., with agitation, for 72 hours). Following temperature cycling, solid crystalline material was filtered by centrifugation and characterised by XRPD as Form 3.

Form 3 was also prepared by taking 10 mg of lyophilised Compound A fumarate as prepared above in a glass vial and adding water:MeOH (0:100, 40:60, 80:20, 95:5, 100:0); EtOAc; MEK; acetone; or acetonitrile in 100 μL aliquots, with heating and stirring at 40° C. until dissolution occurred or until 2 ml had been added the amounts. The vial was uncapped and allowed to evaporate under ambient conditions. Solid was isolated and characterised by XRPD as Form 3.

Form 3 was also prepared by taking a 1600 μl saturated solution of Compound A fumarate, filtering it through a 0.22 μL syringe filter and adding 1000 μL of TMBE antisolvent in 100 μL aliquots, followed by storage at 5° C. for 3 days. The solid produced was isolated and characterised by XRPD as Form 3.

XRPD Peaks for Form 3:

| Pos. [°2θ] | Height [cts] | Rel. Int. [%] |
|---|---|---|
| 3.68 | 1190.1 | 41.0 |
| 7.37 | 1104.6 | 38.1 |
| 8.82 | 2901.2 | 100.0 |
| 12.64 | 422.0 | 14.5 |
| 15.55 | 1030.9 | 35.5 |
| 17.40 | 851.6 | 29.4 |

-continued

| Pos. [°2θ] | Height [cts] | Rel. Int. [%] |
|---|---|---|
| 17.70 | 869.1 | 30.0 |
| 18.17 | 1495.8 | 51.6 |
| 18.76 | 844.9 | 29.1 |
| 19.43 | 464.8 | 16.0 |
| 19.63 | 429.4 | 14.8 |
| 20.44 | 920.2 | 31.7 |
| 22.47 | 1165.3 | 40.2 |
| 22.76 | 472.2 | 16.3 |
| 24.81 | 502.7 | 17.3 |
| 25.74 | 403.4 | 13.9 |
| 26.78 | 480.1 | 16.6 |
| 26.99 | 502.8 | 17.3 |
| 27.12 | 439.8 | 15.2 |
| 28.33 | 428.2 | 14.8 |

Preparation of Form 4

Form 4 was prepared by taking approximately 175 mg of lyophilised Compound A fumarate as prepared above and adding 400 μL 1,4-dioxane to form a mobile slurry. Temperature cycling was carried out using the conditions described above (4-hour cycles between ambient and 40° C., with agitation, for 72 hours). Following temperature cycling, solid crystalline material was filtered by centrifugation and characterised by XRPD as Form 4.

XRPD Peaks for Form 4:

| Pos. [°2θ] | Height [cts] | Rel. Int. [%] |
|---|---|---|
| 5.1 | 150.3 | 12.6 |
| 7.7 | 422.8 | 35.5 |
| 8.1 | 198.0 | 16.6 |
| 9.3 | 209.8 | 17.6 |
| 10.1 | 284.9 | 23.9 |
| 13.7 | 161.3 | 13.6 |
| 14.4 | 197.9 | 16.6 |
| 15.7 | 254.6 | 21.4 |
| 16.3 | 725.7 | 60.9 |
| 17.3 | 253.5 | 21.3 |
| 18.1 | 516.4 | 43.4 |
| 18.7 | 724.5 | 60.8 |
| 20.0 | 279.5 | 23.5 |
| 20.2 | 245.4 | 20.6 |
| 22.8 | 1190.7 | 100.0 |
| 23.1 | 687.5 | 57.7 |
| 25.7 | 753.0 | 63.2 |
| 26.2 | 210.5 | 17.7 |
| 26.9 | 254.6 | 21.4 |
| 27.8 | 159.9 | 13.4 |

Preparation of Form 5

Form 5 was prepared by taking approximately 175 mg of lyophilised Compound A fumarate as prepared above and adding 800 μL benzyl alcohol to form a mobile slurry. Temperature cycling was carried out using the conditions described above (4-hour cycles between ambient and 40° C., with agitation, for 72 hours). Following temperature cycling, solid crystalline material was filtered by centrifugation and characterised by XRPD as Form 5.

XRPD Peaks for Form 5:

| Pos. [°2θ] | Height [cts] | Rel. Int. [%] |
|---|---|---|
| 5.5 | 634.6 | 28.6 |
| 8.3 | 541.2 | 24.4 |
| 11.4 | 231.4 | 10.4 |
| 15.7 | 453.6 | 20.5 |
| 15.9 | 321.7 | 14.5 |
| 16.6 | 646.1 | 29.1 |

-continued

| Pos. [°2θ] | Height [cts] | Rel. Int. [%] |
|---|---|---|
| 18.6 | 532.5 | 24.0 |
| 18.9 | 457.6 | 20.6 |
| 19.3 | 231.0 | 10.4 |
| 19.5 | 299.7 | 13.5 |
| 21.5 | 678.4 | 30.6 |
| 22.2 | 325.8 | 14.7 |
| 22.4 | 356.3 | 16.1 |
| 23.2 | 405.2 | 18.3 |
| 24.5 | 2218.6 | 100.0 |
| 26.1 | 254.1 | 11.5 |
| 26.4 | 454.6 | 20.5 |
| 26.7 | 342.3 | 15.4 |
| 27.3 | 783.0 | 35.3 |
| 29.8 | 157.5 | 7.1 |

Preparation of Form 6

Form 6 was prepared by taking approximately 175 mg of lyophilised Compound A fumarate as prepared above and adding 700 μL DMSO to form a mobile slurry. Temperature cycling was carried out using the conditions described above (4-hour cycles between ambient and 40° C., with agitation, for 72 hours). Following temperature cycling, solid crystalline material was filtered by centrifugation and characterised by XRPD as Form 6.

XRPD Peaks for Form 6:

| Pos. [°2θ] | Height [cts] | Rel. Int. [%] |
|---|---|---|
| 9.06 | 453.3 | 38.2 |
| 9.39 | 256.8 | 21.6 |
| 9.79 | 221.8 | 18.7 |
| 12.73 | 426.9 | 36.0 |
| 15.21 | 322.0 | 27.1 |
| 15.96 | 1186.5 | 100.0 |
| 16.20 | 178.8 | 15.1 |
| 17.24 | 393.1 | 33.1 |
| 17.87 | 222.8 | 18.8 |
| 19.77 | 299.6 | 25.3 |
| 20.41 | 616.3 | 51.9 |
| 21.03 | 446.9 | 37.7 |
| 22.00 | 355.2 | 29.9 |
| 22.34 | 317.6 | 26.8 |
| 22.53 | 223.2 | 18.8 |
| 22.92 | 313.0 | 26.4 |
| 24.47 | 308.8 | 26.0 |
| 25.20 | 322.4 | 27.2 |
| 26.39 | 739.9 | 62.4 |
| 28.97 | 238.2 | 20.1 |

Preparation of Form 7

Form 7 was prepared by taking approximately 175 mg of lyophilised Compound A fumarate as prepared above and adding 4000 μL methanol to form a mobile slurry. Temperature cycling was carried out using the conditions described above (4-hour cycles between ambient and 40° C., with agitation, for 72 hours). Following temperature cycling, solid crystalline material was filtered by centrifugation and characterised by XRPD as Form 7.

Form 7 was also prepared by taking approximately 400 mg of Form 6 material and slurrying in 0.5 ml of TBME at ambient temperature for 24 hours. The solids were then isolated via centrifugation and left to dry under ambient conditions. TG/DTA analysis revealed a lower DMSO content than Form 6, so the sample was slurried again in to 2 ml of TBME at ambient temperature for 72 hours. Solids isolated via centrifugation were characterised by XRPD as Form 7.

XRPD Peaks for Form 7:

| Pos. [°2θ] | Height [cts] | Rel. Int. [%] |
|---|---|---|
| 4.31 | 1002.84 | 100 |
| 6.39 | 548.16 | 54.66 |
| 7.53 | 249.61 | 24.89 |
| 7.89 | 283.8 | 28.3 |
| 12.56 | 232.62 | 23.2 |
| 12.78 | 173.35 | 17.29 |
| 13.71 | 261.91 | 26.12 |
| 14.38 | 502.75 | 50.13 |
| 15.74 | 445.36 | 44.41 |
| 16.23 | 329.93 | 32.9 |
| 16.89 | 307.3 | 30.64 |
| 18.50 | 325.12 | 32.42 |
| 19.49 | 250.78 | 25.01 |
| 19.94 | 483.24 | 48.19 |
| 22.16 | 353.64 | 35.26 |
| 23.06 | 346.52 | 34.55 |
| 23.39 | 244.57 | 24.39 |
| 23.56 | 242.87 | 24.22 |
| 25.61 | 904.37 | 90.18 |
| 26.24 | 883.23 | 88.07 |

Preparation of Form 8

Form 8 was prepared from 10 μL of saturated Compound A fumarate solution in benzyl alcohol, which was added to 20 mg of lyophilised Compound A in bead mill vials, and subjected it to the solvent drop grinding process described above. The sample showed a large quantity of benzyl alcohol by DT analysis, so the sample was slurried in TBME. Solid was isolated and characterised by XRPD as Form 8.

XRPD Peaks for Form 8:

| Pos. [°2θ] | Height [cts] | Rel. Int. [%] |
|---|---|---|
| 5.17 | 437.9 | 27.2 |
| 5.53 | 896.5 | 55.6 |
| 8.15 | 537.7 | 33.4 |
| 10.36 | 443.9 | 27.5 |
| 10.70 | 347.6 | 21.6 |
| 11.07 | 514.9 | 32.0 |
| 15.52 | 896.0 | 55.6 |
| 16.30 | 548.0 | 34.0 |
| 16.49 | 1049.7 | 65.1 |
| 17.15 | 450.7 | 28.0 |
| 18.36 | 427.1 | 26.5 |
| 18.84 | 329.3 | 20.4 |
| 19.33 | 372.0 | 23.1 |
| 21.43 | 426.2 | 26.4 |
| 23.26 | 543.4 | 33.7 |
| 24.24 | 1611.8 | 100.0 |
| 24.51 | 1024.0 | 63.5 |
| 25.48 | 356.6 | 22.1 |
| 25.72 | 402.7 | 25.0 |
| 26.75 | 405.1 | 25.1 |

Example 4: Assessment of Compound A Salts

The mono-mesylate, di-mesylate, mono-hydrochloride, di-hydrochloride and fumarate salts of Compound A were assessed for compliance with the following properties identified by the inventors as being relevant to pharmaceutical suitability:

| Score criteria | 1 | 2 | 3 |
|---|---|---|---|
| Aqueous solubility (mg/ml) | <<0.06 | ~0.05 to 4 | >4 |

-continued

| Score criteria | 1 | 2 | 3 |
|---|---|---|---|
| Purity (HPLC % peak area @308 nm) | <96.5 | 96.5 to 98 | >98 |
| DVS (% mass change @ 90% RH) | >2.5% | 1.5 to 2.5 | <1.5 |
| Potency (% Compound A) | <85 | 85-95 | >95 |
| Elemental analysis/stoichiometry | no | further tests required | Yes |
| Processability | unsatisfactory | satisfactory | Good |
| Dissolution (% release @ 45 minutes) | <80 | 80-90 | >90 |

Aqueous solubility was determined by weighing out ~3 mg of the salt form into a clean HPLC vial, adding HPLC grade water, shaking, vortexing, and/or sonicating to mix and aid dissolution as necessary. Once fully dissolved (clear solution) solubility is calculated based on the amount of water added. HPLC purity and DVS can be determined using methods described herein or methods known in the art. Processability is based on solubility of the salt form in certain excipients. Automated elemental analysis can be performed with 10 mg of the Compound A salt, using caffeine as a reference material. CHNX and the stoichiometry of the salt to the Compound A is determined. Dissolution was determined across 4 pH values (2.0, 3.8, 5.3, 7.2) using a Sirius T3 module, SOP 2070 and 2071, with 5 to 10 mg of Compound A salt compressed into a tablet disc.

The results are shown in FIG. 39—as can be seen the fumarate salt has the best overall balance of properties, notably unexpectedly low hygroscopicity that was comparable to that of the free base.

Example 5: Stability of Form 1

The stability of Form 1 was tested for compliance with the following stability acceptance criteria:

| Test | Acceptance criteria |
|---|---|
| Appearance | Yellow powder free from visible impurities |
| Purity by HPLC | ≥97% |
| Related impurities by HPLC | No single impurity ≥1%<br>Report all impurities ≥0.05% |

Form 1 was prepared as described in Example X above. The following amounts of Form 1 were weighed into 30 ml HDPE Nalgene containers:

| Storage Condition | Weight of Form 1 |
|---|---|
| 5° C. | 3 g |
| 25° C./60% RH | 2.5 g |
| 40° C./75% RH | 2 g |
| 55° C. | 1.2 g |

Each container was placed into a small grip-seal bag and incubated at the conditions above.

Visual appearance and purity by HPLC were assessed periodically (at 0, 1, 3, 6, 9, 12, and 24 months). Water content was assessed at 0, 1, 6, and 12 months by Karl Fisher titration and TGA. XRPD spectra were taken at 0, 1, 3 and 6 months.

The levels of impurities were very low (≤0.6%) and did not increase over time, as shown in FIG. 40. Changes in mass were negligible, and the water content after 12 months was below the limit of quantification. As shown in FIG. 9, there were no changes in XRPD were observed at any time. Taken together, these observations support the usefulness of Form 1 in the manufacture and development of Compound A.

Example 6: 1-Week Stability Study of Form 3

The stability of Compound A fumarate Form 3 was assessed under ambient and stressed conditions. The following procedure was carried out. Approximately 20 mg of material was added to 3×1.5 mL glass vials. The vials were then stored under the following conditions:

Ambient light and temperature (closed vial)

40° C./75% RH (open vial)

80° C. (closed vial)

After 1 week the samples were collected and analyzed by XRPD and HPLC.

The following observations and result were obtained during the 1-week stability study of Compound A fumarate Form 3. No visual changes were observed in the samples after 1-week. All samples appeared a as a pale yellow free-flowing solid. Compound A fumarate Form 3 was observed in all samples by XRPD. No changes in purity was observed in the samples.

| Storage Condition | Purity (% area) | XRPD |
|---|---|---|
| 40° C./75% RH | 99.5 | Form 3 |
| 80° C. | 99.6 | Form 3 |
| Ambient | 99.6 | Form 3 |

Example 7: Thermodynamic Solubility Assessment

The thermodynamic solubility of Compound A free base, Compound A fumarate Form 1 and Compound A hemi-fumarate Form 3 was assessed in 3 biological media: Fasted State Simulated Intestinal Fluid (FaSSIF); Fed State Simulated Intestinal Fluid (FeSSIF) and Fasted State Simulated Gastric Fluid (FaSSGF).

The following procedure was carried out. Approximately 10 mg of material was weighed into 3×1.5 mL glass vials. 0.02 mL aliquots of appropriate buffer were added to each vial until a final concentration of 10 mg/mL was obtained. The samples were then filtered via centrifugation and the mother liquors analyzed by HPLC.

The following observations and results were obtained during the thermodynamic solubility assessment. Compound A fumarate form 1 was found to be insoluble in FaSSIF. A low solubility of 0.3 mg/mL was observed in FeSSIF. A higher solubility of 3.4 mg/mL was observed in FaSSGF. Compound A fumarate form 3 was found to have low solubility (<0.1 mg/mL) in FaSSIF and FeSSIF. A higher solubility of 2.0 mg/mL was observed in FaSSGF. Compound A free base was found to have low solubility (<0.1 mg/mL) in FaSSIF and FeSSIF. A higher solubility of 1.5 mg/mL was observed in FaSSGF.

| Form | Media | Concentration (mg/mL) |
|---|---|---|
| Compound A fumarate form 1 | FaSSIF pH 6.5 | Below LOD |
| | FeSSIF pH 5.0 | 0.3 |
| | FaSSGF pH 1.6 | 3.4 |
| Compound A fumarate form 3 | FaSSIF pH 6.5 | <0.1 |
| | FeSSIF pH 5.0 | <0.1 |
| | FaSSGF pH 1.6 | 2.0 |
| Compound A free base | FaSSIF pH 6.5 | <0.1 |
| | FeSSIF pH 5.0 | <0.1 |
| | FaSSGF pH 1.6 | 1.5 |

The invention claimed is:

1. A crystalline Form 1 of Compound A fumarate:

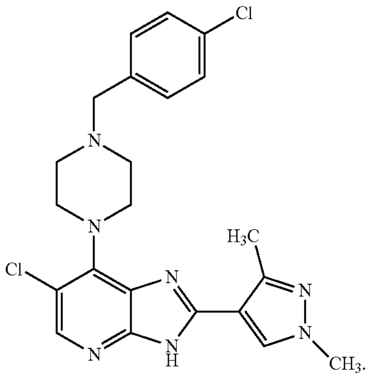 [SMILES: Cc1nn(C)cc1-c1nc2c(N3CCN(Cc4ccc(Cl)cc4)CC3)c(Cl)cnc2[nH]1]

which is characterised by one or more of the following properties:

a) an XRPD pattern with at least the following XRPD peaks (CuK °2θ) at approximately (±0.1): 12.9, 20.5, 21.2, 22.9, and 23.4;

b) an XRPD pattern the same as shown in FIG. 1; and/or c) the following unit cell parameters at 298 K:

| System | a | b | c |
|---|---|---|---|
| Monoclinic P | 9.7(1) Å | 17.4(2) Å | 32.5(1) Å |

| | alpha | beta | gamma | A |
|---|---|---|---|---|
| Monoclinic P | 90 | 88.35 | 90 | 5483 Å$^3$. |

2. A crystalline Form 2, Form 3, Form 4, Form 5 or Form 8 of Compound A fumarate:

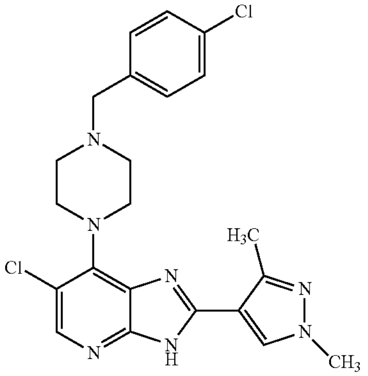 [SMILES: Cc1nn(C)cc1-c1nc2c(N3CCN(Cc4ccc(Cl)cc4)CC3)c(Cl)cnc2[nH]1]

wherein Form 2 is characterised by one or more of the following properties:

i) an XRPD pattern with at least the following XRPD peaks (CuK 2θ) at approximately (±0.1): 15.4, 15.8, 16.3, and 24.5;

ii) an XRPD pattern the same as shown in FIG. 2; and/or iii) the following unit cell parameters at 298 K:

| System | a | b | c | alpha | beta | gamma |
|---|---|---|---|---|---|---|
| Triclinic P | 8.3(1) Å | 14.1(2) Å | 20.8(4) Å | 86.72 | 90.24 | 95.95; |

wherein Form 3 is characterised by one or more of the following properties:

iv) an XRPD pattern with at least the following XRPD peaks (CuK 2θ) at approximately (±0.1): 8.8, 17.4, 17.7, and 18.2;

x) an XRPD pattern the same as shown in FIG. 3; and/or xi) the following unit cell parameters at 298 K:

| System | a | b | c | alpha | beta | gamma | A |
|---|---|---|---|---|---|---|---|
| Triclinic P | 9.7(2) Å | 12.7(3) Å | 24.6(3) Å | 78.92 | 86.15 | 102.2 | 2888 Å$^3$; |

wherein Form 4 is characterized by one or more of the following properties:
xvii) an XRPD pattern with at least the following XRPD peaks (CuK 2θ) at approximately (±0.1): 16.3, 18.7, 22.8, 23.1, 25.7; and/or
xviii) an XRPD pattern the same as shown in FIG. 4;
wherein Form 5 is characterized by one or more of the following properties:
xxiii) an XRPD pattern with at least the following XRPD peaks (CuK 2θ) at approximately (±0.1): 21.5, 24.5, and 27.3;
xxiv) an XRPD pattern the same as shown in FIG. 5; and/or
xxv) the following unit cell parameters at 298 K:

| System | a | b | c | alpha | beta | gamma |
|---|---|---|---|---|---|---|
| Monoclinic P | 32.06(5) Å | 11.28(1) Å | 8.43(1) Å | 90 | 93.65 (2) | 90; |

wherein Form 8 which is characterised by one or more of the following properties:
xxxi) an XRPD pattern with at least the following XRPD peaks (CuK 2θ) at approximately (±0.1): 10.4, 10.7, 11.1, 24.2, and 24.5;
xxxii) an XRPD pattern the same as shown in FIG. 8; and/or
xxxiii) the following unit cell parameters at 298 K:

| System | a | b | c | alpha | beta | gamma |
|---|---|---|---|---|---|---|
| Monoclinic P | 10.67 Å | 14.15 Å | 16.19 Å | 90 | 97.31 | 90; |

3. A method for treating a disease or condition associated with Aurora kinase activity and/or FLT3, comprising administering to a human or animal subject a therapeutically acceptable amount of crystalline Form 1 of Compound A fumarate of claim 1, or crystalline Form 2, Form 3, Form 4, Form 5 or Form 8 of Compound A fumarate of claim 2.

4. A method of treating a proliferative disorder in a human or animal subject, comprising administering to said subject a therapeutically acceptable amount of crystalline Form 1 of Compound A fumarate of claim 1, or a pharmaceutically acceptable amount of crystalline Form 2, Form 3, Form 4, Form 5 or Form 8 of Compound A fumarate of claim 2.

5. The method of claim 4 wherein the proliferative disorder is cancer.

6. The method of claim 4 wherein the proliferative disorder is acute myeloid leukemia (AML).

* * * * *